US012678487B2

(12) United States Patent
Jin et al.

(10) Patent No.: US 12,678,487 B2
(45) Date of Patent: Jul. 14, 2026

(54) TARGETING LUNG-RESIDENT TNFR2+ CDC2 (R2D2) SUBPOPULATION TO TREAT ASTHMA

(71) Applicant: UNIVERSITY OF FLORIDA RESEARCH FOUNDATION, INCORPORATED, Gainesville, FL (US)

(72) Inventors: Lei Jin, Gainesville, FL (US); Samira Mansouri, Gainesville, FL (US)

(73) Assignee: UNIVERSITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 1033 days.

(21) Appl. No.: 17/430,906

(22) PCT Filed: Feb. 13, 2020

(86) PCT No.: PCT/US2020/018037
§ 371 (c)(1),
(2) Date: Aug. 13, 2021

(87) PCT Pub. No.: WO2020/168033
PCT Pub. Date: Aug. 20, 2020

(65) Prior Publication Data
US 2022/0233643 A1 Jul. 28, 2022

Related U.S. Application Data

(60) Provisional application No. 62/805,074, filed on Feb. 13, 2019.

(51) Int. Cl.
| | |
|---|---|
| *A61K 38/21* | (2006.01) |
| *A61K 9/00* | (2006.01) |
| *A61K 38/19* | (2006.01) |
| *A61P 11/06* | (2006.01) |
| *A61P 29/00* | (2006.01) |
| *A61P 37/06* | (2006.01) |
| *C07K 14/525* | (2006.01) |
| *C07K 14/565* | (2006.01) |

(52) U.S. Cl.
CPC .......... *A61K 38/215* (2013.01); *A61K 9/0073* (2013.01); *A61K 38/191* (2013.01); *A61P 11/06* (2018.01); *A61P 37/06* (2018.01)

(58) Field of Classification Search
CPC ..... A61K 38/215; A61K 38/191; A61P 11/06; A61P 37/06
See application file for complete search history.

(56) References Cited

U.S. PATENT DOCUMENTS

| | | | |
|---|---|---|---|
| 5,266,312 | A | 11/1993 | Eung et al. |
| 7,387,271 | B2 | 6/2008 | Noelle et al. |
| 7,871,603 | B2 | 1/2011 | Davies et al. |
| 9,421,243 | B2 | 8/2016 | Tear et al. |
| 2005/0079184 | A1 | 4/2005 | Hsing-Chang et al. |
| 2011/0059044 | A1 | 3/2011 | Condos et al. |

FOREIGN PATENT DOCUMENTS

| | | | | | |
|---|---|---|---|---|---|
| WO | WO-2011110861 | A2 | * | 9/2011 | .............. A61P 31/16 |
| WO | 2014139468 | A1 | | 9/2014 | |
| WO | 2017040312 | A1 | | 3/2017 | |
| WO | 2017194783 | A1 | | 11/2017 | |
| WO | 2019147837 | A2 | | 8/2019 | |
| WO | 2020168033 | A2 | | 8/2020 | |

OTHER PUBLICATIONS

Asthma from Merck Manual, pp. 1-19. Accessed Nov. 2, 2017. (Year: 2017).*
Chronic obstructive pulmonary disease (COPD), Merck Manual, pp. 1-18 . Accessed Oct. 14, 2025. (Year: 2025).*
Cantin et al. "Inflammation in cystic fibrosis lung disease: Pathogenesis and therapy," J. Cystic Fibrosis 14:419-430 (2015) (Year: 2015).*
Katamesh et al., "Inflammatory lung diseases: a clinical and scientific review of the latest advances and challenges," Pharmacological Reports 77:889-906 (2025) (Year: 2025).*
Didkovskyi, V.S. et al., "Technique for Rigidity Determination of the Materials for Ossicles Prostheses of Human Middle Ear", Radioelectronics and Communications Systems, 2015, vol. 58, No. 3, pp. 134-138.
Mansouri, Samira et al., "In vivo reprogramming of pathogenic lung TNFR2+cDC2s by IFNB inhibits HDM-induced asthma", Sci. Immunol. 6, eabi8472 (2021) Jul. 9, 2021.
Mansouri, Samira et al., "Lung IFNAR1hi TNFR2+ cDC2 promotes lung regulatory T cells induction and maintains lung mucosal tolerance at steady state", Mucosal Immunology (2020) 13:595-608.
Neumann, A. et al., "Biomaterials for ossicular chain reconstruction. A review", Biomaterials, 2003, 34, No. 12, pp. 1052-1057.

(Continued)

*Primary Examiner* — Julie Ha
*Assistant Examiner* — Kristina M Hellman
(74) *Attorney, Agent, or Firm* — Timthy H. Van Dyke; Wolter Van Dyke Davis, PLLC

(57) ABSTRACT

Provided herein are compositions and methods for treating an inflammatory respiratory disorder. Exemplified are compositions comprising interferon-beta of IFN-beta-fusion peptides.

12 Claims, 25 Drawing Sheets
Specification includes a Sequence Listing.

(56) References Cited

OTHER PUBLICATIONS

Djukanovic, Ratko et al., "The Effect of Inhaled IFN-B on Worsening of Asthma Symptoms Caused by Viral Infections", Am. J. Respir. Crit. Care Med. vol 190, Issue 2, pp. 145-154, Jul. 15, 2014.

McCrae, C. et al., "On-Demand Inhaled Interferon-Bata 1a for the Prevention of Severa Asthma Exacerbations: Results of the Inexas Phase 2a Study", American Journal of Respiratory and Critical Care Medicine, 2018, 197:A6165 Abstract Only.

PCT/US2020/18037, Search Report and Written Opinion mailed date Sep. 3, 2020, 14 pages.

Mansouri, Samira et al., "In vivo reprogramming of pathogenic lung TNFR2+cDC2s by IFNB inhibits HDM-induced asthma," Sci. Immunol. 6, eabi8472, Jul. 9, 2021, 14 pages.

Mansouri, Samira et al., "Lung IFNAR1hi TNFR2+ cDC2 promotes lung regulatory T cells induction and maintains lung mucosal tolerance at steady state", Mucosal Immunology (2020) 13:595-608; https://doi.org/10.1038 $41385-020-0254-1.

* cited by examiner

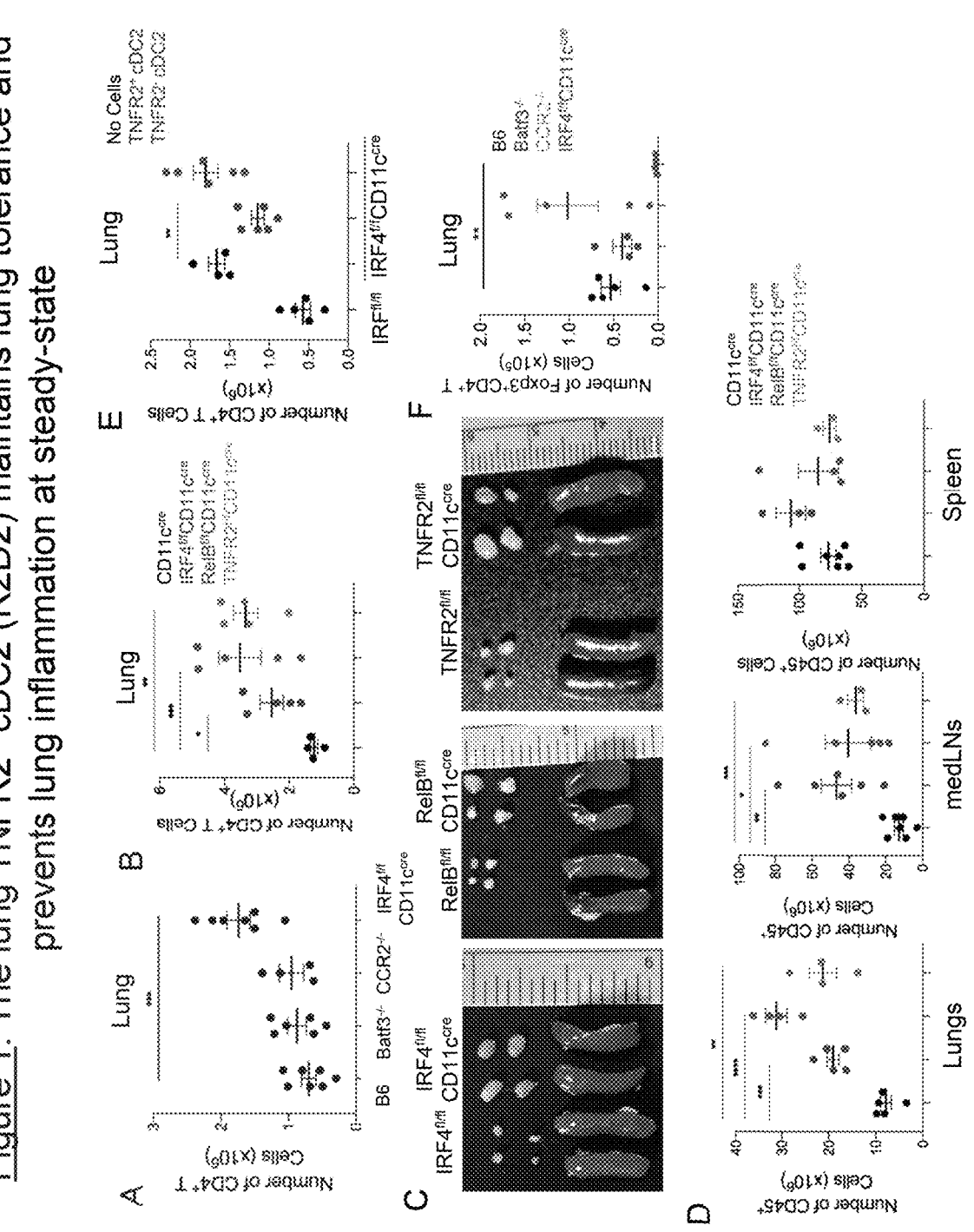
Figure 1: The lung TNFR2+ cDC2 (R2D2) maintains lung tolerance and prevents lung inflammation at steady-state

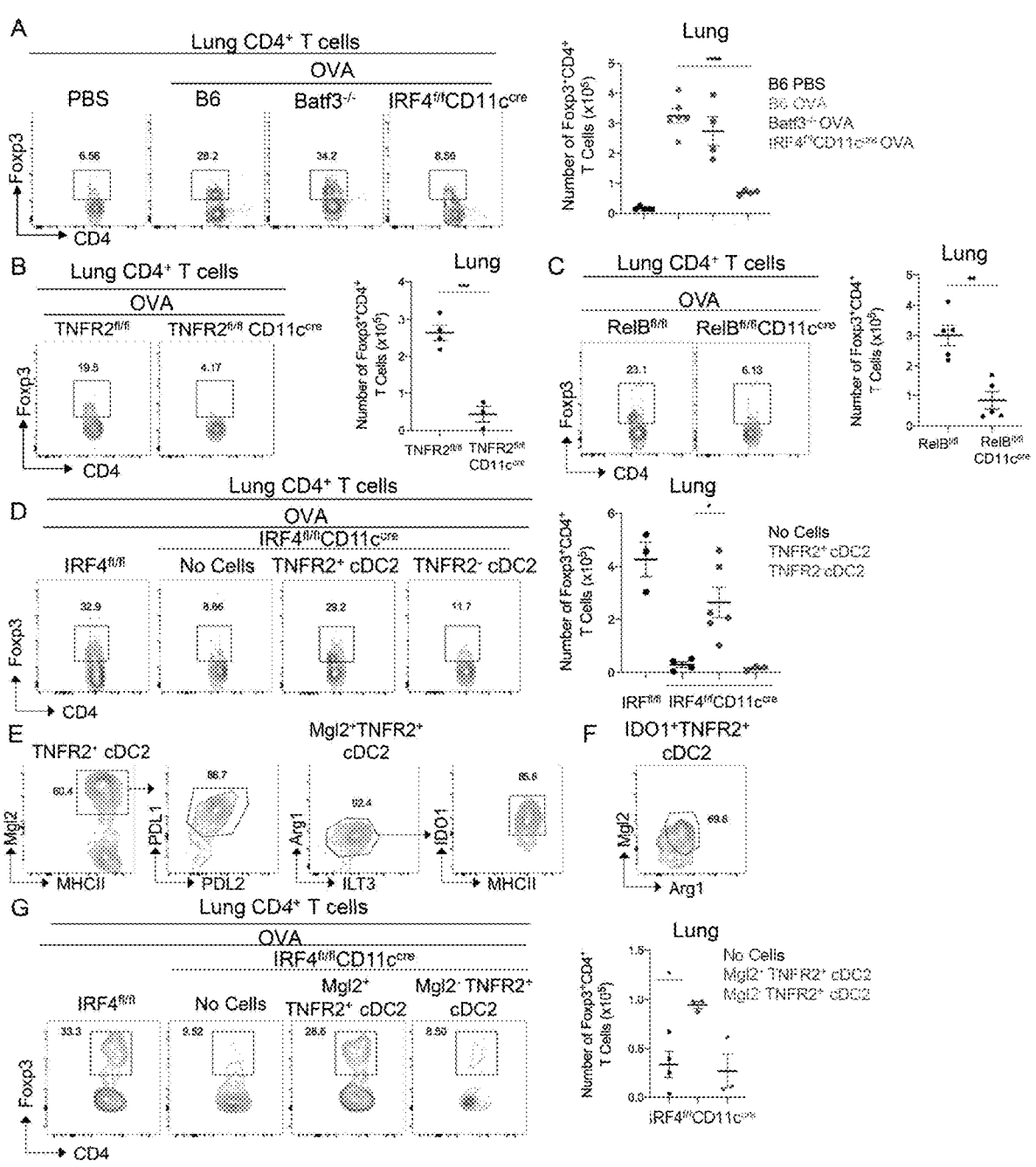
Figure 2: Lung Mgl2⁺/IDO-1⁺ R2D2 population generates T-regs in the lung Figure 3: Tonic TNFR2 signaling is required for the presence of the R2D2 population in the lung Figure 4: IFNβ-IFNAR1 signaling in iR2D2 cells promotes T-regs induction in the lung Figure 5: IFNβ-IFNAR1-TGFβ1 signaling in iR2D2 promotes lung T-regs induction Figure 6: R2D2 promotes T$_H$2 responses in HDM mice
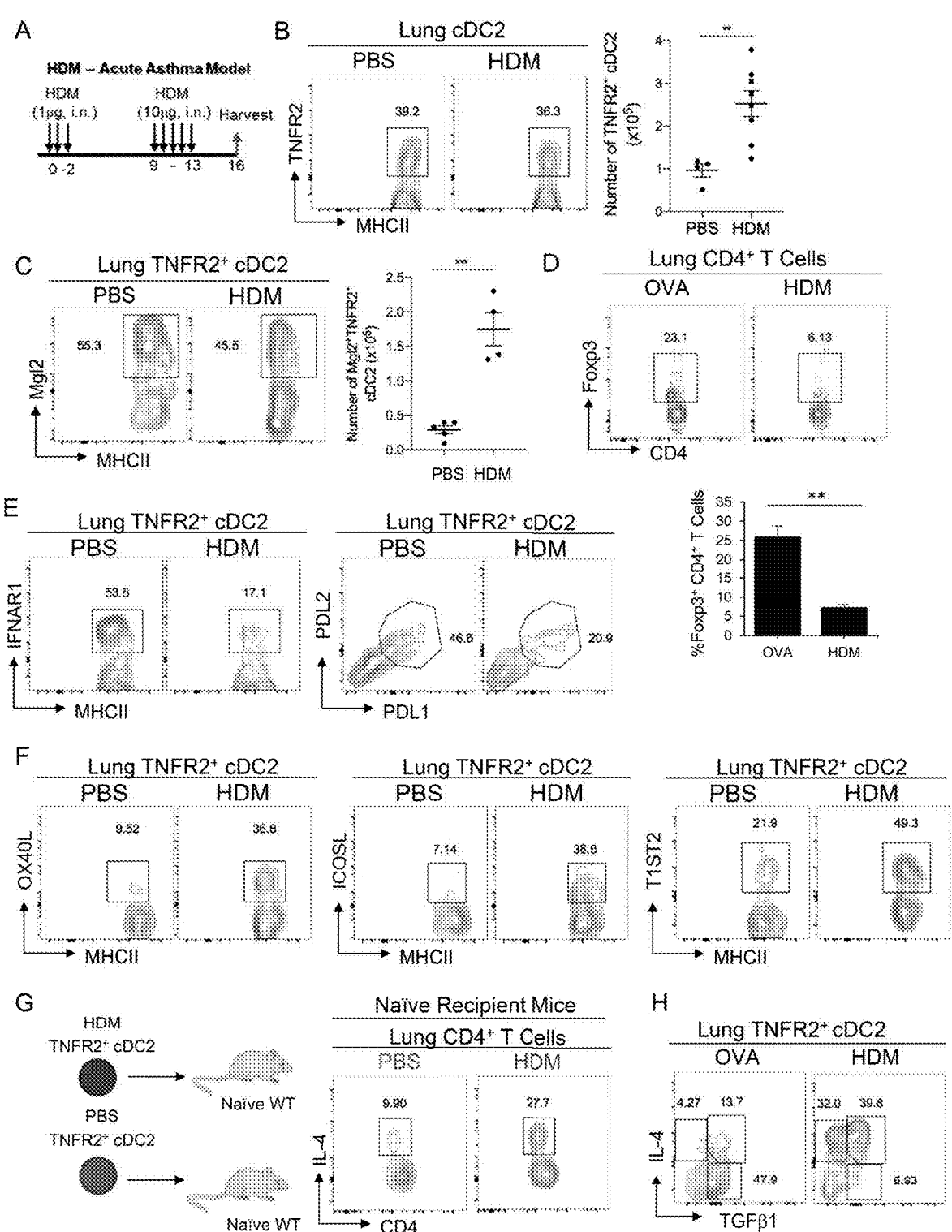

Figure 7: Lung TNFR2+ cDC2 in healthy and lung diseases patients

Figure 8: Lung epithelium IFNβ − IFNAR1$^{hi}$ R2D2 − T-regs axis maintains lung mucosal tolerance at the steady-state
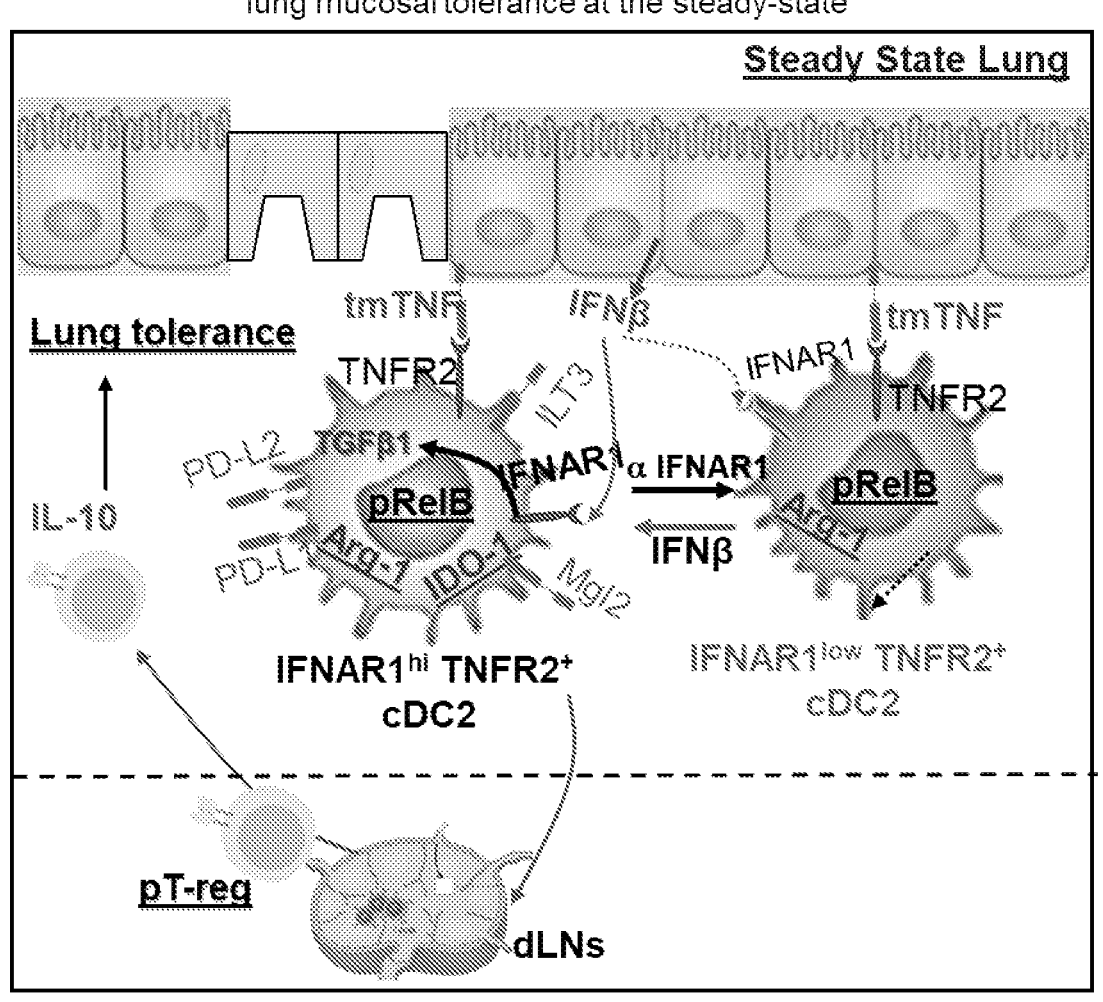

Figure 9: Gating strategies for lung DCs subsets
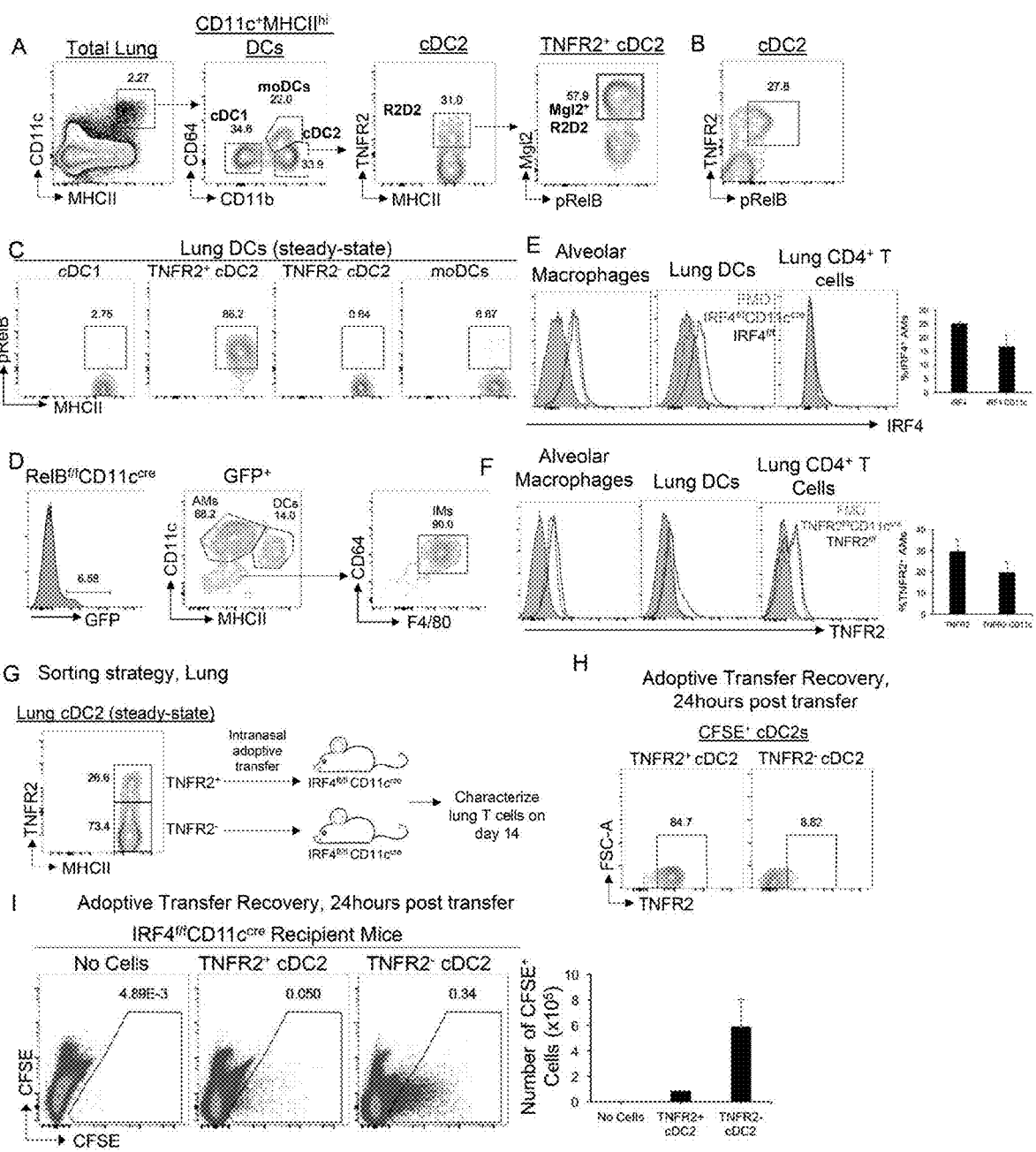

Figure 10: Innocuous inhaled protein antigens induce peripheral T-regs in the lung Figure 11: Tonic TNFR2 signaling is required for the presence of the R2D2 population in the lung Figure 12 : IFNβ-IFNAR1 signaling in iR2D2 cells promotes T-regs induction in the lung
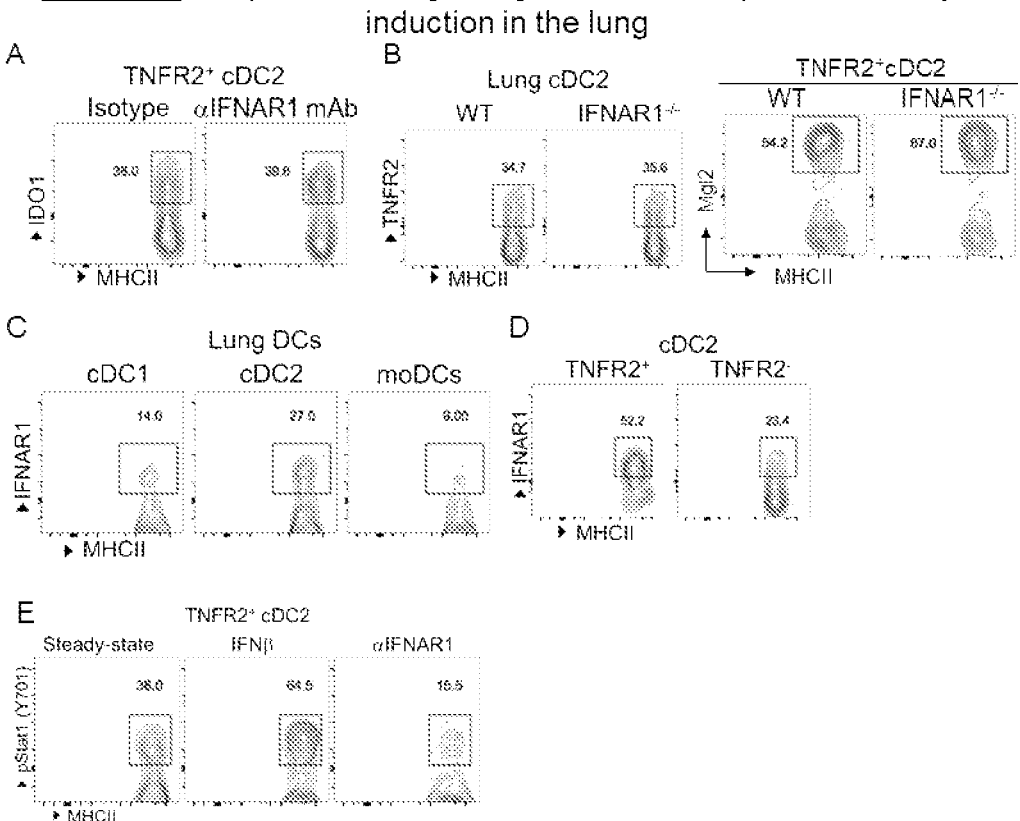
Figure 13 : IFNβ-IFNAR1-TGFβ1 signaling axis in iR2D2 promotes T-regs induction
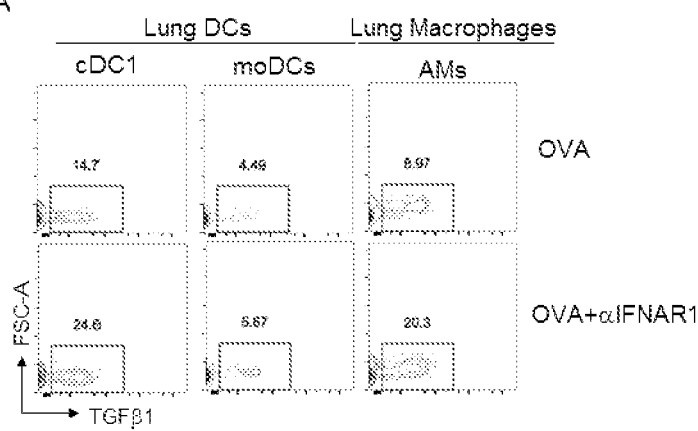

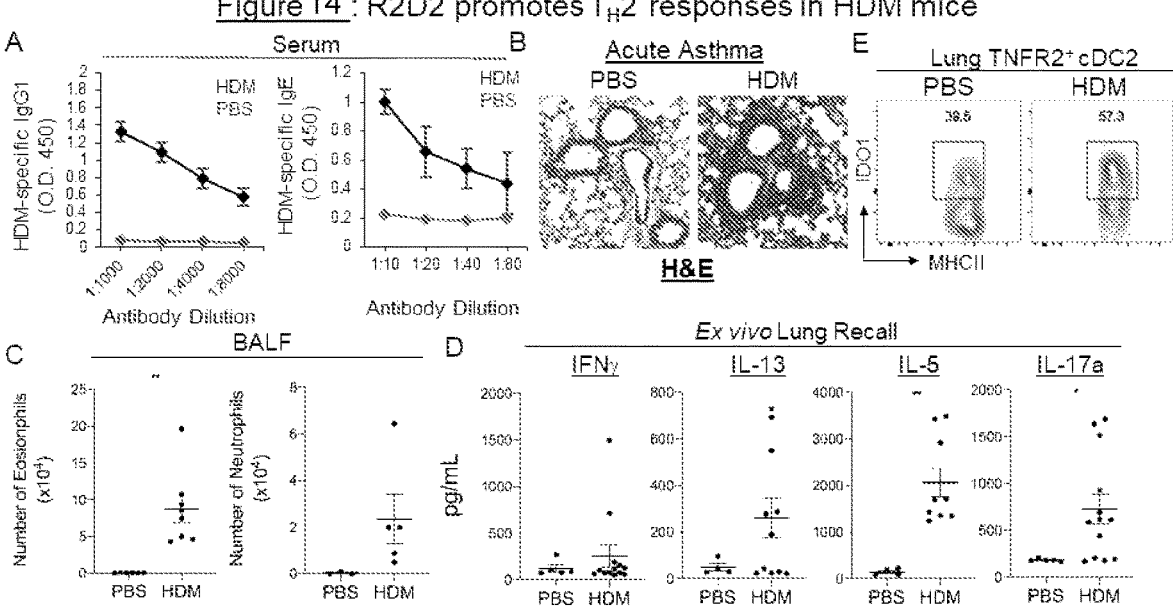
Figure 14 : R2D2 promotes T$_H$2 responses in HDM mice

Figure 15 : Gating strategy for human lung dendritic cells
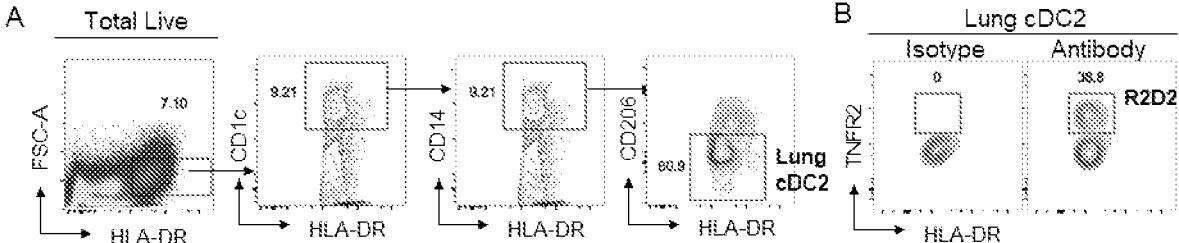

FIG. 16

SEQ ID NO. 1 (human interferon Beta cDNA)

```
    1 attctaactg caacctttcg aagcctttgc tctggcacaa caggtagtag gcgacactgt 61 tcgtgttgtc aacatgacca acaagtgtct cctccaaatt gctctcctgt tgtgcttctc 121 cactacagct ctttccatga gctacaactt gcttggattc ctacaaagaa gcagcaattt 181 tcagtgtcag aagctcctgt ggcaattgaa tgggaggctt gaatactgcc tcaaggacag 241 gatgaacttt gacatccctg aggagattaa gcagctgcag cagttccaga aggaggacgc 301 cgcattgacc atctatgaga tgctccagaa catctttgct attttcagac aagattcatc 361 tagcactggc tggaatgaga ctattgttga gaacctcctg gctaatgtct atcatcagat 421 aaaccatctg aagacagtcc tggaagaaaa actggagaaa gaagatttca ccaggggaaa 481 actcatgagc agtctgcacc tgaaaagata ttatgggagg attctgcatt acctgaaggc 541 caaggagtac agtcactgtg cctggaccat agtcagagtg gaaatcctaa ggaacttta 601 cttcattaac agacttacag gttacctccg aaactgaaga tctcctagcc tgtgcctctg 661 ggactggaca attgcttcaa gcattcttca accagcagat gctgtttaag tgactgatgg 721 ctaatgtact gcatatgaaa ggacactaga agattttgaa attttttatta aattatgagt 781 tattttttatt tatttaaatt ttatttttgga aaataaatta tttttggtgc aaaagtcaa
```

SEQ ID NO: 2 (IFN-beta 1a amino acid sequence)

MSYNLLGFLQRSSNFQCQKLLWQLNGRLEYCLKDRMNFDIPEEIKQLQQFQKEDAALTIY

EMLQNIFAIFRQDSSSTGWNETIVENLLANVYHQINHLKTVLEEKLEKEDFTRGKLMSSL

HLKRYYGRILHYLKAKEYSHCAWTIVRVEILRNFYFINRLTGYLRN

SEQ ID NO: 3 (IFN-beta 1b amino acid sequence)

```
    1 MTNKCLLQIA LLLCFSTTAL SMSYNLLGFL QRSSNFQCQK LLWQLNGRLE YCLKDRMNFD

61 IPEEIKQLQQ FQKEDAALTI YEMLQNIFAI FRQDSSSTGW NETIVENLLA NVYHQINHLK

121 TVLEEKLEKE DFTRGKLMSS LHLKRYYGRI LHYLKAKEYS HCAWTIVRVE ILRNFYFINR

181 LTGYLRN
```

Fusion protein of human and mouse IFNBeta and TNF_D219N/A221R

Human TNF Sequence SEQ ID NO: 8

Human IFNB1 Sequence (P01574) SEQ ID NO: 3

SEQ ID NO: 5 (highlighted)

SEQ ID NO: 4 highlighted

Mouse TNF Sequence SEQ ID NO: 10

Mouse IFNB1 Sequence (P01575) SEQ ID NO: 9

SEQ ID NO: 7 highlighted

SEQ ID NO: 6 highlighted

TARGETING LUNG-RESIDENT TNFR2+ CDC2 (R2D2) SUBPOPULATION TO TREAT ASTHMA

STATEMENT OF GOVERNMENT INTEREST

This invention was made with Government support under Grant Nos. R01AI110606 and R21AI125999, awarded by the National Institutes of Health. The Government has certain rights in the invention.

REFERENCE TO ELECTRONIC SEQUENCE LISTING

The application contains a Sequence Listing which has been submitted electronically in .txt format and is hereby incorporated by reference in its entirety. Said .txt copy, created on May 21, 2020 is named "10457413US1_ST25" and is 16,127 bytes in size. The sequence listing contained in this .txt file is part of the specification and is hereby incorporated by reference herein in its entirety.

INTRODUCTION

Acute exacerbation of asthma and chronic asthma are often caused by spasm of the airways, or bronchoconstriction, causing symptoms including sudden shortness of breath, wheezing, and cough. Bronchospasm is treated with inhaled bronchodilators (anticholinergics such as ipratropium and beta-agonists such as albuterol). Patients inhale these medications into their lungs as a mist, produced by either a nebulizer or a hand-held meter dose (MDI) or dry powder (DPI) inhaler. Patients with acute episodes may also be treated with oral or intravenous steroids that serve to reduce the inflammatory response that exacerbates the condition.

Asthma is a chronic respiratory disease characterized by inflammation of the airways, excess mucus production and airway hyperresponsiveness, and a condition in which airways narrow excessively or too easily respond to a stimulus. Asthma episodes or attacks cause narrowing of the airways, which make breathing difficult. Asthma attacks can have a significant impact on a patient's life, limiting participation in many activities. In severe cases, asthma attacks can be life threatening. Presently, there is no known cure for asthma.

According to the American Lung Association, there are approximately 20 million Americans with asthma in 2002. Fourteen million of them were adults. Asthma resulted in approximately 1.9 million emergency room visits in 2002. The estimated direct cost of asthma in the U.S. is $11.5 billion, which is spent on asthma medications, physician office visits, emergency room visits and hospitalizations.

Chronic obstructive pulmonary disease (COPD) is a term used to classify two major airflow obstruction disorders: chronic bronchitis and emphysema. Approximately 16 million Americans have COPD, 80-90% of them were smokers throughout much of their lives. COPD is a leading cause of death in the U.S., accounting for 122,283 deaths in 2003. The cost to the USA for COPD was approximately $20.9 billion in direct health care expenditures in 2003. Chronic bronchitis is inflammation of the bronchial airways. The bronchial airways connect the trachea with the lungs. When inflamed, the bronchial tubes secrete mucus, causing a chronic cough. Emphysema is an over-inflation of the alveoli, or air sacs in the lungs. This condition causes shortness of breath.

BRIEF DESCRIPTION OF THE DRAWINGS

FIG. 1. The lung TNFR2$^+$ cDC2 subset (R2D2) maintains lung tolerance and prevents lung inflammation at steady-state. A. Numbers of lung CD4$^+$ T cells at steady-state in WT, Batf3$^{-/-}$, CCR2$^{-/-}$, and IRF4$^{fl/fl}$CD11c$^{cre}$ mice. Data were compiled from two independent experiments. B. Numbers of lung CD4$^+$ T cells in WT, IRF4$^{fl/fl}$CD11c$^{cre}$, RelBf$^{fl/fl}$CD11c$^{cre}$ and TNFR2$^{fl/fl}$CD11c$^{cre}$ mice at steady-state. Data were representative of two independent experiments. C. Image of mediastinal lymph nodes (top) and spleens (bottom) in of 7- to 8-week-old knockout strains at steady-state. n=3 mice/group. Data are representative of two independent experiments. D. Numbers of CD45$^+$ cells in the lungs (left), mediastinal lymph nodes (center) and spleens (right) in the indicated knockout strains at steady-state. Data were representative of two independent experiments. E. Numbers of CD4$^+$ T cells in IRF4$^{fl/fl}$CD11c$^{cre}$ mice 14 days post cell adoptive transfer. TNFR2$^+$ or TNFR2$^-$ cDC2 were sorted from WT mice lung and intranasally (i.n.) transferred into IRF4$^{fl/fl}$CD11c$^{cre}$ recipient mice. Data are representative of two independent experiments. F. Numbers of lung Foxp3$^+$ CD4$^+$ T-reg cells at steady-state in WT, Batf3$^{-/-}$, CCR2$^{-/-}$, and IRF4$^{fl/fl}$CD11c$^{cre}$ mice. Data were representive of two independent experiments. Graphs represent the mean with error bars indication s.e.m. P values determined by one-way ANOVA Tukey's multiple comparison test. *P<0.05, P<0.001, *P<0.0001.

FIG. 2. Lung-resident Mgl2$^+$/IDO1$^+$ R2D2 population generates T-regs in the lung. A. Flow cytometry plots (left) and quantification (right) of CD4$^+$Foxp3$^+$ T-reg cells in WT, Batf3$^{-/-}$, and IRF4$^{fl/fl}$CD11c$^{cre}$ mice treated with one dose of OVA (1 μg) intranasally (i.n.). Lungs were harvested on day 14. Data are representative of two independent experiments. B-C. Flow cytometry plots (left) and quantification (right) of T-regs in TNFR2$^{fl/fl}$CD11c$^{cre}$ mice (B) and RelB$^{fl/fl}$CD11c$^{cre}$ mice (C) treated with one dose of OVA (1 μg) intranasally (i.n.). Lungs were harvested on day 14. Data are representative of two independent experiments. D. IRF4$^{fl/fl}$CD11c$^{cre}$ mice were adoptively transferred (i.n.) with lung TNFR2$^+$ and TNFR2$^-$ cDC2 from WT mice lung and treated with one dose of OVA (1 μg) i.n. Flow cytometry analysis (left) and quantification (right) of T-regs at day 14. Data are representative of two independent experiments. E-F. Flow cytometry analysis of TNFR2$^+$ cDC2 at steady-state. Data are representative of three independent experiments. n=3 mice/group. G. IRF4$^{fl/fl}$CD11c$^{cre}$ mice were adoptively transferred (i.n.) with lung Mgl2$^+$ TNFR2$^+$ and Mgl2$^-$TNFR2$^+$ cDC2 and treated with one dose of OVA (1 μg) i.n. Flow cytometry analysis (left) and quantification (right) of T-regs at day 14. Data are representative of two independent experiments. Graphs represent the mean with error bars indication s.e.m. P values determined by one-way ANOVA Tukey's multiple comparison test (A,D,G) or unpaired student t-test (B,C). *P<0.05, P<0.001, *P<0.0001.

FIG. 3. Tonic TNFR2 signaling is required for the presence of the R2D2 population in the lung. A-C. Flow cytometry analysis of TNFR2 (A) and pRelB expression (B) on lung cDC2 in TNFR2$^{fl/fl}$ and TNFR2$^{fl/fl}$CD11c$^{cre}$ mice at steady-state. WT mice were treated i.n. with anti-TNFR2 blocking antibody (20 μg) or TNFR2-Fc recombinant protein (2 μg). Lungs were harvested 24 hours later. Data are representative of two independent experiments. D. Quantification of Mgl2$^+$ TNFR2$^+$ cDC2 in the lungs of indicated groups. Data are representative of two independent experiments. E-F. Flow cytometry analysis of TNF expression by anti-TNF mAb (clone D2D4) (E) or mouse TNFR2-Fc recombinant protein (F). n=3 mice/group. Data are representative of three independent experiments. G-H. Flow cytometry analysis of TNFR2$^+$ cDC2 (G) and Ki67 expression (H) in mice treated i.n. with anti-TNFR2 mAb (TR75.89) and TNFR2-agonist TNF$_{D221N/A223R}$ (1 µg). Lungs were harvested 24 hours later. n=3 mice/group. Data are representative of two independent experiments. Graphs represent the mean with error bars indication s.e.m. P values determined by one-way ANOVA Tukey's multiple comparison test (C, D) or unpaired student t-test (G, H). *P<0.05, P<0.001, *P<0.0001.

FIG. 4. IFNβ-IFNAR1 signaling in iR2D2 cells promotes lung T-regs induction. A. Flow cytometry analysis (left) and quantification (right) of lung TNFR2$^+$ cDC2 in WT mice treated i.n. with isotype (20 µg) or anti-IFNAR1 blocking antibody (20 µg). Lungs were harvested 24 hours later. Data are representative of two independent experiments. B. Flow cytometry analysis (left) and quantification (right) of lung T-regs in WT treated i.n. with isotype (20 µg) or anti-IFNAR1 blocking antibody (20 µg) and one dose of OVA (1 µg) i.n. Lungs were harvested on day 14. Data are representative of two independent experiment. C. Flow cytometry analysis of TNFR2$^+$ cDC2 at steady-state. n=3 mice/group. Data are representative of two independent experiments. D. IFNAR1$^{-/-}$ mice were adoptively transferred (i.n.) with lung TNFR2$^+$ cDC2 and one dose of OVA (1 µg) i.n. Flow cytometry analysis of T-regs on day 14. n=3 mice/group. Data are representative of two independent experiment. E. Flow cytometry analysis (left) and numbers (right) of T-regs in mice treated i.n. with OVA (1 µg) or IFNβ (200 ng). Lungs were harvested on day 14. Data are representative of two independent experiments. F. Flow cytometry analysis (left) and absolute numbers (right) of T-regs in IRF4$^{f/}$f' and IRF4$^{fl/fl}$CD11c$^{cre}$ mice treated i.n. with OVA (1 µg) or OVA (1 µg) and IFNβ (200 ng). Lungs were harvested on day 14. Data are representative of two independent experiments. G. Numbers of Mgl2$^+$ TNFR2$^+$ and Mgl2$^-$TNFR2$^+$ cDC2 in mice treated i.n. with PBS or IFNβ (200 ng). n=3 mice/group. Data are representative of two independent experiment. H-I. Flow cytometry analysis of IFNβ expression at steady-state by the anti-IFNβ mAb (clone D2J1 D). n=3 mice/group. Data are representative of two independent experiments. Graphs represent the mean with error bars indication s.e.m. P values determined by one-way ANOVA Tukey's multiple comparison test (F) or unpaired student t-test (A, B, E). *P<0.05, P<0.001, *P<0.0001.

FIG. 5. IFNβ-IFNAR1-TGFβ1 signaling axis in iR2D2 promotes lung T-regs induction. A. Flow cytometry analysis of TNFR2$^+$ cDC2 treated i.n. with PBS or H7N7-HA (1 µg). Lungs were harvested 24 hours later. n=3 mice/group. Data are representative of two independent experiments. B. Flow cytometry analysis (left) and numbers (right) of T-regs in mice treated with PBS, OVA (1 µg)/isotype control, or OVA (1 µg) and anti-TGFβ1 neutralizing antibody (75 µg). Lungs were harvested on day 14. Data are representative of two independent experiments. C. Flow cytometry analysis of TGFβ1 production by TNFR2$^+$ cDC2 in mice treated i.n. with PBS, OVA (1 µg), or OVA (1 µg) and IFNβ (200 ng). Lungs were harvested 24 hours later. n=3 mice/group. Data are representative of three independent experiments. D. Flow cytometry analysis of TGFβ1 production by TNFR2$^+$ cDC2 in mice treated with PBS, OVA (1 µg)/isotype control, or OVA (1 µg) and anti-IFNAR1 blocking antibody (20 µg). Lungs were harvested 24 hours later. Data are representative of two independent experiments. E. Experimental design for adoptive transfer. F-G. IFNAR1$^{-/-}$ mice were adoptively transferred (i.n.) with lung TNFR2$^+$ cDC2 and treated with PBS or IFNβ (200 ng). Flow cytometry analysis of TGFβ1 production by TNFR2$^+$ cDC2 (F) and T-regs (G). Data are representative of two independent experiments. Graphs represent the mean with error bars indication s.e.m. P values determined by unpaired student t-test (B,F,G). *P<0.05, P<0.001, *P<0.0001.

FIG. 6. R2D2 promotes T$_H$2 responses in HDM mice. A. Experimental protocol for HDM-induced acute asthma. B. Flow cytometry analysis (left) and numbers (right) of TNFR2$^+$ cDC2 in PBS or HDM-induced asthmatic WT mice. Data were compiled from two independent experiments. C. Flow cytometry analysis of Mgl2$^+$TNFR2$^+$ cDC2 in PBS or HDM-induced asthmatic WT mice. Data are representative of three independent experiments. D. Flow cytometry analysis of T-regs in OVA (1 µg) treated (left) and HDM-induced asthmatic WT mice (right). n=3 mice/group. Data are representative of three independent experiments. E-F. Flow cytometry analysis of TNFR2$^+$ cDC2 in HDM-induced asthmatic WT mice. n=3mice/group. Data are representative of three independent experiments. G. Experimental design for adoptive transfer (top). Flow cytometry analysis of IL-4 production by lung CD4$^+$ T cells. n=3mice/group. Data are representative of two independent experiments. H. Flow cytometry analysis of R2D2 in OVA (1 µg) treated (left) and HDM-induced asthmatic WT mice (right). n=3 mice/group. Data are representative of three independent experiments. Graphs represent the mean with error bars indication s.e.m. P values determined by unpaired student t-test (B). *P<0.05, P<0.001, *P<0.0001.

FIG. 7. Lung TNFR2$^+$ cDC2 in healthy and lung diseases patients. A. Flow cytometry analysis of pulmonary cDC2 subpopulation in healthy human lungs. Data are representative of eight independent experiments. B. Flow cytometry analysis of TNFR2$^+$cDC2 in donor, emphysema, and chronic rejected human lungs. Data are representative of three independent experiments. C. Frequency of TNFR2$^+$ cDC2 in diseased human lungs. Data were compiled from multiple independent experiments. Graphs represent the mean with error bars indication s.e.m.

FIG. 8. Model—Lung epithelium IFNβ/iR2D2/T-regs axis controls lung tolerance at steady-state.

FIG. 9. Gating strategies for lung DCs subsets. A-B. Gating strategy for lung DCs. cDC1 are MHCII$^{hi}$CD11c$^+$CD11 b$^-$CD64$^-$, moDCs are MHCII$^{hi}$CD11c$^+$CD11b$^+$CD64$^+$, and cDC2 are MHCII$^{hi}$CD11c$^+$CD11b$^+$CD64$^-$. R2D2 are MHCII$^{hi}$CD11c$^+$CD11b$^+$CD64$^-$TNFR2$^+$ and further characterized based by Mgl2 expression. C. Flow cytometry analysis of pRelB expression in lung DCs. D. Flow cytometry analysis of GFP-expression in RelB$^{f/f/}$fCD11c$^{cre}$ mice at steady-state. E. Histograph of IRF4 expression in IRF4$^{f/f}$ and IRF4$^{f/f}$CD11c$^{cre}$ mice at steady-state. n=4 mice/group. Data are representative of three independent experiment. F. Histograph of TNFR2 expression in TNFR2$^{f/f}$ and TNFR2$^{f/f}$CD11c$^{cre}$ mice at steady-state. n=3mice/group. Data are representative of three independent experiment. G. Experimental scheme for the adoptive transfer of TNFR2$^+$ and TNFR2$^-$ cDC2 into IRF4$^{f/f}$CD11c$^{cre}$ mice. H-I. A total of 500,000 CFSE-labelled TNFR2$^+$ or TNFR2$^-$ cDC2s were transferred into recipient mice. Phenotypic analysis of CFSE-labelled lung cDC2 transferred into IRF4$^{f/f}$CD11c$^{cre}$ mice 24 hours post transfer. n=3mice/group. Data are representative of three independent experiment. Graphs represent the mean with error bars indication s.e.m. P values determined by unpaired student t-test.

FIG. 10. Innocuous inhaled protein antigens induce peripheral T-regs in the lung. A. Numbers of CD4$^+$Foxp3$^+$ T-regs cells in WT mice treated with one dose (1 µg) of OVA, PspA, H7N7-HA, or H1N1-NP. Lungs were harvested on day 14. Data were compiled from two independent experiments. B. Flow cytometry analysis of antigen-specific CD4$^+$ T-regs in the lungs of WT mice treated with PBS or OVA (1 µg) i.n. Cells were first gated on CD4$^+$ T cells. n=3mice/group. Data were representative of two independent experiments. C. Flow cytometry analysis of neuropilin-1 expression on lung and dLNs T-regs. n=3 mice/group. Data were representative of two independent experiments. D. Representative histograph showing IL-10-GFP expression in mice treated with PBS or HA (1 µg). n=3 mice/group. Data were representative of two independent experiments. E. Naïve CD4$^+$Foxp3$^-$ T cells were sorted from the spleen of CD45.1$^+$ mice. Cells were transferred into WT intravenously (i.v.). Recipient mice were treated with PBS or OVA (1 µg) i.n. Lungs were harvested on day 14. n=3 mice/group. Data were representative of two independent experiments. F. Flow cytometry analysis of T-regs in mice treated with OVA (1 µg) i.n. and isotype control or anti-CCR7 (20 µg). n=3 mice/group. Data were representative of two independent experiments. G. Flow cytometry plots of T-regs in WT, TNFR1$^{-/-}$ and CCR2$^{-/-}$ mice treated with one dose of OVA (1 µg) (i.n.). Lungs were harvested on day 14. n=3 mice/group. Data were representative of two independent experiments. H. Flow cytometry analysis of TNFR2 expression in alveolar macrophage (AM) and DCs from indicated mice. n=3mice/group. Data are representative of two independent experiments. I. Flow cytometry analysis of T-regs in TNFR2$^{f/f}$ and TNFR2$^{f/f}$LysM$^{cre}$ mice treated with OVA (1 µg) i.n. n=3 mice/group. Data were representative of two independent experiments. Graphs represent the mean with error bars indication s.e.m. P values determined by ANOVA (A). *P<0.05, P<0.001, *P<0.0001.

FIG. 11. Tonic TNFR2 signaling is required for the maintenance of R2D2. A. Flow cytometry analysis of lung TNFR2$^+$ cDC2 at steady-state in TNFR2$^{fl/fl}$, TNFR2$^{fl/fl}$CD11c$^{cre}$ and TNFR2$^{fl/fl}$Lysm$^{cre}$ mice. B. Flow cytometry analysis of TNFR2 expression on lung DCs in TNFR2$^{fl/fl}$ and TNFR2$^{fl/fl}$CD11c$^{cre}$ mice at steady-state. C. Flow cytometry analysis of T-regs in mice treated i.n. with OVA (1 µg) and isotype antibody (20 µg) or anti-TNFR2 blocking antibody (20 µg). Lungs were harvested on day 14. n=3 mice/group. Data are representative of two independent experiments. D. Flow cytometry analysis of Ki67 expression in lung cDC1 from mice treated i.n. with anti-TNFR2 mAb (TR75.89) and TNFR2-agonist TNF$_{D221N/A223R}$ (1 µg). Lungs were harvested 24 hours later. n=3 mice/group. Data are representative of two independent experiments. Graphs represent the mean with error bars indication s.e.m. P values determined by unpaired student t-test (C). *P<0.05, P<0.001, *P<0.0001.

FIG. 12. IFNβ-IFNAR1 signaling in iR2D2 cells promotes lung T-regs induction. A. Flow cytometry analysis of IDO1 expression in TNFR2$^+$ cDC2 in mice treated i.n. with isotype (20 µg) or anti-IFNAR1 blocking antibody (20 µg). Lungs were harvested 24 hours later. n=3mice/group. Data are representative of two independent experiments. B. Flow cytometry analysis of TNFR2$^+$ cDC2 (left) and Mgl2$^+$ TNFR2$^+$ cDC2 (right) in WT and IFNAR1$^{-/-}$ mice at steady-state. n=3mice/group. Data are representative of three independent experiments. C-D. Flow cytometry analysis of IFNAR1 expression in lung DCs. n=3mice/group. Data are representative of two independent experiments. E. Flow cytometry analysis of pSTAT1 (Y701) (clone 58D6) expression in TNFR2$^+$ cDC2 in mice treated i.n. with IFNβ (200 ng), anti-IFNAR1 blocking antibody (20 µg). Lungs were harvested 24 hours later. n=3mice/group. Data are representative of three independent experiments.

FIG. 13. IFNβ-IFNAR1-TGFβ1 signaling axis in iR2D2 promotes lung T-regs induction. A. Flow cytometry analysis of TGFβ1 expression in lung DCs and alveolar macrophages in WT mice treated with OVA (1 µg) or anti-IFNAR1 blocking antibody (20 µg). Lungs were harvested 24 hours later. n=3mice/group. Data are representative of two independent experiments.

FIG. 14. iR2D2 promotes T$_H$2 responses in HDM mice. A. Serum levels of HDM-specific IgG1 (left) and IgE from HDM-induced asthmatic mice. n=3 mice/group. Data are representative of four independent experiments. B. Representative haematoxylin and eosin (H&E) staining of lung sections of HDM-induced asthmatic mice. n=3mice/group. Data are representative of four independent experiments. C. Number of eosinophils (left) and neutrophils (right) in the BALF of HDM-induced asthmatic mice. Data were compiled two independent experiments. D. Lung samples from HDM-induced asthmatic mice were restimulated ex-vivo for 4 days with HDM (25 µg/ml). Cytokines were measured using ELISA. Data were compiled from two independent experiments. E. Flow cytometry analysis of IDO1-expression on TNFR2$^+$ cDC2 in HDM-induced asthmatic WT mice. n=3 mice/group. Data are representative of three independent experiment. Graphs represent the mean with error bars indication s.e.m. P values determined by unpaired student t-test (C). *P<0.05, P<0.001, *P<0.0001.

FIG. 15. Gating strategy for human lung dendritic cells. A. Human lung cDC2 are HLA-DR$^+$CD1c$^+$CD14$^-$CD206$^-$. B. Flow cytometry analysis of TNFR2$^+$ cDC2 in healthy human lung.

FIG. 16 shows examples of sequences relating to IFN-β sequences.

Figure 17:
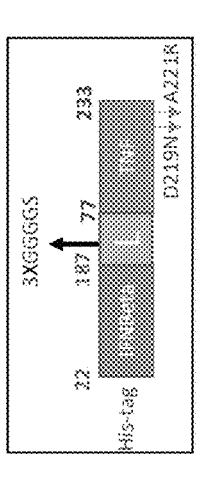
FIG. 17 shows IFN-TNF fusion peptides and sequences thereof. The full human IFNB1 sequence (SEQ ID No. 3, FIG. 16) is shown and the highlighted portion (SEQ ID NO. 4) is shown being implemented with the fusion peptide. The full human TNF sequence (SEQ ID NO. 8) is shown with the highlighted portion (SEQ ID NO. 5) being implemented with the fusion peptide. Also shown is the full mouse IFNB1 sequence (SEQ ID NO. 9) and the highlighted portion (SEQ ID NO. 6) as well as the full mouse TNF sequence (SEQ ID NO. 10) and the highlighted portion (SEQ ID NO. 7). The highlighted IFNB1 segment (SEQ ID NO. 6) and highlighted TNF segment (SEQ ID NO. 7) are shown being implemented with a IFN-TNF fusion peptide.

The details of one or more embodiments of the invention are set forth in the accompanying drawings and the description below. Other features, objects, and advantages of the invention will be apparent from the description and drawings, and from the claims.

DETAILED DESCRIPTION

Overview

Asthma is a chronic disease that inflames and narrows the airway of lungs and makes breathing difficult. There are more than 3 million cases of asthma each year in U.S. Here, disclosed is a new therapy to treat asthma based on a novel in vivo mechanism controlling lung T-regulatory cells (Tregs) induction. Specifically, the disclosure is based on two new discoveries. First, it was found that the new lung-resident Mgl2+IDO-1+Arginase-1+pRelB+TNFR2+ conventional DC2 subpopulation (R2D2, see FIG. 15) controls lung T-regulatory cell production. Second, it was found that IFNβ-IFNAR1 signaling in R2D2 controls its ability to induce lung T regulatory cells. See Mansouri S, Katikaneni D S, Gogoi H, Pipkin M, Machuca T N, Emtiazjoo A M and Jin I, *Mucosal Immunol.* 2020 Jan. 20. doi: 10.1038/s41385-020-0254-1. Based on these mechanistic insights, a new strategy was developed involving the use of intranasal administrated IFNβ and R2D2-targeted IFNβ-TNFmut fusion protein to promote lung T-regulatory cells induction and prevent and treat asthma.

As described herein, the inventors identified a lung IFNAR1^{hi}TNFR2^+ cDC2 population (iR2D2) as the tolerogenic DC generating antigen-specific lung T-regs and preventing lung inflammation at steady-state. Our conclusion is based exclusively on studies in the lung in vivo. Our conclusion is different from previous reports suggesting pDCs (de Heer H J, Hammad H, Soullie T, Hijdra D, Vos N, Willart M A et al. Essential role of lung plasmacytoid dendritic cells in preventing asthmatic reactions to harmless inhaled antigen. *J Exp Med* 2004; 200(1): 89-98), cDC1 (Khare A, Krishnamoorthy N, Oriss T B, Fei M, Ray P, Ray A. Cutting edge: inhaled antigen upregulates retinaldehyde dehydrogenase in lung CD103+ but not plasmacytoid dendritic cells to induce Foxp3 de novo in CD4+ T cells and promote airway tolerance. *J Immunol* 2013; 191(1): 25-29) or macrophage (Soroosh P, Doherty T A, Duan W, Mehta A K, Choi H, Adams Y F et al. Lung-resident tissue macrophages generate Foxp3+ regulatory T cells and promote airway tolerance. *J Exp Med* 2013; 210(4): 775-788) induces T-regs in the lung. We showed that mice lacking the iR2D2 population by gene ablation or antibody depletion failed to generate lung T-regs while intranasal administration of IFNβ induced R2D2-dependent lung T-regs. It is noteworthy that lung R2D2 cells, including iR2D2 depend on the constitutive TNFR2 signaling. R2D2 can't survive in the ex vivo cells co-culture system, which was used by the previous investigations.

The lung iR2D2 population is plastic. iR2D2 is a subpopulation of cDC2. Previous studies established that cDC2 mediates T_H2, T_H17 responses. We also showed that R2D2 promotes T_H responses of the mucosal adjuvant cyclic di-GMP in vivo. We propose that DCs at the barrier surface, influenced by their microenvironment, are plastic inducing T-regs, maintaining peripheral tolerance at the steady-state but promoting immunogenic responses during pathogenic conditions.

The tolerogenic iR2D2 population is a product of two constitutive signals from its microenvironment: IFNβ-IFNAR1 and tmTNF-TNFR2. Using a TNFR2 agonist, we showed that TNFR2 signaling promoted R2D2 proliferation. TNFR2 expression defines a highly immunosuppressive T-regs found in tumor microenvironment promoting cancer cell survival and tumor growth [37, 38]. Similar to our R2D2 cells, TNFR2 activation stimulates the proliferation of TNFR2^+ Tregs [39]. Antagonistic antibodies against human TNFR2 inhibited TNFR2^+ T-regs proliferation[39]. The underlying molecular mechanism of TNFR2 signaling induced cell proliferation is unknown. Elucidating the TNFR2 signaling responsible for maintaining this R2D2 population in the lung is a future priority.

R2D2 cells with active IFNAR1 signaling become iR2D2. iR2D2 intrinsic IFNβ signaling is necessary and sufficient for lung T-regs induction via the production of TGFβ1. However, the molecular pathway by which IFNβ-IFNAR1 signaling leading to TGFβ1 production is unknown. IFNβ has an immunomodulatory effect (Kasper L H, Reder A T.

Immunomodulatory activity of interferon-beta. *Ann Clin Transl Neurol* 2014; 1(8): 622-631). In the clinic, IFNβ (Avonex®, Rebif®) has been used to treat relapsed Multiple Sclerosis for over 20 years. Nevertheless, the in vivo mechanism and targeted cells of IFNβ treatment remain poorly defined (Kasper et al. 2014, supra). We propose that lung R2D2 or R2D2-like cells in other peripheral organs are the effector cells for the immunomodulatory function of IFNβ in vivo. Noteworthy, IFNα is not approved for Multiple Sclerosis. Future studies should also determine if IFNβ activates a unique IFNAR1 signaling in iR2D2 cells to control the tolerogenic program at steady-state.

Lung epithelial cells are a major source of tmTNF and the sole producer of lung IFNβ at the steady-state. Impaired bronchial epithelial cells (BECs) IFNβ production has been well-documented in asthmatic patients (Baraldo S, Saetta M, Barbato A, Contoli M, Papi A. Rhinovirus-induced interferon production in asthma. *Thorax* 2014; 69(8): 772). We thus introduce a new paradigm that at steady-state, lung epithelial cells express tmTNF to keep R2D2 alive and continuously secret IFNβ to condition R2D2 to generate lung T-regs and prevent lung inflammation (FIG. 8). Different from the current lung-epithelial cells-DCs-T_H2 axis during inflammation (Deckers J, De Bosscher K, Lambrecht B N, Hammad H. Interplay between barrier epithelial cells and dendritic cells in allergic sensitization through the lung and the skin. *Immunol Rev* 2017; 278(1): 131-144), the lung epithelial cells IFNβ-iR2D2-T-regs axis here is tolerogenic and needed to be constitutively active. Loss of tmTNF or IFNβ will result in the loss of iR2D2 and lung mucosal tolerance. Indeed, BECs from asthma patients are biased towards higher TSLP and lower IFNβ production (Uller L, Leino M, Bedke N, Sammut D, Green B, Lau L et al. Double-stranded RNA induces disproportionate expression of thymic stromal lymphopoietin versus interferon-beta in bronchial epithelial cells from donors with asthma. *Thorax* 2010; 65(7): 626-632).

The plasticity of R2D2 cells makes them an ideal immunotherapy target for chronic inflammatory diseases. We showed that IFNβ administration could enhance lung T-regs induction. A phase II clinical trial of inhaled IFNβ for virus-induced asthma exacerbation showed promising results (clinicaltrials.gov, identifier NCT 01126177) (Djukanovic R, Harrison T, Johnston S L, Gabbay F, Wark P, Thomson N C et al. The effect of inhaled IFN-beta on worsening of asthma symptoms caused by viral infections. A randomized trial. *Am J Respir Crit Care Med* 2014; 190(2): 145-154. Jackson D J. Inhaled interferon: a novel treatment for virus-induced asthma? *Am J Respir Crit Care Med* 2014; 190(2): 123-124). Translationally, targeting IFNβ directly to R2D2 will limit the toxicity of IFNβ and improve its efficacy. On the other hand, for studies exploring the therapeutic potential of ex vivo generated tolerogenic DCs, caution should be taken. Due to the plasticity of tolerogenic DCs, these ex vivo generated tolerogenic DCs maybe plastic and could be re-conditioned by the inflammatory milieu and become immunogenic in vivo.

In summary, we identified iR2D2 as the tolerogenic lung DC population and surprisingly found it is plastic. This newly discovered DC plasticity can lead to novel anti-inflammatory therapy for lung diseases.

Definitions

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The term "asthma" as used herein may pertain to an exacerbation of asthma, intermittent asthma or chronic asthma.

The term "inflammatory respiratory disorder" as used herein includes asthma and chronic obstructive pulmonary disease (COPD).

The term "interferon-beta", "interferonβ," "IFNB" and "IFN-β" as used interchangeably herein to refer to any form or analog of IFN-β that retains the biological activity of native IFN-β and preferably retains the activity of IFN-β that is present in the lung and, in particular, the bronchial and/or alveolar epithelium. The IFN-β may be identical to or comprise the sequence of human IFN-β1a (SEQ ID NO: 2) or human IFN-β1b (SEQ ID NO: 3), or fragments thereof.

The term "interferon-beta related agent" "IFN-β related agent" or "IFNB related agent" are used interchangeable herein and are construed to include IFNB, IFNB conjugates and fusion proteins, and agents that increase IFN-β expression as further described herein.

The term "IFN-TNF fusion protein" as used herein refers to a IFNB fusion protein comprising an amino acid sequence encoding IFN-β, a fragment thereof, or a variant thereof having at least 90% or 95% identity with IFN-β or fragment thereof, linked to an amino acid sequence encoding TNF, a fragment thereof or a variant thereof having at least 90% or 95% identity with TNF or fragment thereof. In a specific embodiment, the IFN-β portion is linked to the TNF portion via an amino acid sequence comprising at least 5 amino acids. Typically, the linker is 5-30 amino acids long. FIG. 17 sets forth examples of fusion proteins that pertain to human and mouse IFN-β and TNF sequences. SEQ ID NO. 4 pertains to the highlighted segment of the human IFN-β sequence. SEQ ID NO. 5 pertains to the highlighted segment of the human TNF sequence. Thus, a specific example of an IFN-TNF fusion protein refers to SEQ ID NO. 4, fragment thereof, or variant having at least 90% or 95% identity therewith linked to SEQ ID NO. 5, or fragment thereof, or variant having at least 90% or 95% identity therewith. In an even more specific embodiment, the fusion protein pertains to SEQ ID NO. 4 linked with SEQ ID NO. 5. An example of a linker sequence is provided in FIG. 17 and pertains to a repeat of GGGGS (e.g. 3×GGGGS). FIG. 17 also sets forth a mouse IFN-TNF fusion protein example. SEQ ID NO. 6 pertains to the highlighted segment of the mouse IFN-β sequence and SEQ ID NO. 7 pertains to the highlighted segment of the mouse TNF sequence. A specific example of a mouse IFN-TNF fusion protein is SEQ ID NO. 6, or fragment thereof, or variant comprising at least 90% or 95% identity with SEQ ID NO. 6 or fragment thereof, linked with SEQ ID NO. 7 or fragment thereof, or a variant comprising at least 90% or 95% identity therewith.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The term also includes variants on the traditional peptide linkage joining the amino acids making up the polypeptide. Preferred "peptides", "polypeptides", and "proteins" are chains of amino acids whose alpha carbons are linked through peptide bonds. The terminal amino acid at one end of the chain (amino terminal) therefore has a free amino group, while the terminal amino acid at the other end of the chain (carboxy terminal) has a free carboxyl group. As used herein, the term "amino terminus" (abbreviated N-terminus) refers to the free α-amino group on an amino acid at the amino terminal of a peptide or to the α-amino group (imino group when participating in a peptide bond) of an amino acid at any other location within the peptide. Similarly, the term "carboxy terminus" refers to the free carboxyl group on the carboxy terminus of a peptide or the carboxyl group of an amino acid at any other location within the peptide. Peptides also include essentially any polyamino acid including, but not limited to peptide mimetics such as amino acids joined by an ether as opposed to an amide bond.

As used herein, an "antibody" refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these regions of the light and heavy chains respectively.

Antibodies exist as intact immunoglobulins or as a number of well characterized fragments produced by digestion with various peptidases or expressed de novo. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region thereby converting the (Fab')$_2$ dimer into an Fab' monomer. The Fab' monomer is essentially an Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies, including, but are not limited to, Fab'2, IgG, IgM, IgA, IgE, scFv, dAb, nanobodies, unibodies, and diabodies. In various embodiments preferred antibodies include, but are not limited to Fab'2, IgG, IgM, IgA, IgE, and single chain antibodies, more preferably single chain Fv (scFv) antibodies in which a variable heavy and a variable light chain are joined together (directly or through a peptide linker) to form a continuous polypeptide.

The term "variant" as used herein in the context of an nucleic acid sequence or amino acid sequence that has at least 80% identity to that sequence based on amino acid identity. More preferably, the polypeptide has at least 85% or 90% and more preferably at least 95%, 97% or 99% identity based on amino acid identity to the amino acid sequence. There may be at least 80%, for example at least 85%, 90% or 95%, amino acid identity over a stretch of 40 or more, for example 60, 80, 100, 120, 140 or 160 or more, contiguous amino acids ("hard homology").

The term "fragment" as used in the context of amino acid sequences refers to seqgment of contiguous amino acid residues of a given amino acid sequence. Fragments may be at least from 80, 100, 120, 130, or 140 amino acids in length, or greater. Such fragments may be used to produce chimeric agents as described in more detail below.

The term "a subject in need" refers to a human or non-human mammal that exhibits one or more symptoms of an inflammatory respiratory disorder.
Sequences Sequence information is provided in FIG. 16 and FIG. 17, as well as the attendant sequence listing. For the purposes of comparing two closely-related polypeptide or polynucleotide sequences, the "% sequence identity" (or "% identity", used interchangeably herein) between a first sequence and a second sequence may be calculated. Polypeptide or polynucleotide sequences are said to be the same as or identical to other polypeptide or polynucleotide sequences, if they share 100% sequence identity over their entire length. Residues in sequences are numbered from left to right, i.e. from N- to C-terminus for polypeptides; from 5' to 3' terminus for polynucleotides. The terms "identical" or percentage "identity", in the context of two or more polypeptide sequences, refer to two or more sequences or sub-sequences that are the same or have a specified percentage of amino acid residues that are the same (i.e., 70% identity, optionally 75%, 80%, 85%, 90%, 95%, 98% or 99% identity over a specified region), when compared and aligned for maximum correspondence over a comparison window, or designated region as measured using one of the following sequence comparison algorithms or by manual alignment and visual inspection. This definition also refers to the compliment of a test sequence. Optionally, the identity exists over a region that is at least 250 amino acids in length, such as 300 amino acids or 350 amino acids. Suitably, the comparison is performed over a window corresponding to the entire length of the reference sequence (as opposed to the derivative sequence).

For sequence comparison, one sequence acts as the reference sequence, to which the test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percentage sequence identities for the test sequences relative to the reference sequence, based on the program parameters.

A "comparison window", as used herein, refers to a segment in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman 1981, by the homology alignment algorithm of Needleman & Wunsch 1970, by the search for similarity method of Pearson & Lipman 1988, by computerised implementations of these algorithms (GAP, BEST- FIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al. 1995).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle 1987. The method used is similar to the method described by Higgins & Sharp 1989. The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al. 1984).

Another example of algorithm that is suitable for determining percent sequence identity and sequence similarity are the BLAST and BLAST 2.0 algorithms, which are described in Altschul et al. 1977 and Altschul et al. 1990, respectively. Software for performing BLAST analyses is publicly available through the National Center for Biotechnology Information (website at www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighbourhood word score threshold (Altschul et al., supra). These initial neighbourhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff &

15

Henikoff 1989) alignments (B) of 50, expectation (E) of 10, M=5, N=−4, and a comparison of both strands.

The BLAST algorithm also performs a statistical analysis of the similarity between two sequences (see, e.g., Karlin & Altschul 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

A "difference" between sequences refers to an insertion, deletion or substitution of a single residue in a position of the second sequence, compared to the first sequence. Two sequences can contain one, two or more such differences. Insertions, deletions or substitutions in a second sequence which is otherwise identical (100% sequence identity) to a first sequence result in reduced % sequence identity. For example, if the identical sequences are 9 residues long, one substitution in the second sequence results in a sequence identity of 88.9%. If the identical sequences are 17 amino acid residues long, two substitutions in the second sequence results in a sequence identity of 88.2%.

Alternatively, for the purposes of comparing a first, reference sequence to a second, comparison sequence, the number of additions, substitutions and/or deletions made to the first sequence to produce the second sequence may be ascertained. An addition is the addition of one residue into the first sequence (including addition at either terminus of the first sequence). A substitution is the substitution of one residue in the first sequence with one different residue. A deletion is the deletion of one residue from the first sequence (including deletion at either terminus of the first sequence). Suitably, a substitution may be conservative. A 'conservative' substitution is an amino acid substitution in which an amino acid residue is replaced with another amino acid residue of similar chemical structure and which is expected to have little influence on the function, activity or other biological properties of the polypeptide. Such conservative substitutions suitably are substitutions in which one amino acid within the following groups is substituted by another amino acid residue from within the same group:

| Group | Amino acid residue |
| --- | --- |
| Non-polar aliphatic | Glycine |
| | Alanine |
| | Valine |
| | Leucine |
| | Isoleucine |
| Aromatic | Phenylalanine |
| | Tyrosine |
| | Tryptophan |
| Polar uncharged | Serine |
| | Methionine |
| | Cysteine |
| | Threonine |
| | Asparagine |
| | Glutamine |
| Negatively charged | Aspartate |
| | Glutamate |
| Positively charged | Lysine |
| | Arginine |
| | Histidine |

16

Interferon-Beta

IFNB as defined in SEQ ID NOs: 2 and 3 may be administered in therapeutically effective amounts via an appropriate mode of administration. In addition to the native sequences, variants retaining the biological function of IFNB may be administered as well. Accordingly, IFN-β also refers to a variant polypeptide having an amino acid sequence which varies from that of SEQ ID NO: 2 or 3. Alternatively, IFN-β may be chemically-modified.

A variant of IFN-β may be a naturally occurring variant, for example a variant which is expressed by a non-human species. Also, variants of IFN-β include sequences which vary from SEQ ID NO: 2 or 3 but are not necessarily naturally occurring. Over the entire length of the amino acid sequence of SEQ ID NO: 2 or 3, a variant will preferably comprise at least 80% identity to that sequence based on amino acid identity. More preferably, the polypeptide has at least 85% or 90% and more preferably at least 95%, 97% or 99% identity to the amino acid sequence of SEQ ID NO: 2 or 3 over the entire sequence, or to a fragment thereof. There may be at least 80%, for example at least 85%, 90% or 95%, amino acid identity over a stretch of 40 or more, for example 60, 80, 100, 120, 140 or 160 or more, contiguous amino acids ("hard homology").

One or more amino acid residues of the amino acid sequence of SEQ ID NO: 2 or 3 may alternatively or additionally be deleted. From 1, 2, 3, 4 or 5 to 10, 20 or 30 residues may be deleted, or more. IFN-β also includes fragments of the above-mentioned sequences. Such fragments retain IFN-β activity. Fragments may be at least from 120, 130, or 140 amino acids in length. Such fragments may be used to produce chimeric agents as described in more detail below.

IFN-β includes chimeric proteins comprising fragments or portions of SEQ ID NO: 2 or 3. One or more amino acids may be alternatively or additionally added to the polypeptides described above. An extension may be provided at the N-terminus or C-terminus of the amino acid sequence of SEQ ID NO: 2 or 3, or polypeptide variant or fragment thereof. The extension may be quite short, for example from 1 to 10 amino acids in length. Alternatively, the extension may be longer. A carrier protein may be fused to an amino acid sequence described above. A fusion protein incorporating one of the polypeptides described above can thus be used in the invention.

IFN-β also includes SEQ ID NO: 2 or 3 or variants thereof that have been chemically-modified. A number of side chain modifications are known in the art and may be made to the side chains of the proteins or peptides discussed above. Such modifications include, for example, glycosylation, phosphorylation, modifications of amino acids by reductive alkylation by reaction with an aldehyde followed by reduction with $NaBH_4$, amidation with methylacetimidate or acylation with acetic anhydride. The modification is preferably glycosylation. The IFN-β may be made synthetically or by recombinant means using methods known in the art. The amino acid sequence of proteins and polypeptides may be modified to include non-naturally occurring amino acids or to increase the stability of the compound. When the proteins or peptides are produced by synthetic means, such amino acids may be introduced during production. The proteins or peptides may also be modified following either synthetic or recombinant production. The IFN-β may also be produced using D-amino acids. In such cases the amino acids will be linked in reverse sequence in the C to N orientation. This is conventional in the art for producing such proteins or peptides.

The IFN-β may be produced in a cell by in situ expression of the polypeptide from a recombinant expression vector. The expression vector optionally carries an inducible promoter to control the expression of the polypeptide. The IFN-β or analog thereof may be produced in large scale following purification by any protein liquid chromatography system after recombinant expression. Preferred protein liquid chromatography systems include FPLC, AKTA systems, the Bio-Cad system, the Bio-RadBioLogic system and the Gilson HPLC system. Commercially available forms of IFN-β or analogs thereof may be used in the invention. Examples include Betaseron® and Avonex®.

IFNB Fusion Proteins

In various embodiments, this disclosure pertains to the discovery that attaching an interferon to a targeting moiety (e.g., a molecule that specifically and/or preferentially binds a marker on or associated with a cell) substantially improves the therapeutic efficacy of the interferon and appears to reduce systemic toxicity. Accordingly, certain embodiments pertain to constructs comprising IFNB attached to a targeting moiety and uses of such constructs to specifically and/or preferentially target R2D2 cells. Accordingly, in certain embodiments, a chimeric construct is provided where the construct comprises IFNB attached to a targeting moiety that binds to TNFR2, where the construct when contacted to a R2D2 cells promotes induction of lung T-regulatory cells. In certain embodiments the targeting moiety is chemically coupled to the IFNB. In certain embodiments the targeting moiety is joined to IFNB with a peptide linker. In certain embodiments the peptide linker is fewer than 15, fewer than 14, fewer than 12, fewer than 11, fewer than 10, fewer than 9, fewer than 8, fewer than 7, fewer than 6, fewer than 5, fewer than 4, fewer than 3, or fewer than 2 amino acids in length. In certain embodiments the linker is 15, 14, 13, 12, 11, 10, 9, 8, 7, 6, 5, 4, 3, 2, or 1 amino acid in length. In certain embodiments the linker is not (Gly₄Ser)₃ (See U.S. Pat. No. 8,258,263 ('263 patent) incorporated herein in its entirety). In certain embodiments the linker is a linker that is resistant or substantially resistant to proteolysis. In certain embodiments the peptide linker is Gly₄Ser. In certain embodiments the linker comprises or consists of an amino acid sequence found in Table 4 of the '263 patent. In certain embodiments the construct is a recombinantly expressed fusion protein. In certain embodiments the targeting moiety is an Anti-TNFR2 blocking antibody or an Anti-Mgl2 antibody.

Generally speaking, the targeting moiety (e.g., Anti-TNFR2 or anti-Mgl2) can be joined together in any order. Thus, for example, the antibody can be joined to either the amino or carboxy terminal of IFNB. The antibody can also be joined to an internal region of IFNB, or conversely, IFNB can be joined to an internal location or to any terminus of the antibody, as long as the attachment does not interfere with binding of the antibody to its target.

The antibody and IFNB can be attached by any of a number of means well known to those of skill in the art. In certain embodiments, IFNB is conjugated, either directly or through a linker (spacer), to the antibody. In certain embodiments, however, it is preferable to recombinantly express the chimeric moiety as a fusion protein.

In certain embodiments, the targeting moiety (e.g., Anti-TNFR2 or anti-Mgl2) is chemically conjugated to IFNB. Means of chemically conjugating molecules are well known to those of skill. The procedure for conjugating two molecules varies according to the chemical structure of the agent. Polypeptides typically contain variety of functional groups; e.g., carboxylic acid (COOH) or free amine (—NH₂)

groups, that are available for reaction with a suitable functional group on the other peptide, or on a linker to join the molecules thereto. Alternatively, the antibody and/or IFNB can be derivatized to expose or attach additional reactive functional groups. The derivatization can involve attachment of any of a number of linker molecules such as those available from Pierce Chemical Company, Rockford Ill.

A "linker", as used herein, typically refers to a molecule that is used to join the antibody to the interferon. In various embodiments, the linker is capable of forming covalent bonds to both the antibody and to the interferon. Suitable linkers are well known to those of skill in the art and include, but are not limited to, straight or branched-chain carbon linkers, heterocyclic carbon linkers, or peptide linkers. In certain embodiments, the linker(s) can be joined to the constituent amino acids of the antibody and/or the interferon through their side groups (e.g., through a disulfide linkage to cysteine). In certain preferred embodiments, the linkers are joined to the alpha carbon amino and/or carboxyl groups of the terminal amino acids of the antibody and/or the interferon.

A bifunctional linker having one functional group reactive with a group on the antibody and another group reactive on the interferon, can be used to form the desired conjugate. Alternatively, derivatization can involve chemical treatment of the targeting moiety. Procedures for generation of, for example, free sulfhydryl groups on polypeptides, such as antibodies or antibody fragments, are known (See U.S. Pat. No. 4,659,839).

Many procedures and linker molecules for attachment of various compounds including radionuclide metal chelates, toxins and drugs to proteins such as antibodies are known. See, for example, European Patent Application No. 188,256; U.S. Pat. Nos. 4,671,958, 4,659,839, 4,414,148, 4,699,784; 4,680,338; 4,569,789; and 4,589,071; and Borlinghaus et al. (1987) *Cancer Res.* 47: 4071-4075. In particular, production of various immunotoxins is well-known within the art and can be found, for example in "Monoclonal Antibody-Toxin Conjugates: Aiming the Magic Bullet," Thorpe et al., *Monoclonal Antibodies in Clinical Medicine*, Academic Press, pp. 168-190 (1982); Waldmann (1991) Science, 252: 1657; U.S. Pat. Nos. 4,545,985 and 4,894,443, and the like.

In certain embodiments, a chimeric targeting moiety-interferon fusion protein is synthesized using recombinant DNA methodology. Generally this involves creating a DNA sequence that encodes the fusion protein, placing the DNA in an expression cassette under the control of a particular promoter, expressing the protein in a host, isolating the expressed protein and, if required, renaturing the protein. DNA encoding the fusion proteins (e.g., Anti-TNFR2 or anti-Mgl2) described herein can be prepared by any suitable method, including, for example, cloning and restriction of appropriate sequences or direct chemical synthesis by methods such as the phosphotriester method of Narang et al. (1979) *Meth. Enzymol.* 68: 90-99; the phosphodiester method of Brown et al. (1979) *Meth. Enzymol.* 68: 109-151; the diethylphosphoramidite method of Beaucage et al. (1981) *Tetra. Lett.,* 22: 1859-1862); the solid support method of U.S. Pat. No. 4,458,066, and the like.

Chemical synthesis produces a single stranded oligonucleotide. This can be converted into double stranded DNA by hybridization with a complementary sequence or by polymerization with a DNA polymerase using the single strand as a template. One of skill would recognize that while chemical synthesis of DNA is limited to sequences of about 100 bases, longer sequences may be obtained by the ligation of shorter sequences.

Alternatively, subsequences can be cloned and the appropriate subsequences cleaved using appropriate restriction enzymes. The fragments can then be ligated to produce the desired DNA sequence.

In certain embodiments, DNA encoding fusion proteins of the present invention can be cloned using DNA amplification methods such as polymerase chain reaction (PCR). Thus, for example, the gene for IFNB is PCR amplified, using a sense primer containing the restriction site for, e.g., NdeI and an antisense primer containing the restriction site for HindIII. This can produce a nucleic acid encoding the mature interferon sequence and having terminal restriction sites. An antibody having "complementary" restriction sites can similarly be cloned and then ligated to the interferon and/or to a linker attached to the interferon. Ligation of the nucleic acid sequences and insertion into a vector produces a vector encoding the interferon joined to the antibody.

While the two molecules can be directly joined together, one of skill will appreciate that the molecules can be separated by a peptide spacer consisting of one or more amino acids. Generally, the spacer will have no specific biological activity other than to join the proteins or to preserve some minimum distance or other spatial relationship between them. In certain embodiments, however, the constituent amino acids of the spacer can be selected to influence some property of the molecule such as the folding, net charge, or hydrophobicity.

According to a specific example, the IFNB fusion protein comprises an IFN-TNF fusion protein. In a specific embodiment, the fusion protein includes SEQ ID NO. 4, fragment thereof, or variant having at least 90% or 95% identity therewith linked to SEQ ID NO. 5, or fragment thereof, or variant having at least 90% or 95% identity therewith. In an event more specific embodiment, the fusion protein pertains to SEQ ID NO. 4 linked with SEQ ID NO. 5. An example of a linker sequence is provided in FIG. 17 and pertains to a repeat of GGGGS (e.g. 3×GGGGS). A specific example of a mouse IFN-TNF fusion protein is SEQ ID NO. 6, or fragment thereof, or variant comprising at least 90% or 95% identity with SEQ ID NO. 6 or fragment thereof, linked with SEQ ID NO. 7 or fragment thereof, or a variant comprising at least 90% or 95% identity therewith.

Agents that Increase IFN-β Expression

In addition to administration of IFBN, other related embodiments involve administrating an agent that increases endogenous expression of IFN-β in the lung or preferably the bronchial and/or alveolar epithelium, these include agents that induce expression of endogenous IFNB, expression of heterologous sequence (gene therapy agents), and vectors that harbor IFNB expression constructs. As such, agents that increase IFN-β expression are included as INFB related agents.

The agents may act directly on the promoter or other regulatory sequences of the IFN-β gene. Such agents may act to reduce the constitutive silencing of the IFN-β promoter. Alternatively, the agent may stimulate cells to produce endogenous IFN-β by acting at receptors at the cell surface. Agents that increase endogenous expression of IFN-β of interest in relation to the present invention include, but are not limited to, poly(inosinic acid)-poly(cytidylic acid) (poly(IC)), ANA773, perindopril, BL-20803, Tilorone, ABMP, DRB, Atabrine, 10-carboxy-9acridone, CP-28888, Bropirimine, and Imiquimod.

The embodiments may also involve using a polynucleotide which is capable of expressing IFN-β or an agent that increases endogenous expression of IFN-β in lung airways. Such a polynucleotide may preferably be in the form of a vector capable of directing expression of IFN-β or an agent that induces IFN-β in the bronchial and/or alveolar epithelium. The resulting IFN-β or agent may then have a therapeutic effect ("gene therapy"). The polynucleotide may encode any of the forms of IFN-β discussed above including the variants, fragments and chimeric proteins thereof. The polynucleotide encoding IFN-β may comprise a polynucleotide encoding a human sequence (SEQ ID NO: 2 or 3) or a naturally occurring sequence variant, for example a variant which is expressed by a non-human species. Also, a polynucleotide encoding IFN-β includes sequences that encode variant of SEQ ID NO: 2 or 3 but are not necessarily naturally occurring. Over the entire length of the amino acid sequence of SEQ ID NO: 2 or 3, a variant will preferably have at least 80% identity to that sequence. More preferably, the variant has at least 85% or 90% and more preferably at least 95%, 97% or 99% identity to the amino acid sequences of SEQ ID NO: 2 or 3 over the entire sequence.

The polynucleotides may comprise DNA or RNA but preferably comprise DNA. They may also be polynucleotides which include within them synthetic or modified nucleotides. A number of different types of modification to polynucleotides are known in the art. These include methylphosphate and phosphorothioate backbones, addition of acridine or polylysine chains at the 3' and/or 5' ends of the molecule. For the purposes of the present invention, it is to be understood that the polynucleotides described herein may be modified by any method available in the art. Polynucleotides such as a DNA polynucleotide may be produced recombinantly, synthetically, or by any means available to those of skill in the art. They may also be cloned by standard techniques. The polynucleotides are typically provided in isolated and/or purified form. Polynucleotides will generally be produced using recombinant means, for example using PCR (polymerase chain reaction) cloning techniques. This will involve making a pair of primers (e.g. of about 15-30 nucleotides) to a region of the required gene which it is desired to clone, bringing the primers into contact with DNA obtained from a suitable cell, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector. Although in general the techniques mentioned herein are well known in the art, reference may be made in particular to Sambrook et al, 1989. As hereinbefore indicated, preferably the polynucleotide is used in an expression vector wherein it is operably linked to a control sequence which is capable of providing for the expression of the coding sequence in the airways of human lung.

Expression vectors for use in accordance with the invention may be any type of vector conventionally employed for gene therapy. It may be a plasmid expression vector administered as naked DNA or complexed with one or more cationic amphiphiles, e.g. one or more cationic lipids, e.g. in the form of DNA/liposomes. A viral vector may alternatively be employed. Vectors for expression of therapeutic proteins in the airways of human lung have previously been described. For example, Published International Application WO 01/91800 (Isis Innovation Limited) describes for such purpose expression vectors including the human ubiquitin C promoter or functional analogues thereof. The human ubiquitin C promoter has been shown to be capable of producing high level protein expression in the airways of mice over many weeks and hence has been proposed as a favoured promoter for use in airway gene therapy for a variety of respiratory diseases. Examples of expression vectors for use in directing transgene expression in airway epithelia have also been described in Chow et al. Proc. Natl. Acad. Sci. USA 1997; 94: 14695-14700. Such expression vectors can be administered via the airways, e.g. into the nasal cavity or trachea.

Compositions and Therapeutic Methods

The IFN-β related agent may be administered in a medicament or pharmaceutical composition suitable for airway delivery which will typically also include a pharmaceutically acceptable excipient. Such an "excipient" generally refers to a substantially inert material that is nontoxic and does not interact with other components of the composition in a deleterious manner. Pharmaceutically acceptable excipients include, but are not limited to, liquids such as water, saline, polyethyleneglycol, hyaluronic acid, glycerol and ethanol. Pharmaceutically acceptable salts can be included therein, for example, mineral acid salts such as hydrochlorides, hydrobromides, phosphates, sulphates, and the like; and the salts of organic acids such as acetates, propionates, malonates, benzoates, and the like. It is also preferred, although not required, that a composition or medicament comprising the therapeutic agent will contain a pharmaceutically acceptable carrier that serves as a stabilizer, particularly for peptide, protein, polynucleotide or other like agents. Examples of suitable carriers that also act as stabilizers for peptides include, without limitation, pharmaceutical grades of dextrose, sucrose, lactose, trehalose, mannitol, sorbitol, inositol, dextran, and the like. Other suitable carriers include, again without limitation, starch, cellulose, sodium or calcium phosphates, citric acid, tartaric acid, glycine, high molecular weight polyethylene glycols (PEGs), and combination thereof. It may also be useful to employ a charged lipid and/or detergent. Suitable charged lipids include, without limitation, phosphatidylcholines (lecithin), and the like. Detergents will typically be a non-ionic, anionic, cationic or amphoteric surfactant. Examples of suitable surfactants include, for example, Tergitol® durfactant and Triton® surfactants (available from Union Carbide Chemicals anaplastics, Danbury, Conn., Tergitol® and Triton® are registered trademarks of Union Carbide Corporation, New York), polyoxyethylenesorbitans, for example, TWEEN® surfactants (available from Atlas Chemical Industries, Wilmington, Del. Tween® is a registered trademark of Uniqema Americas LLC, Delaware), polyoxyethylene ethers, for example Brij® (Brij is a registered trademark of Uniqema Americas LLC), pharmaceutically acceptable fatty acid esters, for example, lauryl sulfate and salts thereof (SDS), and like materials. A thorough discussion of pharmaceutically acceptable excipients, carriers, stabilizers and other auxiliary substances is available in Remingtons Pharmaceutical Sciences (Mack Pub. Co., N. J. 1991).

A suitable composition for airway delivery of IFN-β related agent may, for example, be formulated as described in U.S. Pat. No. 6,030,609 by dissolving lyophilized IFN-β in a pharmaceutically acceptable vehicle such as sterile distilled water or sterile physiological saline, optionally with addition of one or more carriers, stabilizers, surfactants or other agents in order to enhance effectiveness of the IFN-β related agent. A suitable composition has a pH of from 5 to 8, more preferably 5.5 to 7.5. Preferably, the composition is buffered, e.g. using a citrate buffer.

The Rentschler composition, which is based on formulations disclosed in U.S. Pat. No. 6,030,609, has a pH of 6.5 and osmolarity of 290 mOsm/kg. The composition is preferably provided as a sterile, clear and colorless, ready-to-use aqueous nebulizer solution presented in a disposable glass syringe.

In addition to the active ingredient, the composition preferably comprises a buffering system to maintain the pH at between 5 and 8, more preferably 5.5 and 7.5, especially 6.5. The composition also preferably comprises an antioxidant, for example, DL-methionine.

A composition comprising a therapeutically effective amount of the IFN-β related agent described herein may conveniently be delivered to the lung airways by means of an inhalation device that is capable of delivering fine particles of the active ingredient to the lower respiratory tract or airways. Typically, particles of the active ingredient will have a mass median diameter of 1-10 microns. Suitable inhalation devices include dry powder inhalation (DPI) devices, pressurized metered dose inhalers (pMDI) and aerosol nebulizers.

Typically, the inhalation device will produce an aerosol with a particle size, as determined using a Malvern Masterizer S, with a mass median diameter of 1-10 micron, preferably 3-8 micron, in which mass percent have a diameter below 5 micron is from 25-80%, preferably 30-65%. A suitable nebulizer is the I-neb device, a CE-marked nebulizer manufactured by Philips Respironics.

An appropriate effective amount may be determined by appropriate clinical testing and will vary with for example the activity of the IFN-β related agent administered or induced. The IFN-β related agent may for example, be administered in microgram amounts. They are administered to the subject to be treated in a manner compatible with the dosage formulation, and in an amount that will be effective to bring about the desired effect. The amount to be delivered per dose may be 0.1 µg to 500 µg, for example 1 to 50 µg, depending on the subject to be treated. The treatment normally lasts from 5-7 days and may continue to 14 days if symptoms persist. Treatment may be given from every other day to several times a day. Preferably, treatment is given once per day.

The IFN-β related agent may be administered on its own or simultaneously, sequentially or separately in combination with another therapeutic compound. In particular, the IFN-β, agent or polynucleotide may be administered in conjunction with a therapeutic compound used to treat the respiratory disease or antiviral to the individual. The IFN-β, agent or polynucleotide and additional therapeutic compound may be formulated in the same or different compositions.

In one embodiment, disclosed is a pharmaceutical formulation comprising an effective amount of a drug for treatment of a respiratory or sinus system, and an additive that enhances absorption of the drug into tissue of the respiratory system. In one aspect of this embodiment, the additive comprises a hydrophilic part and a hydrophobic part. In another aspect of this embodiment, the drug is not enclosed in micelles or encapsulated in polymer particles. In another aspect of this embodiment, the formulation does not include oil, a lipid, or a polymer. In yet another aspect of this embodiment, the formulation is an aqueous aerosol formulation, a dry powder aerosol formulation, or a propellant-based formulation.

Blocking T-Req Production

Embodiments are discussed above that involve inducing Treg production via administration of IFNB and IFNB-related agents. In conducting the studies concerning how T-reg production can be induced, it was discovered that administration of certain antibodies can actually inhibit T-reg production. In particular, the Examples below show that administration of anti-TNFR2 blocking antibody or anti-IFNAR1 blocking antibody reduced production of T-reg production. Intentional inhibition of T-reg production would be beneficial in scenarios where immune responses are desired, such as in the instance of cancer and cancer immunotherapies. Anti-TNFR2 and/or anti-IFNAR1 blocking antibodies that are commercially available such as those provided by Invitrogen (Cat #AHR3022, Cat #MA5-31263, Cat #MA1-24723, Cat #MA5-23630) or Biolegend (Cat #BE0247, Cat #113202, Cat #127303) or newly developed antibodies may be used in accord with the teachings herein.

Accordingly, one embodiment involves administering an amount of anti-TNFR2 blocking antibody or anti-IFNAR1 blocking antibody, or both, sufficient to block or reduce production of Treg cells. A related embodiment pertains to a method of enhancing efficacy of a cancer immunotherapy involving co-administering an amount of anti-TNFR2 or anti-IFNAR1 blocking antibody, or both, with a cancer immunotherapy.

The anti-TNFR2 and/or anti-IFNAR1 blocking antibodies may be used in combination with a cancer immunotherapy such that the cancer immunotherapy is enhanced and tumor cytotoxicity is increased. When the anti-TNFR2 and/or anti-IFNAR1 blocking antibodies are used in combination with cancer immunotherapy, the dosage of the drug for cancer immunotherapy can be reduced, which may lead to reduced side effects. Moreover, the reduction in the dosage of the drug for cancer immunotherapy meets social needs including healthcare cost reduction.

Examples of the cancer immunotherapy include cancer vaccine therapy, immune cell infusion therapy, a therapy for reversal of immunosuppression and a therapy for inducing the depletion of regulatory T cells. In some embodiments, the cancer immunotherapy may be a therapy for reversal of immunosuppression. The immune checkpoint inhibitor used in the therapy for reversal of immunosuppression is an anti-CTLA-4 antibody, a PD-1 blocker, an anti-PD-1 antibody, a PD-L1 blocker, an anti-PD-L1 antibody, or the like. Examples of the immune cell infusion therapy include chimeric antigen receptor-modified T-cell therapy. The administration of the agent of the present invention after depletion of regulatory T cells is expected to produce the same effect as produced by a combination of the agent of the present invention with an immune checkpoint inhibitor because regulatory T cells play a role in immunological tolerance. Examples of the drug that induces the depletion of regulatory T cells include alkylating agents, an IL-2-diphtheria toxin fusion protein, an anti-CD25 antibody, an anti-KIR antibody, an IDO inhibitor and a BRAF inhibitor.

Examples of the drug for cancer immunotherapy include Picibanil, Krestin, sizofiran, lentinan, ubenimex, interferons, interleukins, macrophage colony-stimulating factor, granulocyte colony-stimulating factor, erythropoietin, lymphotoxins, BCG vaccine, Corynebacteriumparvum, levamisole, polysaccharide K, procodazole, ipilimumab, nivolumab, ramucirumab, ofatumumab, panitumumab, pembrolizumab, obinutuzumab, trastuzumab emtansine, tocilizumab, bevacizumab, trastuzumab, siltuximab, cetuximab, infliximab, rituximab and metformin.

When anti-TNFR2 and/or anti-IFNAR1 blocking antibodies are used in combination with cancer vaccine, efficient infiltration of cancer vaccine-stimulated T cells into a tumor can be achieved. In addition, the agent of the present invention can enhance the efficacy of immune cell infusion therapy using immune cells such as T cells from a patient or a non-patient.

The anti-TNFR2 and/or anti-IFNAR1 blocking antibodies can be embodied in the form of a medicament. That is, the anti-TNFR2 and/or anti-IFNAR1 blocking antibodies can be produced in a dosage form by blending the anti-TNFR2 and/or anti-IFNAR1 blocking antibodies with a pharmaceutically acceptable carrier or additive as appropriate according to a known production method for pharmaceutical preparations (e.g., the methods described in the Japanese Pharmacopoeia, etc.). Specifically, the anti-TNFR2 and/or anti-IFNAR1 blocking antibodies containing medicament can be, for example, an oral preparation or a parenteral preparation, including tablets (including sugar-coated tablets, film-coated tablets, sublingual tablets, orally disintegrating tablets, and buccal tablets), pills, powders, granules, capsules (including soft capsules and microcapsules), troches, syrups, liquids, emulsions, suspensions, controlled-release preparations (e.g., fast-release preparations, sustained release preparations, sustained release microcapsules, etc.), aerosols, films (e.g., orally disintegrating films, oral mucosal adhesive films, etc.), injections (e.g., subcutaneous injections, intravenous injections, intramuscular injections, intraperitoneal injections, etc.), intravenous infusions, transdermal preparations, ointments, lotions, patches, suppositories (e.g., rectal suppositories, vaginal suppositories, etc.), pellets, transnasal preparations, transpulmonary preparations (inhalants), and eye drops. The amount of the carrier or the additive to be added is determined as appropriate based on the range of amount conventionally used in the pharmaceutical field. The carrier or the additive that can be added is not particularly limited, and examples include various carriers such as water, physiological saline, other aqueous solvents, and aqueous or oily bases; and various additives such as fillers, binders, pH adjusters, disintegrants, absorption enhancers, lubricants, colorants, corrigents and flavors.

Examples

Example 1: Lung TNFR2$^+$ cDC2 (R2D2) Population Maintains Lung Mucosal Tolerance at Steady-State It was reasoned that lung mucosal tolerance is actively maintained by a specialized lung DC population, and mice lacking this tolerogenic lung DC population will spontaneously lose lung mucosal tolerance. We first examined lung CD4$^+$ T cells in mice lacking different DC subsets, Batf3$^{-/-}$ (cDC1), IRF4$^{fl/fl}$CD11c$^{cre}$ (cDC2) and CCR2$^{-/-}$ (moDCs). Only the IRF4$^{fl/fl}$CD11c$^{cre}$ mice had spontaneously increased CD4$^+$ T cells in the lung (FIG. 1A). Furthermore, IRF4$^{fl/fl}$CD11c$^{cre}$ mice had enlarged mediastinal lymph nodes (medLNs), but relatively normal spleens (FIG. 1C-1D) suggesting a selective loss-of-lung tolerance by the lack of cDC2.

cDC2 is a heterogeneous population (Tussiwand R, Everts B, Grajales-Reyes G E, Kretzer N M, Iwata A, Bagaitkar J et al. KIf4 expression in conventional dendritic cells is required for T helper 2 cell responses. *Immunity* 2015; 42(5): 916-928. Mansouri S, Patel S, Katikaneni D S, Blaauboer S M, Wang W, Schattgen S et al. Immature lung TNFR2(−) conventional DC 2 subpopulation activates moDCs to promote cyclic di-GMP mucosal adjuvant responses in vivo. *Mucosal Immunol* 2019; 12(1): 277-289.). We reasoned that to actively maintain lung tolerance, the tolerogenic cDC2 subset may be constitutively activated. A subpopulation of lung cDC2, marked by expression of TNFR2, has constitutively activated RelB (pRelB) (FIG. 9A-9B) (Mansouri, 2019, supra). Notably, the TNFR2$^+$ cDC2 (R2D2) population is the only lung DC subset that has constitutively activated RelB (FIG. 9C). TNFR2$^{-/-}$mice lack the pRelB$^+$ cDC2 subpopulation[21]. Furthermore, the R2D2 population expresses tolerogenic DC markers of PD-L1, PD-L2, Arg-1, BTLA (Mansouri 2019, supra). Last, the lack of RelB expression in DCs promotes the development of spontaneous allergic airway inflammation[30]. We thus generated RelB$^{fl/fl}$CD11c$^{cre}$ and TNFR2$^{fl/fl}$CD11c$^{cre}$ mice to examine their lung mucosal tolerance at the steady-state.

Similar to the IRF4$^{fl/fl}$CD11c$^{cre}$ mice, RelB$^{fl/fl}$CD11c$^{cre}$ and TNFR2$^{fl/fl}$CD11c$^{cre}$ mice had increased immune cells in the lung and medLNs, but not the spleen (FIG. 1B-1D). The IRF4$^{fl/fl}$CD11c$^{cre}$, RelB$^{fl/fl}$CD11c$^{cre}$ and TNFR2$^{fl/fl}$CD11c$^{cre}$ mice may delete IRF4, RelB and TNFR2 in other lung CD11c$^+$ cells. We examined RelB, IRF4, and TNFR2 expression in these mice. We found that while RelB$^{fl/fl}$ CD11c$^{cre}$ deleted RelB in alveolar macrophage (AM), IRF4 and TNFR2 expression in lung AM were intact in the IRF4$^{fl/fl}$CD11c$^{cre}$ or TNFR2$^{fl/fl}$CD11c$^{cre}$ mice (FIG. 9D-9F). Nevertheless, to exclude the possibility that the lack of IRF4, RelB or TNFR2 in lung cells other than R2D2 cause spontaneous lung inflammation, we did the adoptive cell transfer experiment. We sorted out lung TNFR2$^+$ (R2D2) and TNFR2$^-$ cDC2 from C57BL/6 mice and adoptively transfer (i.n.) them into the IRF4$^{fl/fl}$CD11c$^{cre}$ recipient mice. The quality of the adoptive cell transfer was confirmed after 24 hrs (FIG. 9G-9H). After two weeks, IRF4$^{fl/fl}$ CD11c$^{cre}$mice receiving WT R2D2 cells had their lung CD4$^+$ T cells numbers reduced while the IRF4$^{fl/fl}$CD11 C$^{cre}$ mice receiving the WT TNFR2$^-$ cDC2 still had elevated numbers of lung CD4$^+$ T cells (FIG. 1E). Together, these data strongly suggested that lung R2D2 population maintains lung mucosal tolerance at the steady-state.

Figure 10:
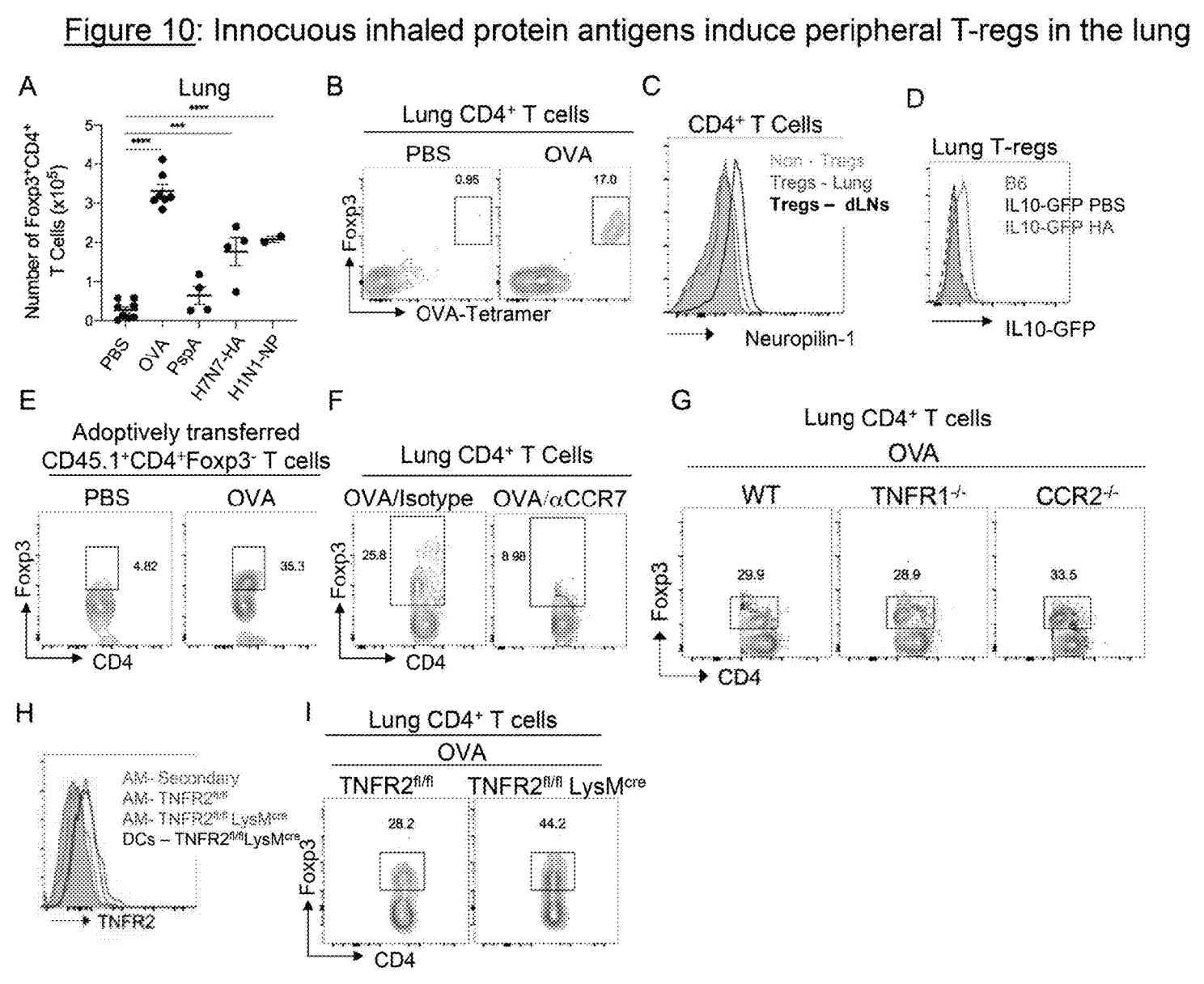

Example 2: Lung Mgl2$^+$/IDO-1$^+$ R2D2 Population Promotes Antigen-Specific Lung T-Regs Induction at Steady-State DCs promote tolerance via the generation of T-regs (Akbari O, DeKruyff R H, Umetsu D T. Pulmonary dendritic cells producing IL-10 mediate tolerance induced by respiratory exposure to antigen. *Nat Immunol* 2001; 2(8): 725-731. de Heer H J, Hammad H, Soullie T, Hijdra D, Vos N, Willart M A et al. Essential role of lung plasmacytoid dendritic cells in preventing asthmatic reactions to harmless inhaled antigen. *J Exp Med* 2004; 200(1): 89-98. Hintzen G, Ohl L, del Rio M L, Rodriguez-Barbosa J I, Pabst O, Kocks J R et al. Induction of tolerance to innocuous inhaled antigen relies on a CCR7-dependent dendritic cell-mediated antigen transport to the bronchial lymph node. *J Immunol* 2006; 177(10): 7346-7354. Semmrich M, Plantinga M, Svensson-Frej M, Uronen-Hansson H, Gustafsson T, Mowat A M et al. Directed antigen targeting in vivo identifies a role for CD103+ dendritic cells in both tolerogenic and immunogenic T-cell responses. *Mucosal Immunol* 2012; 5(2): 150-160). We found that lung from IRF4$^{fl/fl}$CD11c$^{cre}$ had decreased T-regs at the steady-state (FIG. 1F). We reasoned that R2D2 cells induce T-regs in the lung. Intranasal administration of one dose of 1 μg innocuous protein antigens (e.g., OVA, PspA, H7N7-HA, H1N1-NP) induces lung T-regs (FIG. 10A). These lung T-regs were antigen-specific and neuropilin-negative peripheral T-regs (FIG. 10B-10C). They also produce IL-10 (FIG. 10D). Furthermore, intranasal administration of OVA turned adoptive transferred (i.v)

naïve CD45.1$^+$ T cells into Foxp3$^+$ T-regs in vivo (FIG. 9E). Last, consistent with previous report[3], blocking DC migration by anti-CCR7 mAb inhibited OVA-induced lung T-regs induction (FIG. 9F).

The induction of lung T-regs by OVA depended on IRF4, RelB, or TNFR2 expression in CD11 C$^+$ cells but not Batf3, TNFR1, or CCR2 (FIG. 2A-2C, 10G). Adoptive transfer of R2D2 cells, but not lung TNFR2$^-$ cDC2 or lung tissue macrophage, restored lung T-regs induction in the IRF4$^{fl/fl}$ CD11c$^{cre}$ mice (FIG. 2D, 1H). Notably, the TNF2$^{fl/fl}$LysM$^{cre}$ mice, which delete TNFR2 in myeloid cells, had unaltered lung T-regs induction (FIG. 10I). Thus, the lung R2D2 population generates lung T-regs. R2D2 cells express tolerogenic DC markers of PD-L1, Arg-12[1]. Closer examination found that a subpopulation of R2D2 expresses Mgl2 (FIG. 2E). The Mgl2$^+$R2D2 population is PD-L1$^+$PD-L2$^+$ ILT3$^+$Arg-1$^+$ and constitutively express indoleamine 2,3-dioxygenase 1 (IDO-1) (FIG. 2E). Notably, all the IDO-1$^+$ R2D2 cells are Mgl2$^+$ and Arg1$^+$ (FIG. 2F). The Mgl2$^+$ DC population has been characterized before in the skin to promote T$_H$2 responses and suppress T$_{FH}$ response (Kumamoto Y, Linehan M, Weinstein J S, Laidlaw B J, Craft J E, Iwasaki A. CD301 b(+) dermal dendritic cells drive T helper 2 cell-mediated immunity. *Immunity* 2013; 39(4): 733-743. Kumamoto Y, Hirai T, Wong P W, Kaplan D H, Iwasaki A. CD301 b(+) dendritic cells suppress T follicular helper cells and antibody responses to protein antigens. Elife 2016; 5). We then adoptively transferred (i.n.) lung Mgl2$^+$R2D2 and Mgl2-R2D2 cells into the IRF4$^{fl/fl}$CD11 Cc$^r$e mice and examined their ability to induce lung T-regs. Only Mgl2$^+$ R2D2 generated lung T-regs in the IRF4$^{fl/fl}$CD11c$^{cre}$ mice (FIG. 2G). Taken together, the lung Mgl2$^+$/IDO-1$^+$ R2D2 population induces lung T-regs at steady-state.

Figure 3:
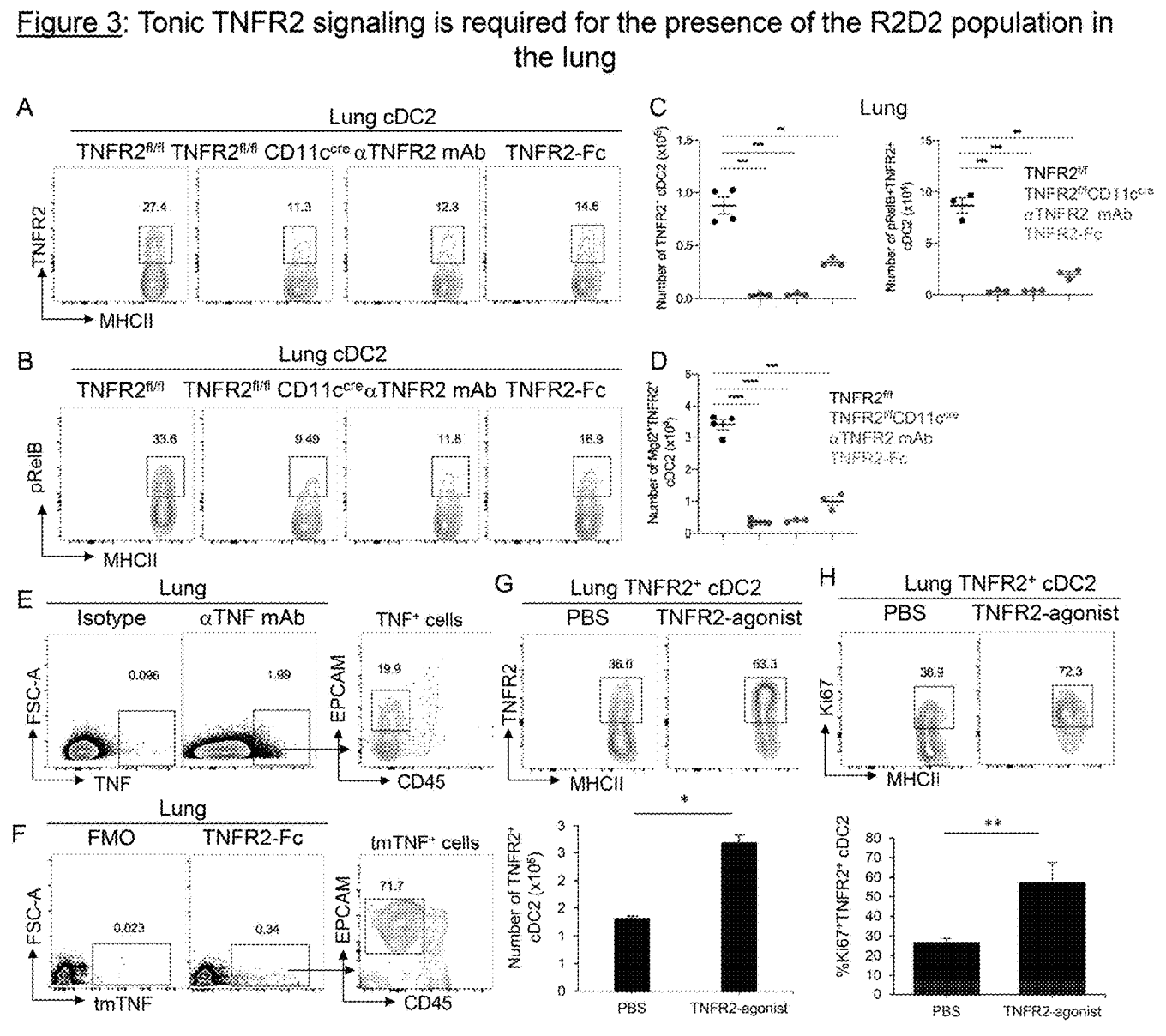
Figure 11:
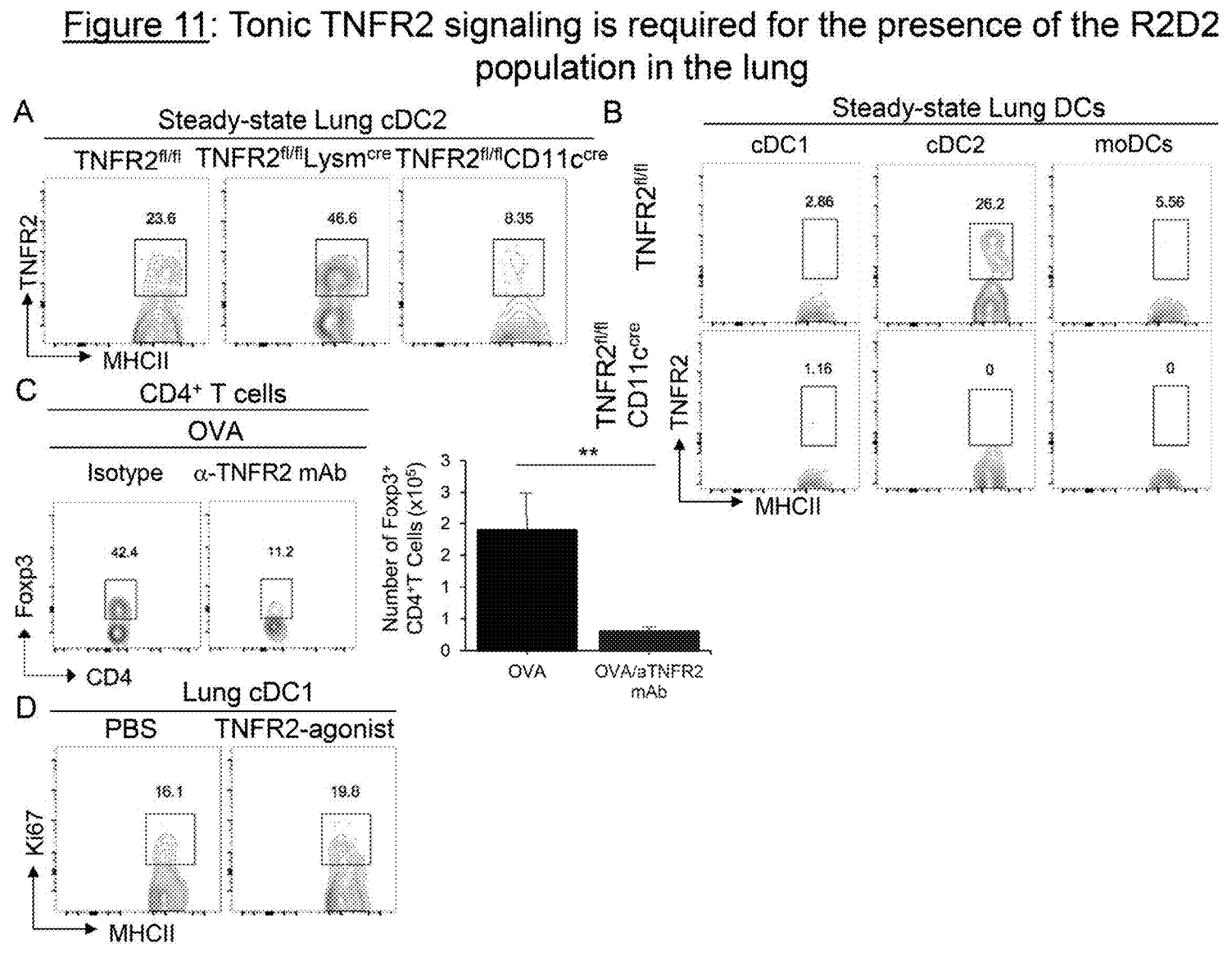

Example 3: Constitutive TNFR2 Signaling is Required for the Presence of R2D2 Population in the Lung at Steady-State TNFR2$^{-/-}$ mice lack the pRelB$^+$ population (Mansouri 2019, supra). Here, we found that TNFR2$^{fl/fl}$CD11c$^{cre}$, not the TNFR2$^{fl/fl}$LysM$^{cre}$ mice, lack the TNFR2$^+$pRelB$^+$ cDC2 (R2D2) population (FIG. 3A-3B, 11A). Thus, TNFR2 expression in DCs mediates pRelB activation. Notably, at the steady-state, lung cDC2 is the only TNFR2+ DCs population (FIG. 11B). We hypothesized that there was an active TNFR2-pRelB signaling in the lung R2D2 population at steady-state.

Indeed, blocking TNFR2 signaling with anti-TNFR2 blocking mAb inhibited pRelB expression in cDC2 (FIG. 3B) and T-regs induction in the lung (FIG. 11C). Unexpected, blocking TNFR2 dramatically decreased the numbers of lung TNFR2+pRelB$^+$ cDC2 (R2D2) at steady-state (FIG. 3A-3C). To exclude the possibility that the anti-TNFR2 blocking mAb may interfere with the TNFR2 detection by Flow cytometry, we used the TNFR2-Fc (human IgG1) fusion protein to disrupt the TNFR2 interaction with its ligand in vivo. Again, TNFR2-Fc (human IgG1) reduced R2D2 population (FIG. 3A-3C). Notably, in these experiments, the numbers of lung R2D2 cells showed a more dramatic reduction (FIG. 3C) than the percentage changes (FIG. 3A). Indeed, the total numbers of lung cDC2 cells decreased in the TNFR2$^{fl/fl}$CD11c$^{cre}$ mice, mice treated with anti-TNFR2 blocking mAb or TNFR2-Fc likely due to the loss of the R2D2 subpopulation in lung cDC2 subset.

We further examined the Mgl2$^+$/IDO-1$^+$ R2D2 population and found, as expected, that blocking TNFR2 or TNFR2-Fc treatment reduced the Mgl2$^+$ R2D2 number by 90% (FIG.

3D). Thus, the lung R2D2, including the T-reg inducing Mgl2$^+$ R2D2 subset, depends on the constitutive TNFR2 signaling.

TNFR2 binds specifically to transmembrane TNF (tmTNF)(Grell M, Douni E, Wajant H, Lohden M, Clauss M, Maxeiner B et al. The transmembrane form of tumor necrosis factor is the prime activating ligand of the 80 kDa tumor necrosis factor receptor. *Cell* 1995; 83(5): 793-802). To identify TNF-expressing lung cells at the steady-state, we first did intracellular TNF staining to detect total cellular TNF including tmTNF and soluble TNF. We found that the CD45$^-$ lung cells were the main TNF$^+$ lung cells at steady-state (FIG. 3E). Next, we used the TNFR2-Fc (human IgG1) fusion protein to detected TNFR2 ligands, i.e., tmTNF. TNFR2 ligands were mainly on CD45-EP-CAM$^+$ lung epithelial cells at the steady-state (FIG. 3F). We reasoned that, at the steady-state, tmTNF on lung epithelial cells engages TNFR2 on R2D2 to maintain its presence in the lung.

To mimic the effect of tmTNF, we made a TNF$_{D221N/A223R}$ mutant that only binds to TNFR2[33]. TNF$_{D221N/A223R}$ is a monomer. TNF works as a trimer[34]. We first crosslinked TNFR2 with the non-blocking TNFR2 mAb followed by the addition of TNF$_{D221N/A223R}$ to activate TNFR2 signaling. Intranasal administration of a non-blocking anti-TNFR2 mAb (TR75.89) and the TNF$_{D221N/A223R}$ increased R2D2 population (FIG. 3G). Importantly, we found increased Ki67$^+$ cells in the R2D2 population in mice treated with tmTNF (FIG. 3H), indicating the enhanced proliferation of R2D2 cells by TNFR2 engagement. As a negative control, intranasal administration of TNF$_{D221N/A223R}$ did not enhance Ki67 expression in the cDC1 population, which do not express TNFR2 (FIG. 11D). In conclusion, the steady-state lung R2D2 population, including the Mgl2$^+$/IDO-1$^+$R2D2, is a specialized DC subset adapted to the lung microenvironment and needs the constitutive tmTNF-TNFR2 signaling for its existence.

Example 4: Constitutive IFNAR1 Signaling in Mgl2$^+$R2D2 Cells Drives Lung T-Regs Induction IDO-1$^+$, not IDO-1$^-$, R2D2 cells induce lung T-regs. However, we found that intranasal administration of an anti-IFNAR1 blocking mAb inhibited T-regs induction in the lung (FIG. 4A) but did not affect IDO-1 expression in R2D2 cells (FIG. 12A). Similarly, IFNAR1$^{-/-}$ mice failed to generated lung T-regs in response to OVA (FIG. 4B) but retained the R2D2 population, including the Mgl2$^+$ R2D2 (FIG. 12B) population in the lung. Thus, IDO-1 or Mgl2 expression in R2D2 is not sufficient for T-regs induction. Rather, IFNAR1 signaling is critical.

Figure 4:
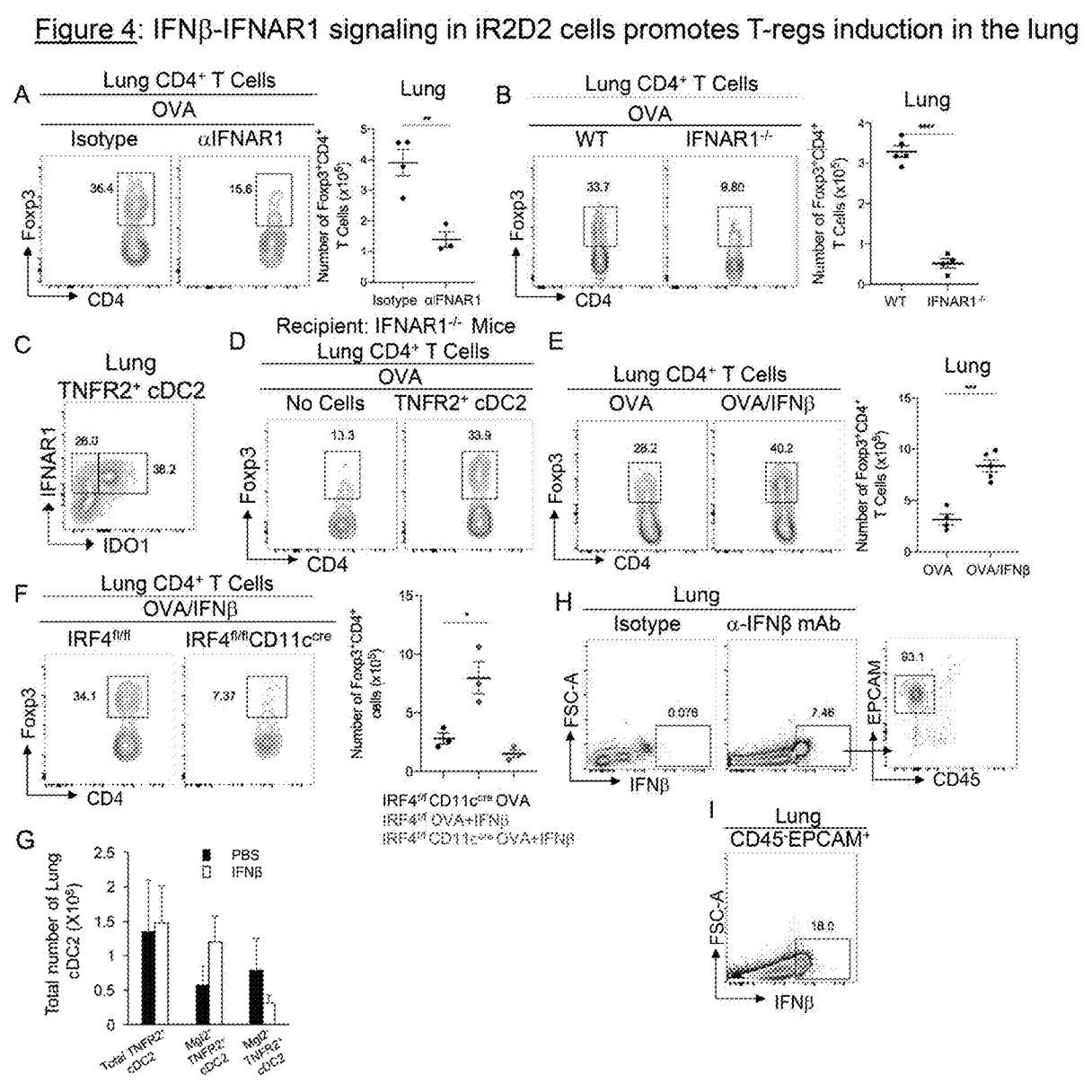

R2D2 has the highest expression of IFNAR1 among lung DCs subsets (FIG. 12C-12D) at steady-state. In the R2D2 population, all IDO-1$^+$ R2D2 cells express high IFNAR1 compared to the IDO-1-R2D2 (FIG. 4C). To establish that R2D2 cell-intrinsic IFNAR1 signaling promotes lung T-regs induction, we adoptively transferred (i.n.) WT R2D2 into IFNAR1$^{-/-}$ mice and treated the recipient mice with OVA. After 14 days, we found that IFNAR1$^{-/-}$ mice receiving WT R2D2 cells restored T-regs induction in the lung (FIG. 4D). We concluded that R2D2 cell-intrinsic IFNAR1 signaling is sufficient for lung T-regs induction.

Indeed, intranasal administration of IFNβ enhanced T-regs induction in the lung (FIG. 4E). Importantly, IFNβ did not induce T-regs in IRF4$^{fl/fl}$CD11c$^{cre}$ mice, suggesting IFNβ acts on cDC2 to induce T-regs (FIG. 4F). Interestingly, the intranasal administration of IFNβ did not increase the total number of lung R2D2 cells (FIG. 4G). Rather, IFNβ treatment tended to increase cell numbers of Mgl2$^+$ R2D2 while decrease numbers of Mgl2$^-$ R2D2 (FIG. 4G) suggesting IFNβ treatment in vivo may turn Mgl2-into Tregs-inducing Mgl2$^+$R2D2. In light of the critical role of R2D2 intrinsic IFANR1 signaling in T-regs induction, we named the T-regs inducing Mgl2$^+$/IDO-1$^+$ R2D2 as IFNAR1$^{hi}$R2D2 (iR2D2).

Last, we wanted to determine the cellular source of IFNβ in the lung that generates iR2D2 at steady-state. Using intracellular IFNβ stain, we found that at steady-state, the Epcam$^+$CD45$^-$ lung epithelial cells were the sole IFNβ$^+$ producing cells (FIG. 4H). Intriguingly, only ~18% EPCAM$^+$CD45$^-$ lung epithelial cells were IFNβ$^+$ suggesting a selected population of lung epithelial cells are responsible for IFNβ production at steady-state (FIG. 4I).

Example 5: IFNβ Activates TGFβ1 in iR2D2 to Drives Lung T-Regs Induction

Figure 5:
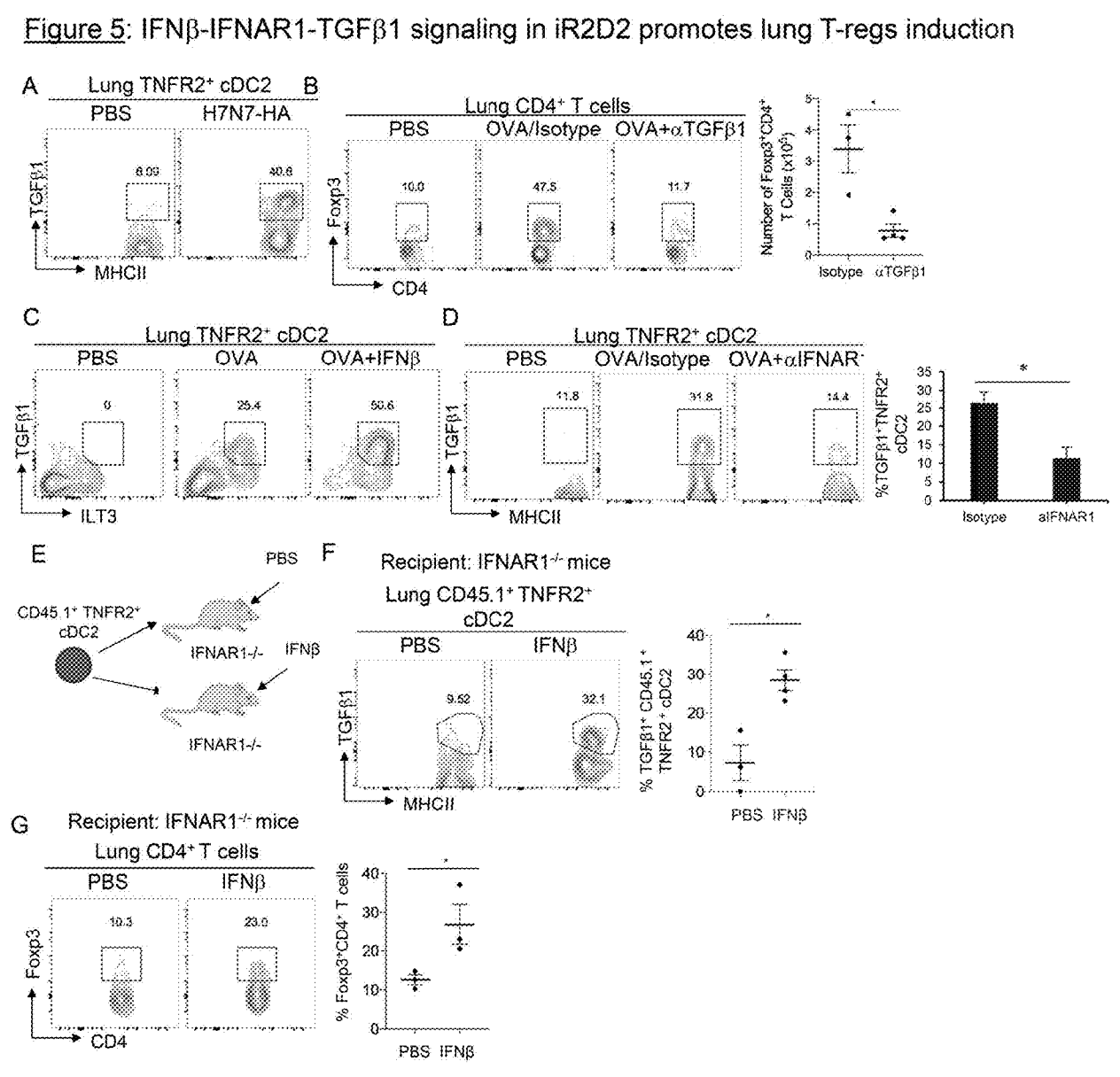

How does the IFNAR1 signaling activate the tolerogenic program in the iR2D2 cells? pT-regs are generated by TGFβ1[26-28]. R2D2 produced TGFβ1 in response to H7N7 influenza HA antigen (FIG. 5A). Neutralizing TGFβ1 inhibited T-regs induction in the lung (FIG. 5B).

The induction of TGFβ1 in R2D2 dependeds on IFNβ-IFNAR1 signaling. Intranasal administration of IFNβ increased TGFβ1 in R2D2 (FIG. 5C) while anti-IFNAR1 blocking mAb inhibited OVA-induced TGFβ1 production in R2D2 (FIG. 5D). Notably, anti-IFNAR1 mAb did not affect OVA-induced TGFβ1 production in cDC1, moDCs or AMs (FIG. 13A). Block IFNAR1 inhibited OVA-induced T-regs induction (FIG. 4A). Thus, TGFβ1 production by cDC1, AM or moDCs were not sufficient for the induction of T-regs in the lung.

To establish that IFNβ acted on R2D2 to induce TGFβ1 expression, we adoptively transferred (i.n.) the lung R2D2 cells from the CD45.1$^+$ mice into IFNAR1$^{-/-}$ mice and treated (i.n.) the recipient IFNAR1$^{-/-}$ mice with IFNβ (FIG. 5E). We found that IFNβ administration induced TGFβ1 in the transferred CD45.1$^+$ cells (FIG. 5F). Furthermore, IFNβ restored T-regs induction in the IFNAR1$^{-/-}$ mice received CD45.1+R2D2 cells (FIG. 5G), suggesting that IFNβ acted on lung R2D2 cells to generate TGFβ1 for lung T-regs induction. Taken together, IFNAR1 signaling in iR2D2 induces T-regs by producing TGFβ1.

Example 6: R2D2 Cells Promote T$_H$2 Responses in HDM-Induced Asthmatic Mice cDC2 mediates HDM-induced asthma (Tussiwand R, Everts B, Grajales-Reyes G E, Kretzer N M, Iwata A, Bagaitkar J et al. KIf4 expression in conventional dendritic cells is required for T helper 2 cell responses. *Immunity* 2015; 42(5): 916-928. Plantinga M, Guilliams M, Vanheerswynghels M, Deswarte K, Branco-Madeira F, Toussaint W et al. Conventional and monocyte-derived CD11 b(+) dendritic cells initiate and maintain T helper 2 cell-mediated immunity to house dust mite allergen. *Immunity* 2013; 38(2): 322-335). Recent studies indicated that a KIf4$^+$/Mgl2$^+$, RelB$^+$ cDC2 subset mediates HDM-induced T$_H$2 responses. iR2D2 expresses Mgl2, RelB. We suspected that the lung R2D2 population may be plastic and promotes T$_H$2 response in HDM-induced asthma.

First, we generated the HDM induced asthmatic mice (FIG. 6A). HDM-treated mice generated HDM-specific IgE and IgG1 (FIG. 14A), lung inflammation determined by H&E stain (FIG. 14B), eosinophils infiltration in the lung (FIG. 14C) and T$_H$2 dominant cytokines in draining lymph nodes (FIG. 14D). Next, we examined the iR2D2 population in the asthmatic mice. We found increased numbers of total R2D2 cells in the asthmatic cells (FIG. 6B). The Mgl2$^+$/IDO-1$^+$ R2D2 population increased as well in the HDM-induced asthmatic mice (FIG. 6C, 14E). However, no T-regs were generated in HDM mice (FIG. 6D). The R2D2 cells from HDM-induced mice also downregulated tolerogenic markers PD-L1, PD-L2, and, critically, IFNAR1 expression (FIG. 6E). In contrast, R2D2 cells from the HDM mice increased immunogenic markers OX40L, ICOSL, and T1/ST2 (FIG. 6F).

Last, adoptive transfer (i.n.) R2D2 from HDM mice into naïve mice generated T$_H$2 response in vivo (FIG. 6G), which was different from the T-regs inducing R2D2 at the steady-state (FIG. 2D). Comparing the tolerogenic R2D2 (iR2D2) from OVA treated mice with the T$_H$2-promoting R2D2 from the HDM mice, the tolerogenic R2D2 expresses TGFβ1 while the immunogenic R2D2 expresses IL-4 and IL-4/TGFβ1 (FIG. 6H). We concluded that the lung R2D2 population is plastic and can promote T-regs or T$_H$2 responses depending on the environmental cue, e.g., IFNβ or HDM.

Figure 7:
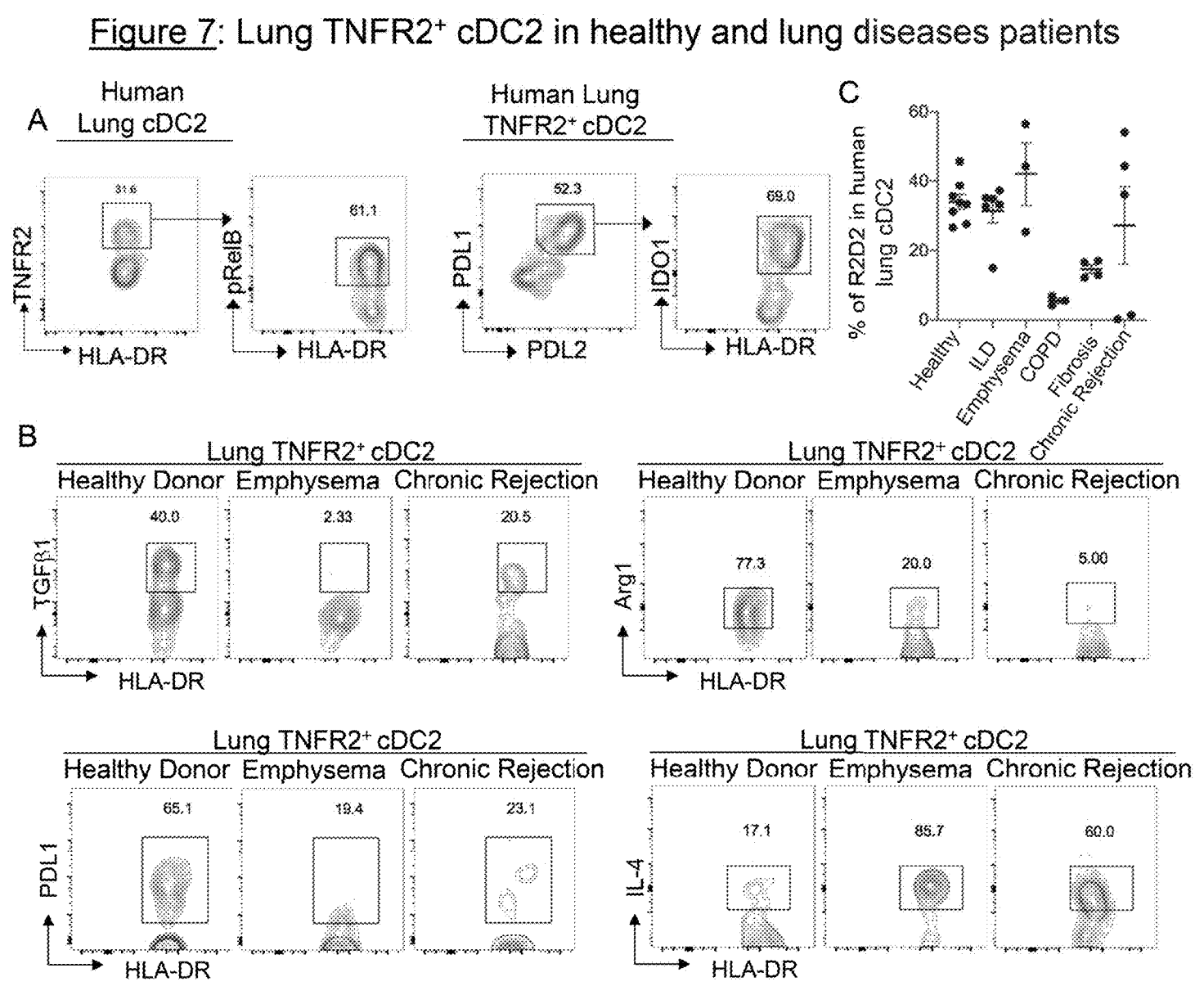

Example 7: Human Lungs have a Phenotypically Similar Plastic iR2D2 Population We reasoned that healthy human lung should have a functionally similar tolerogenic DC subset. Little is known about human lung cDC2 subsets in healthy individuals or patients. We sampled healthy donor lungs that were transplanted into lung patients and identified the same TNFR2$^+$ pRelB$^+$IDO-1$^+$PD-L1$^+$PD-L2$^+$ cDC2 population in the healthy human lungs (FIG. 7A, 15A-15B). The healthy human iR2D2 cells constitutively express TGFβ1 and Arg-1 (FIG. 7B) as well.

We also identified IDO-1$^+$ R2D2 population in lung explants from emphysema, interstitial lung disease patients (FIG. 7C). However, R2D2 cells from lung patients had decreased TGFβ1, Arg-1, PD-L1, but increased IL-4 expression (FIG. 7B) similar to the R2D2 from the asthmatic mice. Notably, lung explants from COPD patients had very little R2D2 cells (FIG. 7C). We conclude that the phenotypically similar R2D2 cells can be found in healthy human lungs and some lung disease patients.

Methods Related Examples 1-7

| KEY RESOURCES TABLE | | |
| --- | --- | --- |
| REAGENT or RESOURCE | SOURCE | IDENTIFIER |
| Antibodies | | |
| Anti-mouse CD4-PE/Cy7 (clone: GK1.5) | BioLegend | Cat#100422 |
| Anti-mouse IFNβ-PerCP/Cy5.5 (clone: XMG1.2) | BioLegend | Cat#505822 |
| Anti-mouse IL-4-APC (clone: 11B11) | BioLegend | Cat#504106 |
| Anti-mouse IL-17a-PE (clone: TC11-1810.1) | BioLegend | Cat#506903 |
| Anti-mouse CD44-Alexa Fluor 700 (clone: IM7) | BioLegend | Cat#103025 |
| Anti-mouse CD45-PercP/Cy5.5 (clone: 30-F11) | Biolegend | Cat#103131 |
| Anti-mouse Foxp3-Pacific Blue (clone: MF-14) | BioLegend | Cat#26410 |
| Anti-mouse MHCII(I-A/I-E)-Brilliant Violet 421 (clone: M5/114.15.2) | BioLegend | Cat#107636 |
| Anti-mouse MHCII(I-A/I-E)-Alexa Fluor (clone: M5/114.15.2) | BioLegend | Cat#107622 |
| Anti-mouse CD11c-APC/Cy7 (clone: N418) | Biolegend | Cat#117323 |
| Anti-mouse/human CD11b-PE/Cy7 (clone: M1/70) | BioLegend | Cat#101216 |
| Anti-mouse/human CD11b-Brilliant Violet 605 (clone: M1/70) | BioLegend | Cat#101237 |
| Anti-mouse CD64-PerCP/Cy5.5 (clone: X54-5/7.1) | BioLegend | Cat#139307 |
| Anti-mouse TNFR2-PE (Clone:TR75-89) | BioLegend | Cat#113405 |
| Anti-mouse TNFR2-APC (Clone: REA228) | Miltenyi Biotec | Cat#130-104-698 |
| Anti-mousPDL1-Brilliant Violet 421 (clone: 10F.9G2) | BioLegend | Cat#124315 |
| Anti-mouse PDL2-APC (clone: TY25) | BioLegend | Cat#107210 |
| Anti-mouse/human Arg1-FITC | RD systems | Cat#IC5868F |
| Anti-mouse ILT3-PE (clone: H1.1) | BioLegend | Cat#144904 |
| Anti-mouse IDO1-Alexa Fluor (clone: 2E2/IDO1) | BioLegend | Cat#654003 |
| Anti-mouse/human pReIB-PE (clone: D4169) | Cell Signaling Technology | Cat#:13567 |
| Anti-mouse EPCAM-PerCP/Cy5.5 (clone: G8.8) | BioLegend | Cat#118219 |
| Anti-mouse/human Ki67-PE (clone: 11F6) | BioLegend | Cat#151209 |
| Anti-mouse IFNAR1-APC (clone: MAR1-5A3) | BioLegend | Cat#127313 |
| Anti-mouse IFNβ-Primary (clone: D2J1D) | Cell Signaling Technology | Cat#:974505 |
| Anti-mouse TNF-Primary (clone: D2D4) | Cell Signaling Technology | Cat#:11948 |
| Anti-mouse LAP (TGFβ1)-Brilliant Violet 421 (clone: TW7-1664) | BioLegend | Cat#141407 |
| Anti-mouse LAP (TGFβ1)-FITC (clone: TW7-1664) | BioLegend | Cat#141413 |
| Anti-mouse CD45.1-APC (clone: A20) | BioLegend | Cat#110713 |
| Anti-mouse OX40L-PE (clone: RM134L) | BioLegend | Cat#108805 |
| Anti-mouse ICOSL-PE (clone: HK5.3) | BioLegend | Cat#107405 |

-continued

| KEY RESOURCES TABLE | | |
|---|---|---|
| REAGENT or RESOURCE | SOURCE | IDENTIFIER |
| Anti-mouse T1ST2-APC (clone: Di H4) | BioLegend | Cat#146605 |
| Anti-mouse IRF4-APC (clone: IRF4.3E4) | BioLegend | Cat#646407 |
| Anti-human TNFR2-APC (clone: 3G7A02) | BioLegend | Cat#358405 |
| Anti-human HLA-DR-APC/Cy7 (clone: L243) | BioLegend | Cat#307617 |
| Anti-human PDL1-Brilliant Violet 421 (clone: 29E.2A3) | BioLegend | Cat#329713 |
| Anti-human PDL2-PE (clone: 24F.10C12) | BioLegend | Cat#329605 |
| Anti-human IDO1-Primary | R&D Systems | Cat#MAB6030 |
| Anti-human TGFβ1-PE (clone : Tw4-2F8) | BioLegend | Cat#349603 |
| Anti-human Arginase 1-PE (clone: 14D2C43) | BioLegend | Cat#369703 |
| Anti-human IL-4-PE (clone: G077F6) | BioLegend | Cat#355003 |
| Anti-mouse F4/80-PerCP/Cy5.5 (clone: BM8) | BioLegend | Cat#123127 |
| I-A(b) chicken ova 325-335 QAVHAAHAEIN APC-Labeled Tetramer | NIH Tetramer Core Facility | |
| I-A(b) human CLIP 87-101 PVSKMRMATPLLMQA (Control) APC Labeled Tetramer | NIH Tetramer Core Facility | |
| Anti-mouse Neuropilin-APC (clone: 3E12) | BioLegend | Cat#145205 |
| Anti-human CD1c-PE/Cy7 (clone: L161) | BioLegend | Cat#331515 |
| Anti-human CD14-PerCP/Cy5.5 (clone: 63D3) | BioLegend | Cat#367109 |
| Anti-human CD206-FITC (clone: 15-2) | BioLegend | Cat#321103 |
| anti-mouse IgG1-HRP | Southern Biotech | Cat#1030-05 |
| anti-mouse IgE-HRP | Southern Biotech | Cat#1110-05 |
| Chemicals, Peptides, and Recombinant Proteins | | |
| Cell Activation Cocktail with Brefreldin A | Biolegend | 423303 |
| OVA | Invivogen | cat#vac-pova |
| Anti-CCR7 monoclonal antibody | R&D Systems | Cat#MAB34477 |
| Anti-TNFR2 monoclonal antibody (clone: TR75-54.7) | BioXcell | Cat#BE0247 |
| Anti-TNFR2 monoclonal antibody (clone: TR75-32.4) | Biolegend | Cat#113202 |
| Isotype Control (clone HTK888) | Biolegend | Cat#400931 |
| TNFR2-Fc (human IgG1) fusion protein | SinoBiological | Cat#50128-M02H |
| TNFR2-agonist (TNF$_{D221N/A223R}$) | Creative ® Biolabs | Custom made |
| Anti-IFNAR1 monoclonal antibody (clone: MAR1-5A3) | Biolegend | Cat#127303 |
| Recombinant murine IFNβ | R&D | Cat#8234-MB/CF |
| anti-TGFβ1 neutralizing antibody (19D8) | Biolegend | Cat#521707 |
| House dust mites Dermatophagoides pteronyssinus (HDM-Der p1) | Greer Laboratories | Cat#XPB82D3A2.5 |
| Dermatophagoides farinae (HDM-Der f 1) | Greer Laboratories | Cat#XPB81D3A2.5 |
| PspA | BEI Resources, NIAID, NIH | NR-33178 |
| H7N7-HA | BEI Resources, NIAID, NIH | NR-2633 |
| H1N1-NP | SinoBiological | cat#11675-V08B |
| Foxp3/Transcription Factor Staining Buffer Set | EBioscience | cat#00-5523-00 |
| Experimental Models: Organisms/Strains | | |
| Mouse: IRF4$^{fl/fl}$ | Jackson Laboratory | Cat#009380 |
| Mouse: CD11c$^{Cre}$ | Jackson Laboratory | Cat#008068 |
| Mouse: Batf3$^{-/-}$ | Jackson Laboratory | Cat#013596 |
| Mouse: CCR2$^{-/-}$ | Jackson Laboratory | Cat#004999 |
| Mouse: RelB$^{fl/fl}$ | Jackson Laboratory | Cat#028719 |
| Mouse: TNFR2$^{fl/fl}$ [C57BL/6-Tnfrsf1b < tm1c(EUCOMM)Wtsi>/lcs] | EMMA-European Mouse Mutant Archive | Cat#05925 |
| Mouse: IL-10$^{eGFP}$ | Jackson Laboratory | Cat#014530 |
| Mouse: IFNAR1$^{-/-}$ | Jackson Laboratory | Cat#028288 |
| Mouse: CD45.1 | Jackson Laboratory | Cat#002014 |
| Mouse: Lysm$^{cre}$ | Jackson Laboratory | Cat#004781 |

-continued

| KEY RESOURCES TABLE | | |
|---|---|---|
| REAGENT or RESOURCE | SOURCE | IDENTIFIER |
| Software and Algorithms | | |
| FlowJo version 10.1r1 | FlowJo | http://www.flowjo.com |
| Prism6 | GraphPad | http://www.graphpad.com |

Mice. Age- and gender-matched mice (8-18 weeks old) were used for all experiments. C57BL/6, B6.CD45.1, Batf3$^{-/-}$CCR2$^{-/-}$, IL-10$^{GFP}$, IRF4$^{fl/fl}$, RelB$^{fl/fl}$, IFNAR1$^{-/-}$, CD11c$^{cre}$, LysM$^{cre}$ and TNFR1$^{-/-}$ mice on C57BL/6 background were purchased from The Jackson Laboratory. TNFR2$^{fl/fl}$ mice were from the Euorpean Conditional Mouse Mutagenesis Program. Mice were housed and bred under pathogen-free conditions in the Animal Research Facility at the University of Florida. All mouse experiments were performed by the regulations and approval of the Institutional Animal Care and Use Committee at the University of Florida, IACUC number 201909362.

Reagents. Anti-TNFR2 monoclonal antibody (20 μg, TR75-54.7, BioXcell or TR75-32.4, BioLegend), anti-IFNAR1 monoclonal antibody (20 μg, MAR1-5A3, BioLegend), isotype control (20 μg HTK888, BioLegend), anti-TGFβ1 neutralizing antibody (75 μg, 19D8, BioLegend), anti-IFNβ monoclonal antibody (D2J1D, Cell Signaling, cat no. 97450), TNFR2-Fc (human IgG1) fusion protein (2 μg, SinoBiological, cat no. 50128-M02H) or TNF$_{D221N/A223R}$ (1 μg, custom made by Creative® Biolabs) were administered intranasally in 40 μl PBS. Recombinant mouse IFNβ (200 ng, ~240,000 IU) (R&D, cat no. 8234-MB/CF) was administered i.n. in 40 μl PBS.

The following reagent was obtained through BEI Resources, NIAID, NIH: *Streptococcus pneumoniae* Family 2, Clade 3 Pneumococcal Surface Protein A (PspA UAB099) with C-Terminal Histidine Tag, Recombinant from *Escherichia coli*, NR-33179. The following reagent was obtained through BEI Resources, NIAID, NIH: H7 Hemagglutinin (HA) Protein from Influenza Virus, A/Netherlands/219/2003 (H7N7), Recombinant from Baculovirus, NR-2633. H1N1-NP was from SinoBiological (cat no. 11675-V08B). Endotoxin-free OVA was from Invivogen (cat no. vac-pova)

House dust mite-induced asthma. House dust mites *Dermatophagoides pteronyssinus* (HDM-Der p1, Greer Laboratories, cat no. XPB82D3A2.5) or *Dermatophagoides farinae* (HDM-Der f 1, Greer Laboratories, cat no. XPB81 D3A2.5) was suspended in endotoxin-free PBS at a concentration of 5 mg/ml. HDM was freshly prepared by mixing equal parts of HDM-Der p 1 and HDM-Der f 1 in PBS. To induce asthma, mice were sensitized intranasally (i.n.) with 3 daily doses of 1 μg HDM on days 0-2 and were later challenged with 10 μg of HDM i.n. on days 9-13. BAL fluid, blood, lungs and medLNs were collected on day 16. BAL fluid was collected in 0.7-1 ml PBS and blood was collected through cardiac puncture.

Lung histology. Lungs were fixed in 10% formalin, paraffin embedded and cut into 4-μm sections. Lung sections were then stained for hematoxylin-eosin. All staining procedures were performed by the histology core at the University of Florida.

Isolation of lung cells. Cells were isolated from the lung as previously described[21]. The lungs were perfused with ice cold PBS and removed. Lungs were digested in DMEM containing 200 μg/ml DNase I (Roche, 10104159001), 25

μg/ml Liberase TM (Roche, 05401119001) at 37° C. for 2 hours. Red blood cells were then lysed and a single cell suspension was prepared by filtering through a 70-μm cell strainer.

HDM ELISA. HDM-specific IgG1 and IgE were measured by ELISA in the serum of HDM treated mice. Secondary Abs used were anti-mouse IgG1-HRP (Southern Biotech, cat no.1070-05) and anti-mouse IgE-HRP (Southern Biotech, cat no.1110-05). To measure HDM-specific T cell responses, lung cells were restimulated with 25 μg/ml of HDM for 4 days. IL-5 cytokines were measured in the supernatant by ELISA.

Flow cytometry. Single cell suspensions were stained with flourescent-dye-conjugated antibodies in PBS containing 2% FBS and 1 mM EDTA. Surface stains were performed at 4° C. for 20 min. For intracellular cytokine or transcription factor stainings of murine and human cells, cells were fixed and permeabilized with the Foxp3 staining buffer set (eBioscience, cat no 00-5523-00). CD4$^{+}$FoxP3$^{+}$ T-regs in the lung were analyzed two weeks after the treatment. Data were acquired on a BD LSRFortessa and analyzed using FlowJo software package (FlowJo, LLC). Cell sorting was performed on the BD FACSAriaIII Flow Cytometer and Cell Sorter.

Adoptive transfer. cDC2 subpopulations were sorted from the lungs of naïve or HDM-treated mice with a FACSAriaIII flow cytometer. cDC2 were identified as MHCII$^{+}$CD11c$^{+}$ CD11b$^{+}$CD64$^{-}$. cDC2 subsets were defined as MHCII$^{+}$ CD11c$^{+}$CD11b$^{+}$TNFR2$^{+}$ and MHCII$^{+}$CD11c$^{+}$CD11b$^{+}$ TNFR2$^{-21}$. 500,000 cells were administered intranasally into recipient mice. DCs in the lungs were analyzed 24 hours later. T cells in the lung were analyzed 14 days later.

Human lung explants. Human lung explants were procured at the Lung Transplant Center, Division of Pulmonary, Critical Care and Sleep Medicine, Department of Medicine, University of Florida. Donor and patients consent for a research protocol (UF Lung Transplant Tissue/Databank (IRB201501133). Healthy donor lungs were surgically removed postmortem, perfused (ex vivo lung perfusion, EVLP), small pieces were cut from the right middle and lower lobes for research purpose, and stored in cold Perfadex® at 4° C. for no more than 12 hrs before processing. Ex planted lungs from emphysema lung transplant patients were stored in cold Perfadex® at 4° C. for no more than 12 hrs before the process. No lung explants were procured from prisoners.

Statistical Analysis. All data are expressed as means±SEM. Statistical significance was evaluated using Prism 6.0 software. One-way ANOVA was performed with post hoc Tukey's multiple comparison test, Mann-Whitney U-test, or Student's t-test applied as appropriate for comparisons between groups. A p-value of <0.05 was considered significant.

Example 8: Efficacy of IFNβ Treatment in Asthma

Figure 18:
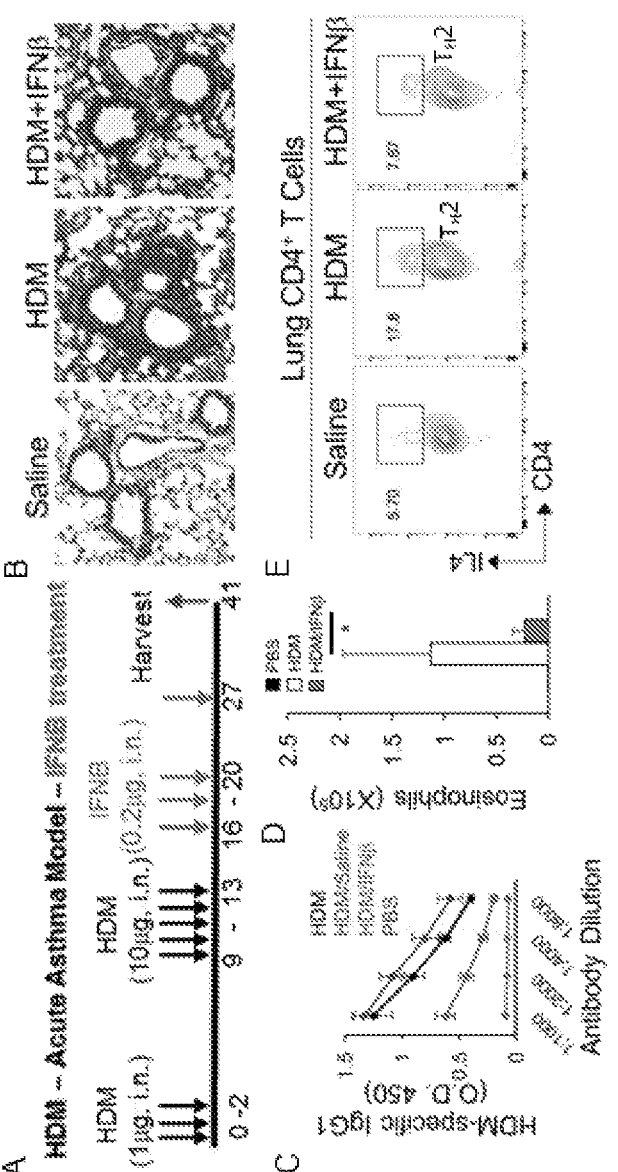
FIG. 18. Inhaled IFNβ alleviated HDM-induced acute asthma. A. Experimental protocol for treating HDM-induced acute asthma with IFNβ. (n=4 mice/group) B. Haematoxylin and eosin (H&E) staining of lung sections from asthma mice in (A). Data are representative of three independent experiments. C. Serum levels of HDM-specific IgG1 from asthma mice in (A). Data are representative of three independent experiments. D. Absolute numbers of eosinophils in the BALF from the asthma mice in (A). E. Flow cytometry analysis of lung IL-4-producing CD4$^+$ T cells re-stimulated with HDM ex vivo from asthma mice in (A). Data are representative of three independent experiments. Graphs represent the mean with error bars indication s.e.m. P values determined by unpaired student t-test. *P<0.05.

FIGS. 18-26 provide data of a series of experiments showing that IFNβ administration treats asthma. FIG. 18 shows that mice that inhaled IFNβ showed an alleviation of HDM-induced acute asthma. Specifically, HDM-specific IgG1 was reduced in animals that received IFNβ vs. control. Also, IFNβ treated animals had less eosinophils compared to control. IFNβ treated animals had less lung IL4+ Th2 cells.

Figure 19:
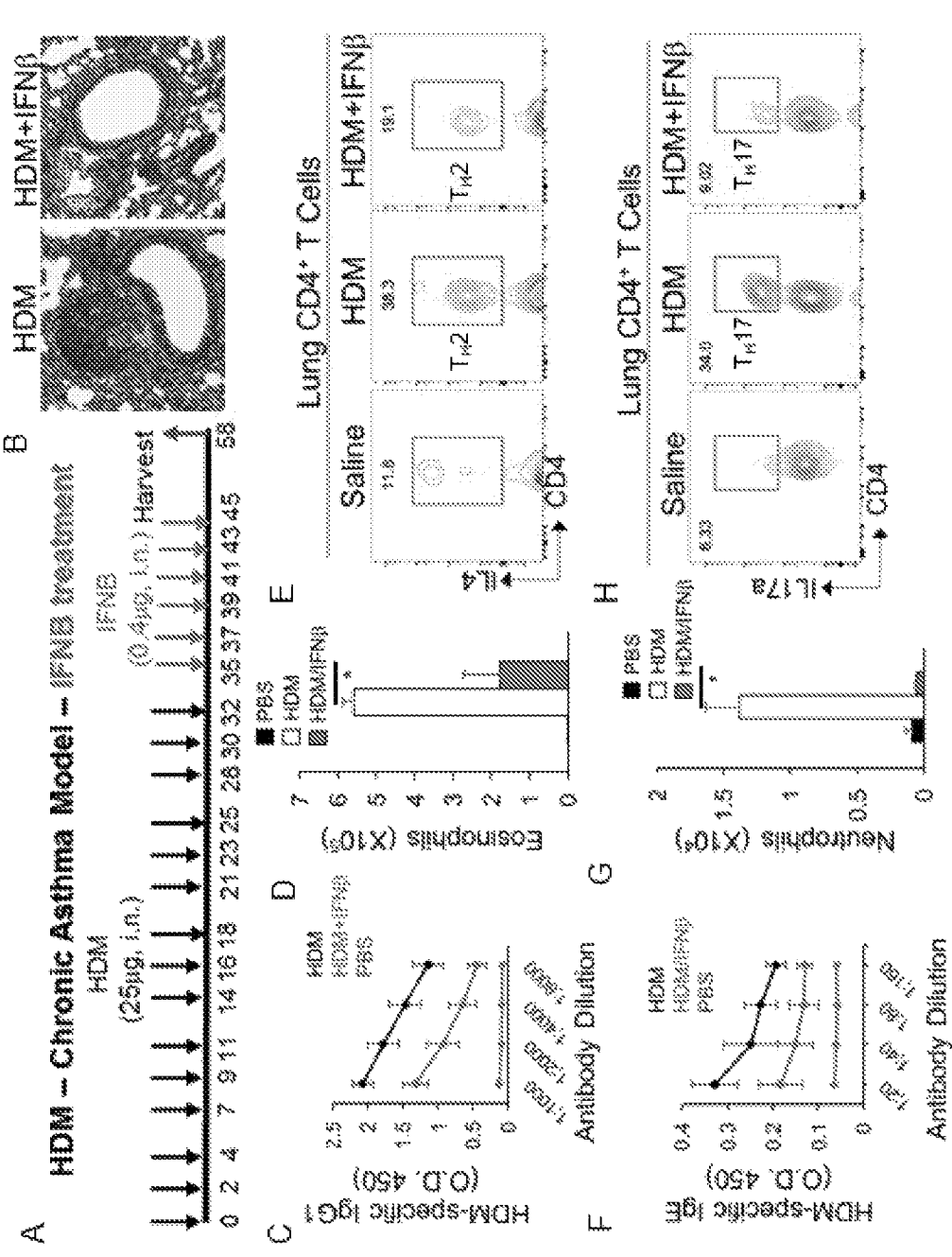
FIG. 19. Inhaled IFNβ alleviated HDM-induced chronic asthma. A. Experimental protocol for treating HDM-induced chronic asthma with IFNβ. (n=4 mice/group) B. Haematoxylin and eosin (H&E) staining of lung sections from asthma mice in (A). Data are representative of three independent experiments. C. Serum levels of HDM-specific IgG1 from asthma mice in (A). Data are representative of three independent experiments. D. Absolute numbers of eosinophils in the BALF from the asthma mice in (A). E. Flow cytometry analysis of lung IL-4-producing CD4$^+$ T cells re-stimulated with HDM ex vivo from asthma mice in (A). Data are representative of three independent experiments. F. Serum levels of HDM-specific IgE from asthma mice in (A). Data are representative of three independent experiments. G. Absolute numbers of neutrophils in the BALF from the asthma mice in (A). H. Flow cytometry analysis of lung IL-17-producing CD4$^+$ T cells re-stimulated with HDM ex vivo from asthma mice in (A). Data are representative of three independent experiments. Graphs represent the mean with error bars indication s.e.m. P values determined by unpaired student t-test. *P<0.05.
Figure 20:
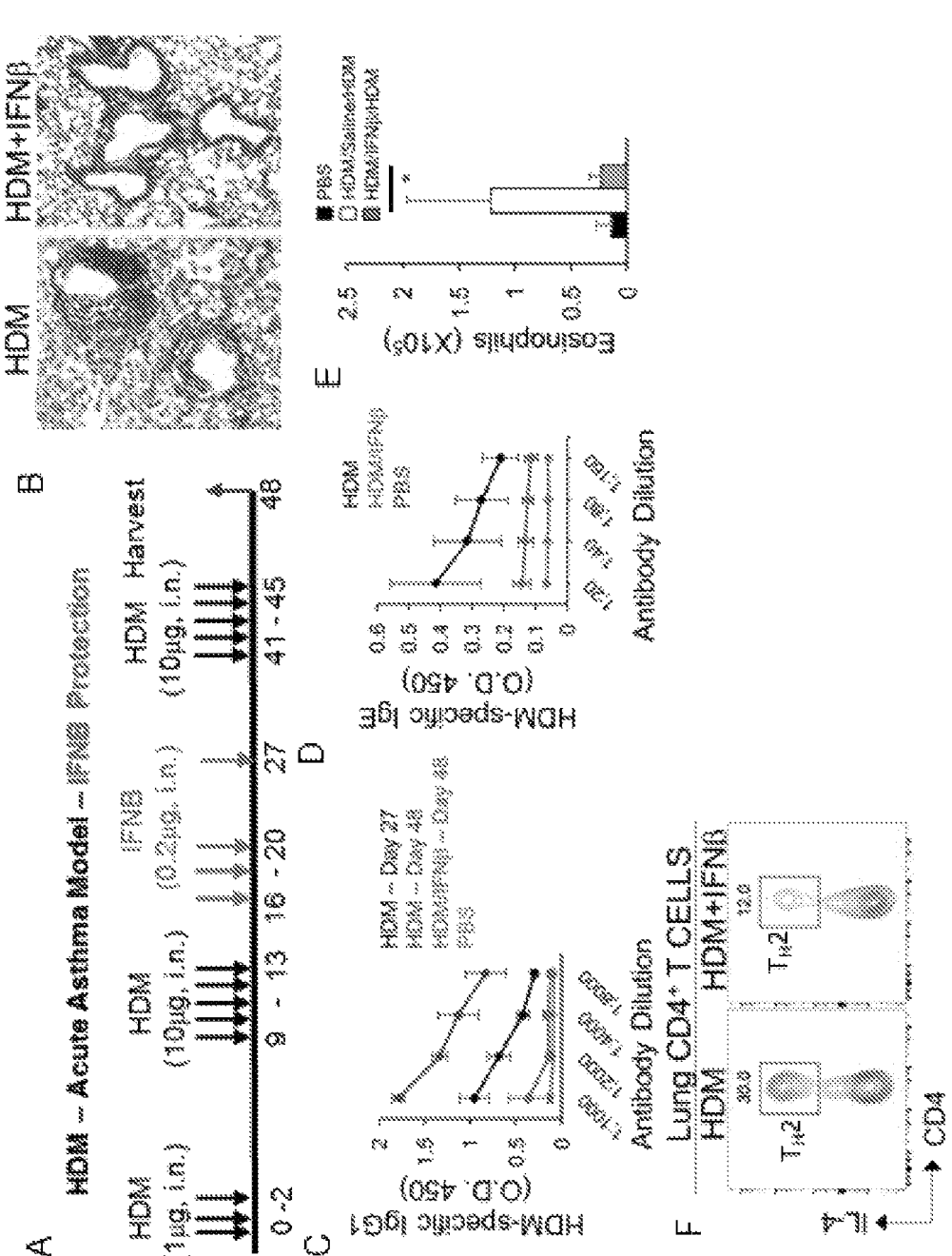
FIG. 20. Inhaled IFNβ prevented HDM-induced asthma attack. A. Experimental protocol for treating HDM-induced acute asthma with IFNβ. (n=4 mice/group) B. Haematoxylin and eosin (H&E) staining of lung sections from asthma mice in (A). Data are representative of three independent experiments. C-D. Serum levels of HDM-specific IgG1 (C) and IgE (D) from asthma mice in (A). Data are representative of three independent experiments. D. Absolute numbers of eosinophils in the BALF from the asthma mice in (A). E. Flow cytometry analysis of lung IL-4-producing CD4$^+$ T cells re-stimulated with HDM ex vivo from asthma mice in (A). Data are representative of three independent experiments. Graphs represent the mean with error bars indication s.e.m. P values determined by unpaired student t-test. *P<0.05.
Figure 21:
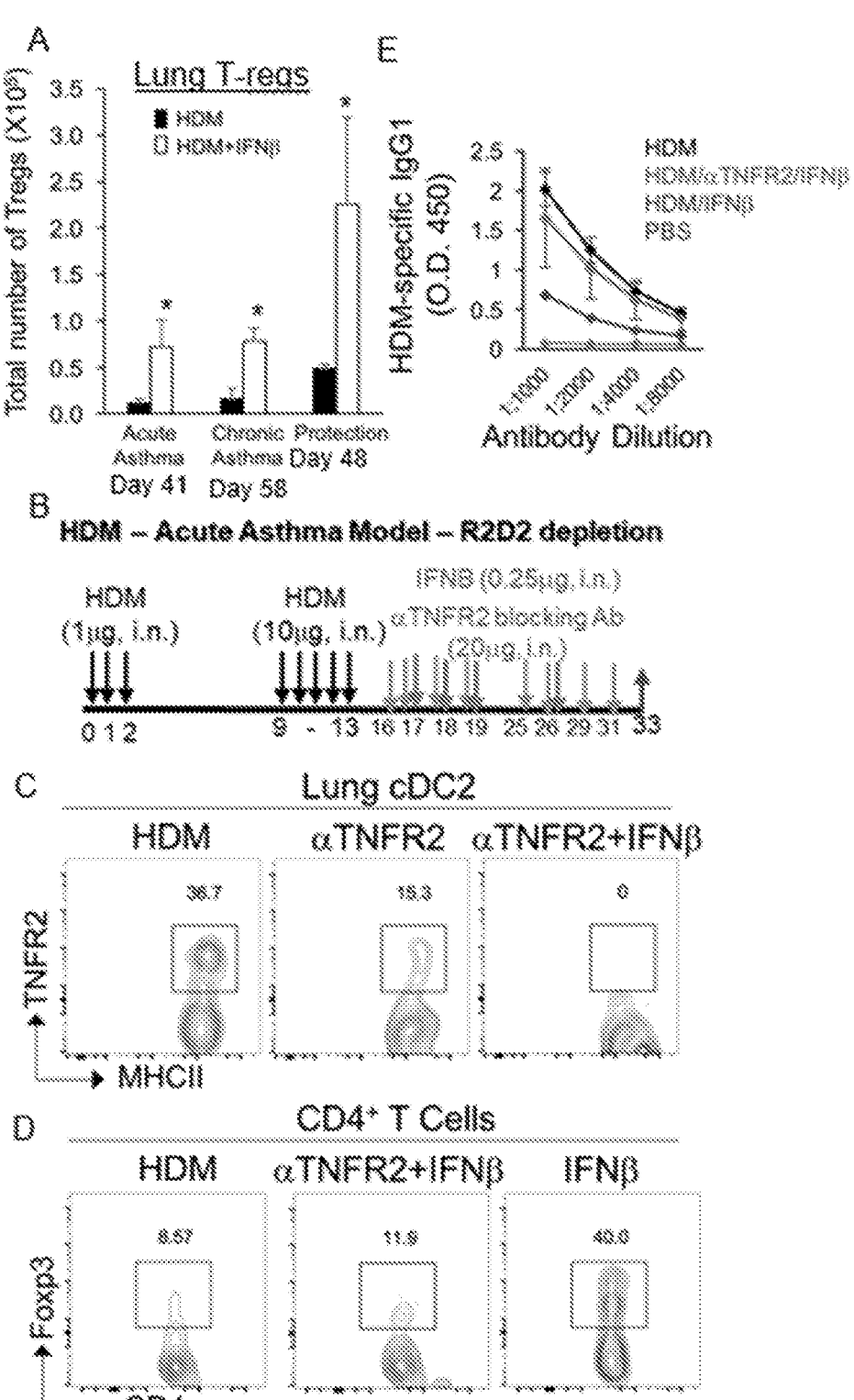
FIG. 21. Inhaled IFNβ generated lung regulatory T cells in HDM-induced asthma mice. A. Absolute number of Tregs in the lungs from HDM-induced asthma mice in FIGS. 1&2&3. (n=4 mice/group) Data are representative of three independent experiments. B. Experimental protocol for R2D2 cell depletion in HDM-induced asthma mice treated with IFNβ/isotype control or IFNβ and anti-TNFR2 antibody (20 μg). (n=4 mice/group). C. Flow cytometry plot of TNFR2$^+$ cDC2 on day 33 from mice in (B). Data are representative of three independent experiments. D. Flow cytometry plot of Foxp3$^+$ CD4$^+$ T cells on day 33 from mice in (B). Data are representative of three independent experiments. E. Serum levels of HDM-specific IgG1 from asthma mice in (B). Data are representative of three independent experiments. Graphs represent the mean with error bars indication s.e.m. P values determined by unpaired student t-test. *P<0.05.

The results in FIG. 19 show that IFNβ also alleviated HDM-induced chronic neutrophilic asthma. IFNβ treated animals showed less HDM-specific IgE antibodies compared to control; less neutrophils, eosinophils compared to control, and less IL-4 and IL-17 producing CD4+ T cells. FIG. 20 shows that IFNβ treatment prevented HDM-induced asthma attack in asthmatic mice including less HDM-specific IgE, IgG1, fewer IL-4+ Th2 cells and eosinophils in HDM re-challenged asthmatic mice. FIG. 21 shows that inhaled IFNβ generated lung regulatory T cells in HDM-induced asthma mice and block TNFR2 eliminated IFNβ induced lung regulatory T cells.

Figure 22:
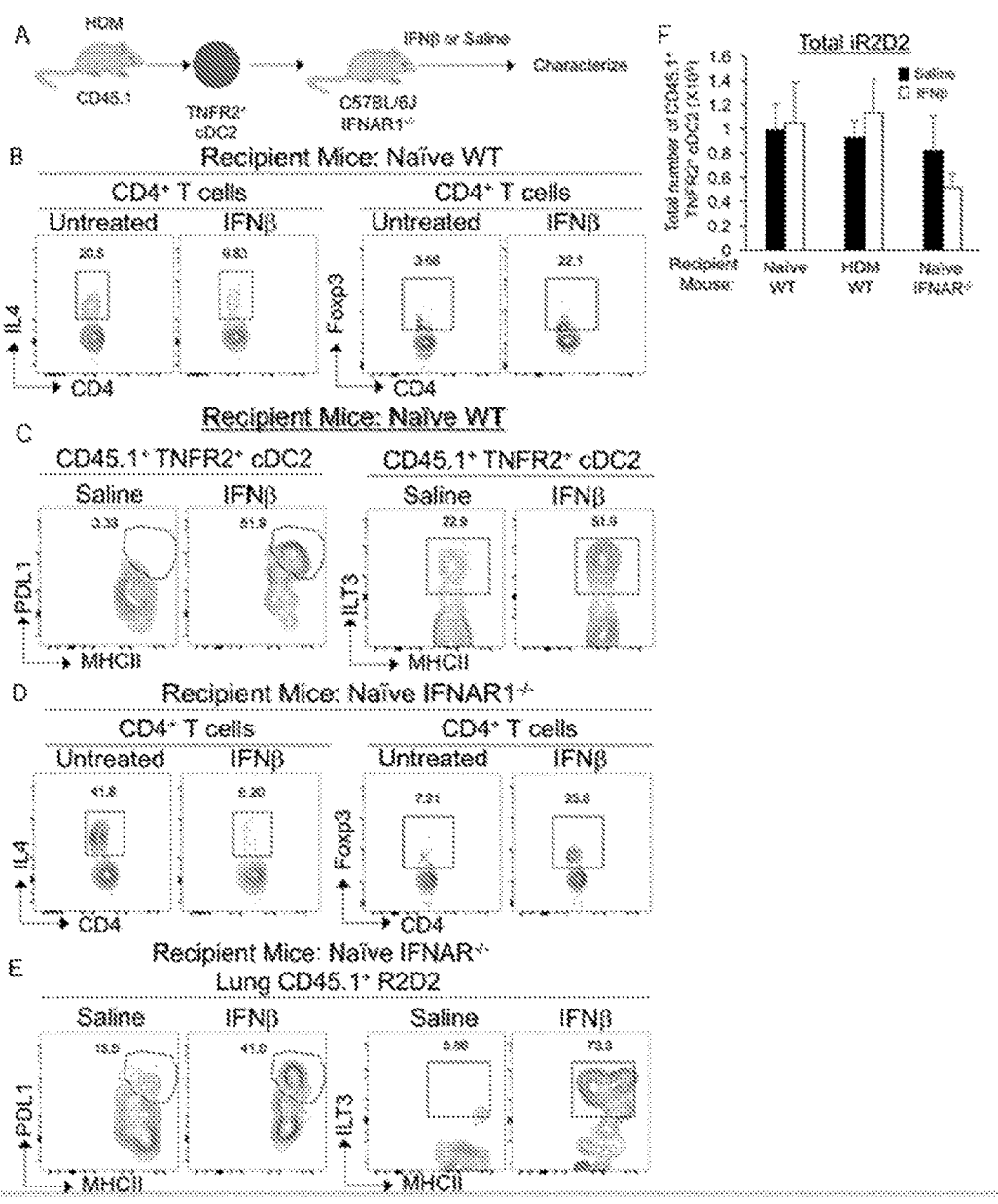
FIG. 22. Inhaled IFNβ reprogramed T$_H$2-promoting pathogenic lung R2D2 cells from asthma mice to generate regulation T cells in the lung. A. Experimental protocol for adoptively transfer (i.n.) lung R2D2 cells from HDM-induced asthma mice (CD45.1+) into a naïve C57BL/6J or IFNAR1$^{-/-}$ mouse (CD45.2+). 24 hrs later, the recipient mice were treated with IFNβ (200 ng, i.n.). Lung R2D2 cells were analyzed 24 hours later. Lung CD4+ T cells were analyzed 14 days later. (n=4mice/group) B. Flow cytometry analysis of IL-4+ or Foxp3+CD4+ T cells in the lung from the C57BL/6J recipient mice in (A). Data are representative of three independent experiments. C. Flow cytometry analysis of lung CD45.1+R2D2 cells in the lung from the C57BL/6J recipient mice in (A). Data are representative of three independent. D. Flow cytometry analysis of IL-4+ or Foxp3+CD4+ T cells in the lung from the IFNAR1$^{-/-}$ recipient mice in (A). Data are representative of three independent experiments. E. Flow cytometry analysis of lung CD45.1+R2D2 cells in the lung from the IFNAR1$^{-/-}$ recipient mice in (A). Data are representative of three independent. F. Total recovered CD45.1 R2D2 from the recipient mice. in (A). Data are representative of three independent. Graphs represent the mean with error bars indication s.e.m. P values determined by unpaired student t-test. *P<0.05.
Figure 23:
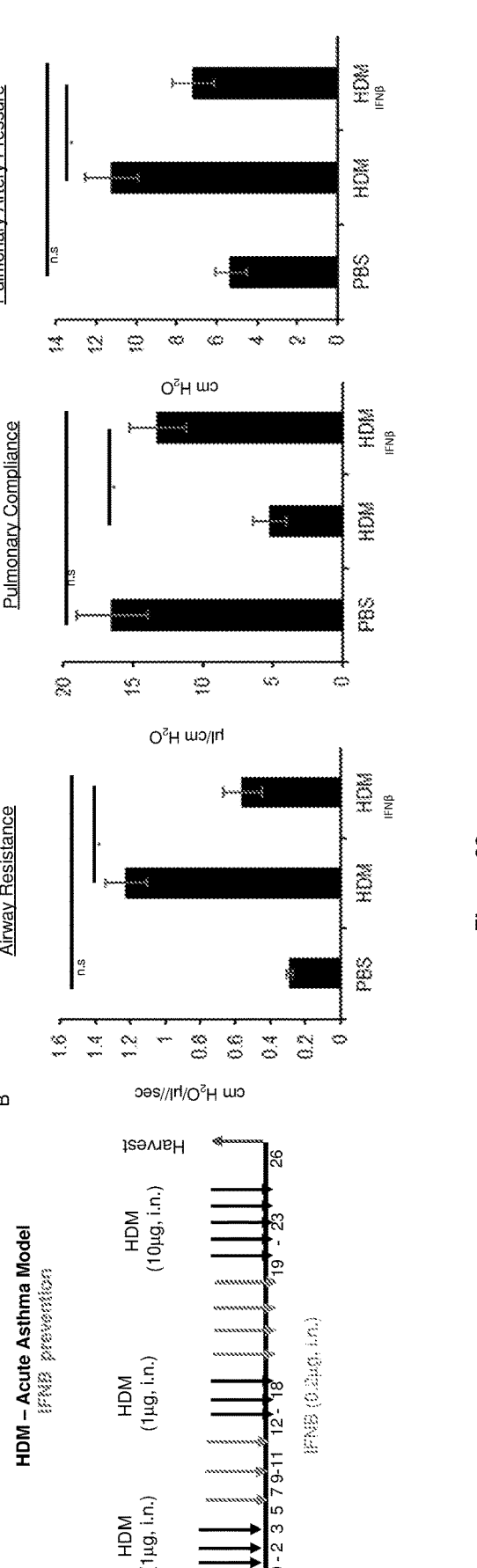
FIG. 23. Inhaled IFNβ prevents HDM-induced asthma. A. Experimental protocol for prevent HDM-induced asthma with IFNβ. (n=4 mice/group) B. Lung function were determined by an ex vivo lung perfusion system (EVLP) (Hugo Sachs Elektronik, March-Huggstetten, Germany) from mice in (A). Data are representative of three independent experiments. Data are representative of three independent experiments. Graphs represent the mean with error bars indication s.e.m. P values determined by unpaired student t-test. *P<0.05.
Figure 24:
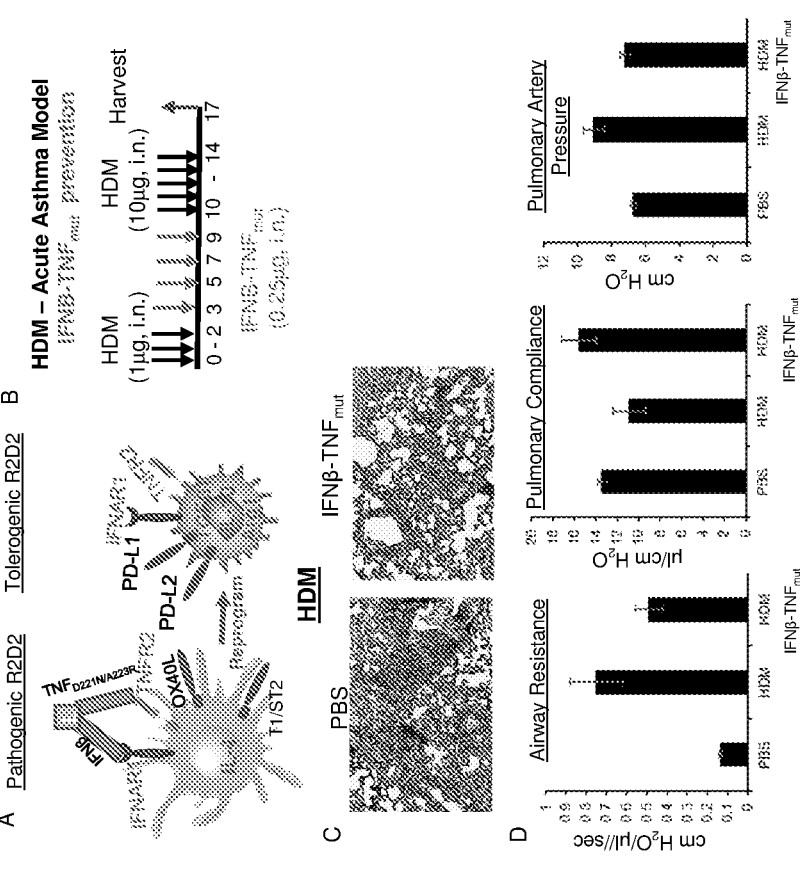
FIG. 24. Inhaled IFNβ-TNF$_{mut}$ fusion protein prevents HDM-induced asthma attack. A. Proposed mode of action for IFNβ-TNF$_{mut}$ fusion protein. B. Experimental protocol for prevent HDM-induced asthma with IFNβ-TNF$_{mut}$. (n=4 mice/group) C. Haematoxylin and eosin (H&E) staining of lung sections from asthma mice in (B). Data are representative of three independent experiments. D. Lung function were determined by an ex vivo lung perfusion system (EVLP) (Hugo Sachs Elektronik, March-Huggstetten, Germany) from mice in (B). Data are representative of three independent experiments. Graphs represent the mean with error bars indication s.e.m. P values determined by unpaired student t-test. *P<0.05.

FIG. 22 shows that inhaled IFNβ reprogramed $T_H2$-promoting pathogenic lung R2D2 cells in situ in the asthmatic mice to generate lung regulatory T cells. FIG. 23 measured lung function in IFNβ treated asthmatic mice re-challenged with HDM. IFNβ treated asthmatic mice had significantly improved airway resistance, pulmonary compliance, pulmonary artery pressure compared to untreated asthmatic mice upon further HDM challenge. FIG. 24 provide evidence that IFNβ-TNFmut fusion protein protect mice from HDM-induced asthma. Mice with inhaled IFNβ-$TNF_{mut}$ fusion protein had significantly improved lung functions compared to mice treated with vehicle.

Figure 25:
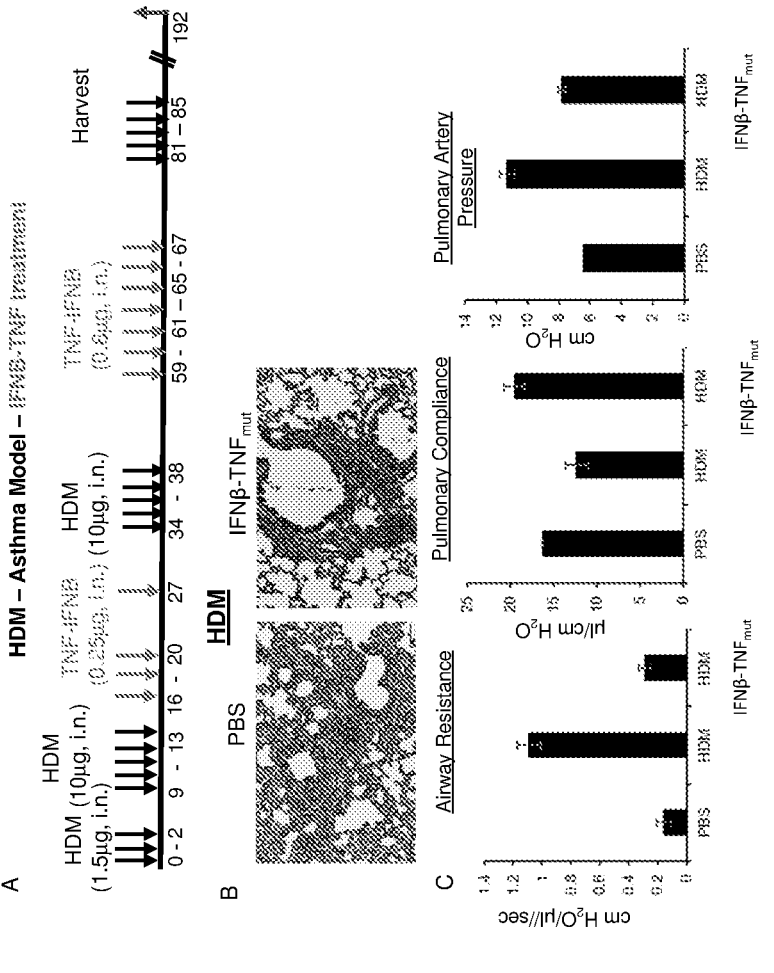
FIG. 25. Inhaled IFNβ-TNF$_{mut}$ induces long-lasting remission in asthma. A. Experimental protocol for treat HDM-induced asthma with IFNβ-TNF$_{mut}$. (n=4 mice/group) B. Haematoxylin and eosin (H&E) staining of lung sections from asthma mice in (A). Data are representative of three independent experiments.C. Lung function were determined by an ex vivo lung perfusion system (EVLP) (Hugo Sachs Elektronik, March-Huggstetten, Germany) from mice in (A). Data are representative of three independent experiments. Graphs represent the mean with error bars indication s.e.m. P values determined by unpaired student t-test. *P<0.05.
Figure 26:
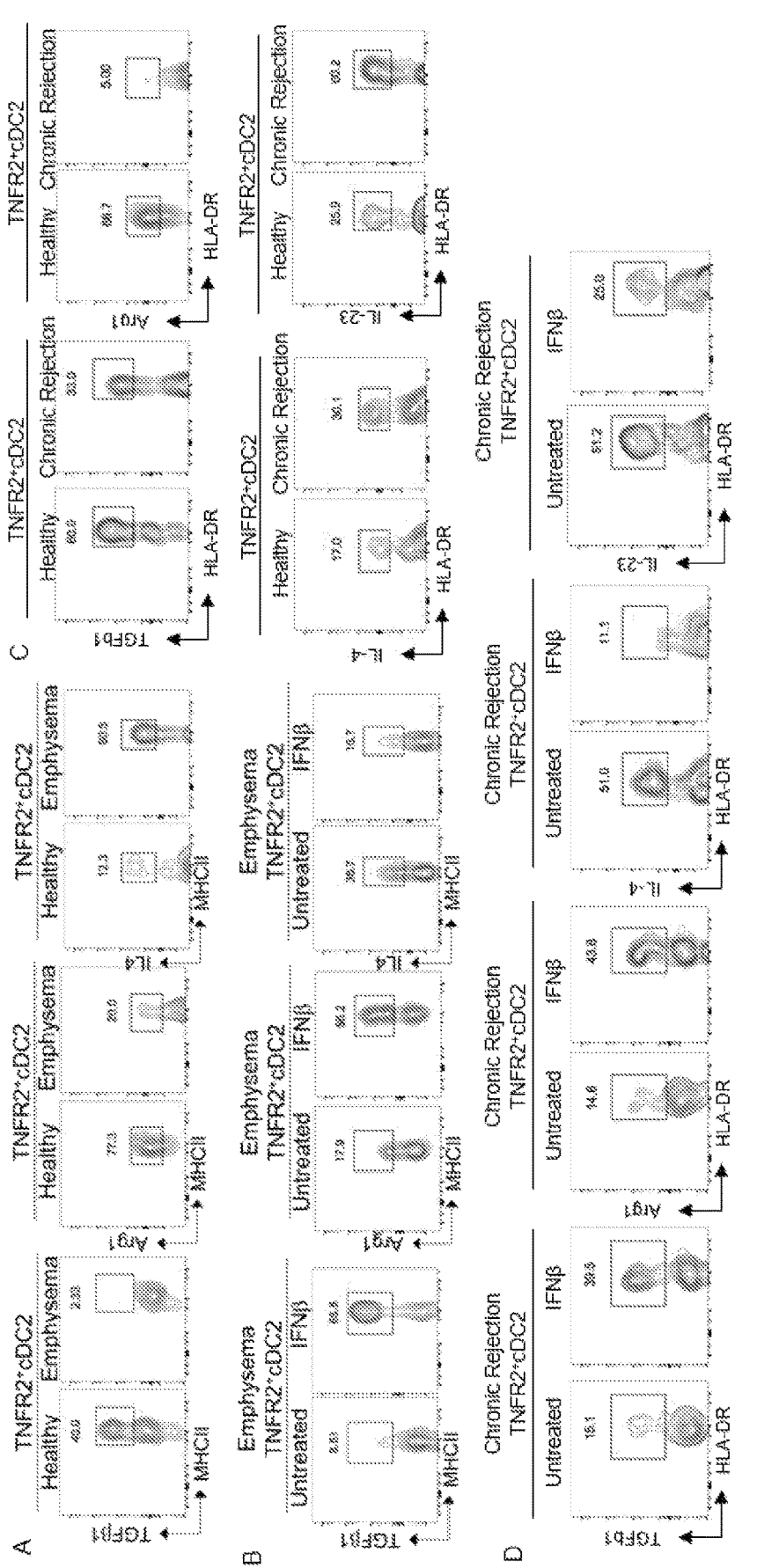
FIG. 26. IFNβ reprogramed pathogenic lung R2D2 cells from human lung disease patients. A,C. Flow cytometry analysis of TNFR2+ cDC2 in healthy, emphysema human lungs (A) or chronic lung rejection patients (C). Data were compiled from multiple independent experiments.B,D. Flow cytometry analysis of TNFR2+ cDC2 in human lung cells from emphysema (B) or chronic lung rejection patients (D) treated with human recombinant IFNβ. Data were compiled from multiple independent experiments.

FIG. 25 shows that inhaled IFNβ-$TNF_{mut}$ induces long-lasting remission in asthmatic mice. Asthmatic mice were treated with IFNβ-$TNF_{mut}$ fusion protein and challenged with HDM two weeks later. Mouse lung functions were measured 107 days later. Asthmatic mice treated with inhaled IFNβ-$TNF_{mut}$ fusion protein had significantly improved lung functions compared to mice treated with vehicle even 3 months later. FIG. 26, using human IFNβ, we showed that exogenous IFNβ can inhibit IL-4 and IL-23 production and increase TGF-β1, Arginase 1 expression in pathogenic lung R2D2 cells from chronic rejection and emphysema patients.

The present invention is not limited to the particular embodiments and examples described above, and various modifications can be made within the scope of the appended claims. Other embodiments provided by suitably combining technical means disclosed in separate embodiments of the present invention are also within the technical scope of the present invention. All the academic publications and patent literature cited in the description are incorporated herein by reference.

What is claimed is:

1. A method for treating asthma or chronic obstructive pulmonary disease (COPD), comprising administering by pulmonary or intranasal delivery to a subject in need thereof a pharmaceutical composition comprising a therapeutically effective amount of interferon-beta (IFNB) or an IFNB fusion protein, wherein the IFNB or the IFNB fusion protein comprises the sequence of SEQ ID NO: 2 or SEQ ID NO: 3.

2. The method of claim 1, wherein the IFNB fusion protein comprises an IFNB-Tumor necrosis factor (TNF) fusion protein.

3. The method of claim 2, wherein the IFNB-TNF fusion protein comprises SEQ ID NO: 2 linked to SEQ ID NO: 5, a fragment of SEQ ID NO: 5, or a variant of SEQ ID NO: 5 having at least 90% identity therewith.

4. The method of claim 2, wherein the IFNB-TNF fusion protein comprises SEQ ID NO: 2 linked to SEQ ID NO: 5.

5. The method of claim 1, wherein the pharmaceutical composition is in a form for inhalation.

6. The method of claim 1, wherein the therapeutically effective amount is an amount sufficient to induce lung T regulatory cells.

7. The method of claim 1, wherein the pharmaceutical composition is an aerosol.

8. The method of claim 1, wherein the method treats asthma.

9. The method of claim 1, wherein the pharmaceutical composition further comprises a steroid or methotrexate.

10. The method of claim 1, wherein the pharmaceutical composition lacks a neuraminidase inhibitor.

11. The method of claim 1, wherein the IFNB fusion protein comprises an anti-TNFR2 non-blocking antibody fused to IFNB.

12. The method of claim 1, wherein the IFNB fusion protein comprises an anti-Mg12 antibody fused to IFNB.

\* \* \* \* \*

SEQUENCE LISTING

<160> NUMBER OF SEQ ID NOS: 10

<210> SEQ ID NO 1
<211> LENGTH: 839
<212> TYPE: DNA
<213> ORGANISM: Homo sapiens

<400> SEQUENCE: 1

```
attctaactg caacctttcg aagcctttgc tctggcacaa caggtagtag gcgacactgt      60
tcgtgttgtc aacatgacca acaagtgtct cctccaaatt gctctcctgt tgtgcttctc     120
cactacagct ctttccatga gctacaactt gcttggattc ctacaaagaa gcagcaattt     180
tcagtgtcag aagctcctgt ggcaattgaa tgggaggctt gaatactgcc tcaaggacag     240
gatgaacttt gacatccctg aggagattaa gcagctgcag cagttccaga aggaggacgc     300
cgcattgacc atctatgaga tgctccagaa catctttgct attttcagac aagattcatc     360
tagcactggc tggaatgaga ctattgttga gaacctcctg gctaatgtct atcatcagat     420
aaaccatctg aagacagtcc tggaagaaaa actggagaaa gaagatttca ccaggggaaa     480
actcatgagc agtctgcacc tgaaaagata ttatgggagg attctgcatt acctgaaggc     540
caaggagtac agtcactgtg cctggaccat agtcagagtg gaaatcctaa ggaactttta     600
cttcattaac agacttacag gttacctccg aaactgaaga tctcctagcc tgtgcctctg     660
ggactggaca attgcttcaa gcattcttca accagcagat gctgtttaag tgactgatgg     720
ctaatgtact gcatatgaaa ggacactaga agattttgaa atttttatta aattatgagt     780
tatttttatt tatttaaatt ttattttgga aaataaatta tttttggtgc aaaagtcaa      839
```

<210> SEQ ID NO 2
<211> LENGTH: 166
<212> TYPE: PRT
<213> ORGANISM: Homo sapiens

<400> SEQUENCE: 2

Met Ser Tyr Asn Leu Leu Gly Phe Leu Gln Arg Ser Ser Asn Phe Gln

-continued

```
1               5               10              15

Cys Gln Lys Leu Leu Trp Gln Leu Asn Gly Arg Leu Glu Tyr Cys Leu
            20              25              30

Lys Asp Arg Met Asn Phe Asp Ile Pro Glu Glu Ile Lys Gln Leu Gln
            35              40              45

Gln Phe Gln Lys Glu Asp Ala Ala Leu Thr Ile Tyr Glu Met Leu Gln
            50              55              60

Asn Ile Phe Ala Ile Phe Arg Gln Asp Ser Ser Ser Thr Gly Trp Asn
65              70              75              80

Glu Thr Ile Val Glu Asn Leu Leu Ala Asn Val Tyr His Gln Ile Asn
                85              90              95

His Leu Lys Thr Val Leu Glu Glu Lys Leu Glu Lys Glu Asp Phe Thr
            100             105             110

Arg Gly Lys Leu Met Ser Ser Leu His Leu Lys Arg Tyr Tyr Gly Arg
            115             120             125

Ile Leu His Tyr Leu Lys Ala Lys Glu Tyr Ser His Cys Ala Trp Thr
            130             135             140

Ile Val Arg Val Glu Ile Leu Arg Asn Phe Tyr Phe Ile Asn Arg Leu
145             150             155             160

Thr Gly Tyr Leu Arg Asn
            165
```

<210> SEQ ID NO 3
<211> LENGTH: 187
<212> TYPE: PRT
<213> ORGANISM: Homo sapiens

<400> SEQUENCE: 3

```
Met Thr Asn Lys Cys Leu Leu Gln Ile Ala Leu Leu Leu Cys Phe Ser
1               5               10              15

Thr Thr Ala Leu Ser Met Ser Tyr Asn Leu Leu Gly Phe Leu Gln Arg
            20              25              30

Ser Ser Asn Phe Gln Cys Gln Lys Leu Leu Trp Gln Leu Asn Gly Arg
            35              40              45

Leu Glu Tyr Cys Leu Lys Asp Arg Met Asn Phe Asp Ile Pro Glu Glu
        50              55              60

Ile Lys Gln Leu Gln Gln Phe Gln Lys Glu Asp Ala Ala Leu Thr Ile
65              70              75              80

Tyr Glu Met Leu Gln Asn Ile Phe Ala Ile Phe Arg Gln Asp Ser Ser
                85              90              95

Ser Thr Gly Trp Asn Glu Thr Ile Val Glu Asn Leu Leu Ala Asn Val
            100             105             110

Tyr His Gln Ile Asn His Leu Lys Thr Val Leu Glu Glu Lys Leu Glu
            115             120             125

Lys Glu Asp Phe Thr Arg Gly Lys Leu Met Ser Ser Leu His Leu Lys
            130             135             140

Arg Tyr Tyr Gly Arg Ile Leu His Tyr Leu Lys Ala Lys Glu Tyr Ser
145             150             155             160

His Cys Ala Trp Thr Ile Val Arg Val Glu Ile Leu Arg Asn Phe Tyr
                165             170             175

Phe Ile Asn Arg Leu Thr Gly Tyr Leu Arg Asn
            180             185
```

<210> SEQ ID NO 4
<211> LENGTH: 166

```
<212> TYPE: PRT
<213> ORGANISM: Homo sapiens

<400> SEQUENCE: 4

Met Ser Tyr Asn Leu Leu Gly Phe Leu Gln Arg Ser Ser Asn Phe Gln
1               5                   10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
            115                 120                 125

Ile Leu His Tyr Leu Lys Ala Lys Glu Tyr Ser His Cys Ala Trp Thr
        130                 135                 140

Ile Val Arg Val Glu Ile Leu Arg Asn Phe Tyr Phe Ile Asn Arg Leu
145                 150                 155                 160

Thr Gly Tyr Leu Arg Asn
                165

<210> SEQ ID NO 5
<211> LENGTH: 157
<212> TYPE: PRT
<213> ORGANISM: Homo sapiens

<400> SEQUENCE: 5

Val Arg Ser Ser Ser Arg Thr Pro Ser Asp Lys Pro Val Ala His Val
1               5                   10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Lys Gly Gln Gly Cys Pro Ser Thr His Val Leu Leu Thr His Thr Ile
65                  70                  75                  80

Ser Arg Ile Ala Val Ser Tyr Gln Thr Lys Val Asn Leu Leu Ser Ala
                85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
            115                 120                 125

Gly Asp Arg Leu Ser Ala Glu Ile Asn Arg Pro Asp Tyr Leu Asn Phe
        130                 135                 140

Arg Glu Ser Gly Gln Val Tyr Phe Gly Ile Ile Ala Leu
145                 150                 155

<210> SEQ ID NO 6
<211> LENGTH: 161
```

```
<212> TYPE: PRT
<213> ORGANISM: Mus musculus

<400> SEQUENCE: 6

Ile Asn Tyr Lys Gln Leu Gln Leu Gln Glu Arg Thr Asn Ile Arg Lys
1               5                   10                  15

Cys Gln Glu Leu Leu Glu Gln Leu Asn Gly Lys Ile Asn Leu Thr Tyr
                20                  25                  30

Arg Ala Asp Phe Lys Ile Pro Met Glu Met Thr Glu Lys Met Gln Lys
            35                  40                  45

Ser Tyr Thr Ala Phe Ala Ile Gln Glu Met Leu Gln Asn Val Phe Leu
        50                  55                  60

Val Phe Arg Asn Asn Phe Ser Ser Thr Gly Trp Asn Glu Thr Ile Val
65                  70                  75                  80

Val Arg Leu Leu Asp Glu Leu His Gln Gln Thr Val Phe Leu Lys Thr
                85                  90                  95

Val Leu Glu Glu Lys Gln Glu Glu Arg Leu Thr Trp Glu Met Ser Ser
                100                 105                 110

Thr Ala Leu His Leu Lys Ser Tyr Tyr Trp Arg Val Gln Arg Tyr Leu
            115                 120                 125

Lys Leu Met Lys Tyr Asn Ser Tyr Ala Trp Met Val Val Arg Ala Glu
        130                 135                 140

Ile Phe Arg Asn Phe Leu Ile Ile Arg Arg Leu Thr Arg Asn Phe Gln
145                 150                 155                 160

Asn

<210> SEQ ID NO 7
<211> LENGTH: 156
<212> TYPE: PRT
<213> ORGANISM: Mus musculus

<400> SEQUENCE: 7

Leu Arg Ser Ser Ser Gln Asn Ser Ser Asp Lys Pro Val Ala His Val
1               5                   10                  15

Val Ala Asn His Gln Val Glu Glu Gln Leu Glu Trp Leu Ser Gln Arg
                20                  25                  30

Ala Asn Ala Leu Leu Ala Asn Gly Met Asp Leu Lys Asp Asn Gln Leu
            35                  40                  45

Val Val Pro Ala Asp Gly Leu Tyr Leu Val Tyr Ser Gln Val Leu Phe
        50                  55                  60

Lys Gly Gln Gly Cys Pro Asp Tyr Val Leu Leu Thr His Thr Val Ser
65                  70                  75                  80

Arg Phe Ala Ile Ser Tyr Gln Glu Lys Val Asn Leu Leu Ser Ala Val
                85                  90                  95

Lys Ser Pro Cys Pro Lys Asp Thr Pro Glu Gly Ala Glu Leu Lys Pro
            100                 105                 110

Trp Tyr Glu Pro Ile Tyr Leu Gly Gly Val Phe Gln Leu Glu Lys Gly
            115                 120                 125

Asp Gln Leu Ser Ala Glu Val Asn Leu Pro Lys Tyr Leu Asn Phe Arg
        130                 135                 140

Glu Ser Gly Gln Val Tyr Phe Gly Val Ile Ala Leu
145                 150                 155

<210> SEQ ID NO 8
<211> LENGTH: 232
<212> TYPE: PRT
```

```
<213> ORGANISM: Homo sapiens

<400> SEQUENCE: 8

Met Ser Thr Glu Met Ile Arg Asp Val Glu Leu Ala Glu Glu Ala Leu
1               5                   10                  15

Pro Lys Lys Thr Gly Gly Pro Gln Gly Ser Arg Arg Cys Leu Phe Leu
                20                  25                  30

Ser Leu Phe Ser Phe Leu Ile Val Ala Gly Ala Thr Thr Leu Phe Cys
            35                  40                  45

Leu Leu His Phe Gly Val Ile Gly Pro Gln Arg Glu Glu Phe Pro Arg
        50                  55                  60

Asp Leu Ser Leu Ile Ser Pro Leu Ala Gln Ala Val Arg Ser Ser Ser
65                  70                  75                  80

Arg Thr Pro Ser Asp Lys Pro Val Ala His Val Val Ala Asn Pro Gln
                85                  90                  95

Ala Glu Gly Gln Leu Gln Trp Leu Asn Arg Arg Ala Asn Ala Leu Leu
                100                 105                 110

Ala Asn Gly Val Glu Leu Arg Asp Asn Gln Leu Val Val Pro Ser Glu
            115                 120                 125

Gly Leu Tyr Leu Ile Tyr Ser Gln Val Leu Phe Lys Gly Gln Gly Cys
        130                 135                 140

Pro Ser Thr His Val Leu Leu Thr His Thr Ile Ser Arg Ile Ala Val
145                 150                 155                 160

Ser Tyr Gln Thr Lys Val Asn Leu Leu Ser Ala Ile Lys Ser Pro Cys
                165                 170                 175

Gln Arg Glu Thr Pro Glu Gly Ala Glu Ala Lys Pro Trp Tyr Glu Pro
                180                 185                 190

Ile Tyr Leu Gly Gly Val Phe Gln Leu Glu Lys Gly Asp Arg Leu Ser
            195                 200                 205

Ala Glu Ile Asn Arg Pro Asp Tyr Leu Asn Phe Arg Glu Ser Gly Gln
        210                 215                 220

Val Tyr Phe Gly Ile Ile Ala Leu
225                 230

<210> SEQ ID NO 9
<211> LENGTH: 182
<212> TYPE: PRT
<213> ORGANISM: Mus musculus

<400> SEQUENCE: 9

Met Asn Asn Arg Trp Ile Leu His Ala Ala Phe Leu Leu Cys Phe Ser
1               5                   10                  15

Thr Thr Ala Leu Ser Ile Asn Tyr Lys Gln Leu Gln Leu Gln Glu Arg
                20                  25                  30

Thr Asn Ile Arg Lys Cys Gln Glu Leu Leu Glu Gln Leu Asn Gly Lys
            35                  40                  45

Ile Asn Leu Thr Tyr Arg Ala Asp Phe Lys Ile Pro Met Glu Met Thr
        50                  55                  60

Glu Lys Met Gln Lys Ser Tyr Thr Ala Phe Ala Ile Gln Glu Met Leu
65                  70                  75                  80

Gln Asn Val Phe Leu Val Phe Arg Asn Asn Phe Ser Ser Thr Gly Trp
                85                  90                  95

Asn Glu Thr Ile Val Val Arg Leu Leu Asp Glu Leu His Gln Gln Thr
                100                 105                 110

Val Phe Leu Lys Thr Val Leu Glu Glu Lys Gln Glu Glu Arg Leu Thr
```

-continued

```
              115                 120                 125
Trp Glu Met Ser Ser Thr Ala Leu His Leu Lys Ser Tyr Tyr Trp Arg
    130                 135                 140

Val Gln Arg Tyr Leu Lys Leu Met Lys Tyr Asn Ser Tyr Ala Trp Met
145                 150                 155                 160

Val Val Arg Ala Glu Ile Phe Arg Asn Phe Leu Ile Ile Arg Arg Leu
                165                 170                 175

Thr Arg Asn Phe Gln Asn
            180

<210> SEQ ID NO 10
<211> LENGTH: 235
<212> TYPE: PRT
<213> ORGANISM: Mus musculus

<400> SEQUENCE: 10

Met Ser Thr Glu Ser Met Ile Arg Asp Val Glu Leu Ala Glu Glu Ala
1               5                  10                  15

Leu Pro Gln Lys Met Gly Gly Phe Gln Asn Ser Arg Arg Cys Leu Cys
            20                  25                  30

Leu Ser Leu Phe Ser Phe Leu Leu Val Ala Gly Ala Thr Thr Leu Phe
        35                  40                  45

Cys Leu Leu Asn Phe Gly Val Ile Gly Pro Gln Arg Asp Glu Lys Phe
    50                  55                  60

Pro Asn Gly Leu Pro Leu Ile Ser Ser Met Ala Gln Thr Leu Thr Leu
65                  70                  75                  80

Arg Ser Ser Ser Gln Asn Ser Ser Asp Lys Pro Val Ala His Val Val
                85                  90                  95

Ala Asn His Gln Val Glu Glu Gln Leu Glu Trp Leu Ser Gln Arg Ala
            100                 105                 110

Asn Ala Leu Leu Ala Asn Gly Met Asp Leu Lys Asp Asn Gln Leu Val
            115                 120                 125

Val Pro Ala Asp Gly Leu Tyr Leu Val Tyr Ser Gln Val Leu Phe Lys
    130                 135                 140

Gly Gln Gly Cys Pro Asp Tyr Val Leu Leu Thr His Thr Val Ser Arg
145                 150                 155                 160

Phe Ala Ile Ser Tyr Gln Glu Lys Val Asn Leu Leu Ser Ala Val Lys
            165                 170                 175

Ser Pro Cys Pro Lys Asp Thr Pro Glu Gly Ala Glu Leu Lys Pro Trp
            180                 185                 190

Tyr Glu Pro Ile Tyr Leu Gly Gly Val Phe Gln Leu Glu Lys Gly Asp
        195                 200                 205

Gln Leu Ser Ala Glu Val Asn Leu Pro Lys Tyr Leu Asn Phe Arg Glu
    210                 215                 220

Ser Gly Gln Val Tyr Phe Gly Val Ile Ala Leu
225                 230                 235
```